US010245098B2

(12) United States Patent
Davalos et al.

(10) Patent No.: US 10,245,098 B2
(45) Date of Patent: Apr. 2, 2019

(54) ACUTE BLOOD-BRAIN BARRIER DISRUPTION USING ELECTRICAL ENERGY BASED THERAPY

(71) Applicant: Virginia Tech Intellectual Properties, Inc., Blacksburg, VA (US)

(72) Inventors: Rafael V. Davalos, Blacksburg, VA (US); John H. Rossmeisl, Blacksburg, VA (US); Paulo A. Garcia, Blacksburg, VA (US)

( * ) Notice: Subject to any disclaimer, the term of this patent is extended or adjusted under 35 U.S.C. 154(b) by 230 days.

(21) Appl. No.: 14/017,210

(22) Filed: Sep. 3, 2013

(65) Prior Publication Data

US 2014/0039489 A1    Feb. 6, 2014
US 2016/0338758 A9    Nov. 24, 2016

Related U.S. Application Data

(63) Continuation-in-part of application No. 12/491,151, filed on Jun. 24, 2009, now Pat. No. 8,992,517, and
(Continued)

(51) Int. Cl.
    *A61B 18/14*      (2006.01)
    *A61B 18/12*      (2006.01)
(Continued)

(52) U.S. Cl.
    CPC .......... *A61B 18/1206* (2013.01); *A61B 18/14* (2013.01); *A61B 18/1477* (2013.01);
(Continued)

(58) Field of Classification Search
    CPC . A61B 18/1206; A61B 18/1477; A61B 18/14; A61B 2018/00613;
(Continued)

(56) References Cited

U.S. PATENT DOCUMENTS 1,653,819 A    12/1927   Northcott et al.
3,730,238 A    5/1973   Butler
(Continued)

FOREIGN PATENT DOCUMENTS

AU    2002315095 A1    12/2002
AU    2003227960 A1    12/2003
(Continued)

OTHER PUBLICATIONS

Hjouj et al "MRI Study on Reversible and Irreversible Electroporation INduced Blood Brain Brrier Disruption", PLOS ONE, Aug. 2012, 7:8 e42817.*
(Continued)

*Primary Examiner* — Michael F Peffley
(74) *Attorney, Agent, or Firm* — New River Valley IP Law, PC; Michele L. Mayberry; Timothy D. Nolan

(57) ABSTRACT

A method is provided for ablating brain tissue of a living mammal comprising: placing first and second electrodes in a brain of the living mammal; applying a plurality of electrical pulses through the first and second placed electrodes which are predetermined to: cause irreversible electroporation (IRE) of brain tissue of the mammal within a target ablation zone; and cause a temporary disruption of a blood brain barrier (BBB) within a surrounding zone that surrounds the target ablation zone to allow material in a blood vessel to be transferred to the surrounding zone through the temporarily disrupted BBB. Such methods are useful for delivering large molecule material within a blood vessel of the brain across the BBB, where the large molecule is otherwise blocked by the BBB from passing through the blood vessel into the brain.

18 Claims, 13 Drawing Sheets

Related U.S. Application Data a continuation-in-part of application No. 12/432,295, filed on Apr. 29, 2009, now Pat. No. 9,598,691, which is a continuation-in-part of application No. 13/550,307, filed on Jul. 16, 2012.

(60) Provisional application No. 61/695,705, filed on Aug. 31, 2012, provisional application No. 61/171,564, filed on Apr. 22, 2009, provisional application No. 61/167,997, filed on Apr. 9, 2009, provisional application No. 61/075,216, filed on Jun. 24, 2008, provisional application No. 61/125,840, filed on Apr. 29, 2008.

(51) Int. Cl.
*A61N 1/32* (2006.01)
*C12N 13/00* (2006.01)
*A61N 1/05* (2006.01)
*A61B 18/00* (2006.01)
*A61B 34/10* (2016.01)

(52) U.S. Cl.
CPC ............ *A61N 1/327* (2013.01); *C12N 13/00* (2013.01); *A61B 2018/00446* (2013.01); *A61B 2018/00577* (2013.01); *A61B 2018/00613* (2013.01); *A61B 2034/104* (2016.02); *A61N 1/05* (2013.01)

(58) Field of Classification Search
CPC ........... A61B 2018/00577; A61B 2018/00446; A61B 2034/104; A61N 1/327; A61N 1/05; C12N 13/00
See application file for complete search history.

(56) References Cited

U.S. PATENT DOCUMENTS

| | | |
|---|---|---|
| 3,746,004 A | 7/1973 | Jankelson |
| 3,871,359 A | 3/1975 | Pacela |
| 4,016,886 A | 4/1977 | Doss et al. |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| D294,519 S | 3/1988 | Hardy |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney et al. |
| 5,141,499 A | 8/1992 | Zappacosta |
| D329,496 S | 9/1992 | Wotton |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| D343,687 S | 1/1994 | Houghton et al. |
| 5,277,201 A | 1/1994 | Stern |
| 5,279,564 A | 1/1994 | Taylor |
| 5,281,213 A | 1/1994 | Milder |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| 5,348,554 A | 9/1994 | Imran et al. |
| D351,661 S | 10/1994 | Fischer |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,425,752 A | 6/1995 | Vu Nguyen |
| 5,439,440 A | 8/1995 | Hofmann |
| 5,458,625 A | 10/1995 | Kendall |
| 5,484,400 A | 1/1996 | Edwards et al. |
| 5,484,401 A | 1/1996 | Rodriguez et al. |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,546,940 A | 8/1996 | Panescu et al. |
| 5,562,720 A | 10/1996 | Stern et al. |
| 5,575,811 A | 11/1996 | Reid et al. |
| D376,652 S | 12/1996 | Hunt et al. |
| 5,582,588 A | 12/1996 | Sakurai et al. |
| 5,586,982 A | 12/1996 | Abela |
| 5,588,424 A | 12/1996 | Insler et al. |
| 5,588,960 A | 12/1996 | Edwards et al. |

(56) References Cited

U.S. PATENT DOCUMENTS

| | | |
|---|---|---|
| 5,599,294 A | 2/1997 | Edwards et al. |
| 5,599,311 A | 2/1997 | Raulerson |
| 5,616,126 A | 4/1997 | Malekmehr et al. |
| 5,620,479 A | 4/1997 | Diederich |
| 5,626,146 A | 5/1997 | Barber et al. |
| D380,272 S | 6/1997 | Partika et al. |
| 5,634,899 A | 6/1997 | Shapland et al. |
| 5,643,197 A | 7/1997 | Brucker et al. |
| 5,645,855 A | 7/1997 | Lorenz |
| 5,672,173 A | 9/1997 | Gough et al. |
| 5,674,267 A | 10/1997 | Mir et al. |
| 5,683,384 A | 11/1997 | Gough et al. |
| 5,687,723 A | 11/1997 | Avitall |
| 5,690,620 A | 11/1997 | Knott |
| 5,697,905 A | 12/1997 | d'Ambrosio |
| 5,700,252 A | 12/1997 | Klingenstein |
| 5,702,359 A | 12/1997 | Hofmann et al. |
| 5,718,246 A | 2/1998 | Vona |
| 5,720,921 A | 2/1998 | Meserol |
| 5,735,847 A | 4/1998 | Gough et al. |
| 5,752,939 A | 5/1998 | Makoto |
| 5,778,894 A | 7/1998 | Dorogi et al. |
| 5,782,882 A | 7/1998 | Lerman et al. |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Pearlman |
| 5,810,762 A | 9/1998 | Hofmann |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,865,787 A | 2/1999 | Shapland et al. |
| 5,868,708 A | 2/1999 | Hart et al. |
| 5,873,849 A | 2/1999 | Bernard |
| 5,904,648 A | 5/1999 | Arndt et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,951,546 A | 9/1999 | Lorentzen |
| 5,954,745 A | 9/1999 | Gertler et al. |
| 5,957,919 A | 9/1999 | Laufer |
| 5,957,963 A | 9/1999 | Dobak |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| D430,015 S | 8/2000 | Himbert et al. |
| 6,096,035 A | 8/2000 | Sodhi et al. |
| 6,102,885 A | 8/2000 | Bass |
| 6,106,521 A | 8/2000 | Blewett et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,139,545 A | 10/2000 | Utley et al. |
| 6,150,148 A | 11/2000 | Nanda et al. |
| 6,159,163 A | 12/2000 | Strauss et al. |
| 6,178,354 B1 | 1/2001 | Gibson |
| D437,941 S | 2/2001 | Frattini |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown, III et al. |
| D442,697 S | 5/2001 | Hajianpour |
| 6,233,490 B1 | 5/2001 | Kasevich |
| 6,235,023 B1 | 5/2001 | Lee et al. |
| D443,360 S | 6/2001 | Haberland |
| 6,241,702 B1 | 6/2001 | Lundquist et al. |
| 6,241,725 B1 * | 6/2001 | Cosman ............ A61B 18/1477 600/41 |
| D445,198 S | 7/2001 | Frattini |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky et al. |
| D450,391 S | 11/2001 | Hunt et al. |
| 6,312,428 B1 | 11/2001 | Eggers et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky et al. |
| 6,398,779 B1 | 6/2002 | Buysse et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,428,802 B1 | 8/2002 | Atala |
| 6,443,952 B1 | 9/2002 | Mulier et al. |
| 6,463,331 B1 | 10/2002 | Edwards |
| 6,470,211 B1 | 10/2002 | Ideker et al. |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,500,173 B2 | 12/2002 | Underwood et al. |
| 6,503,248 B1 | 1/2003 | Levine |
| 6,506,189 B1 | 1/2003 | Rittman et al. |
| 6,514,248 B1 | 2/2003 | Eggers et al. |

(56) References Cited

U.S. PATENT DOCUMENTS

| | | |
|---|---|---|
| 6,520,183 B2 | 2/2003 | Amar |
| 6,526,320 B2 | 2/2003 | Mitchell |
| D471,640 S | 3/2003 | McMichael et al. |
| D471,641 S | 3/2003 | McMichael et al. |
| 6,530,922 B2 | 3/2003 | Cosman et al. |
| 6,533,784 B2 | 3/2003 | Truckai et al. |
| 6,537,976 B1 | 3/2003 | Gupta |
| 6,558,378 B2 | 5/2003 | Sherman et al. |
| 6,562,604 B2 | 5/2003 | Rubinsky et al. |
| 6,569,162 B2 | 5/2003 | He |
| 6,575,969 B1 | 6/2003 | Rittman et al. |
| 6,589,161 B2 | 7/2003 | Corcoran |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | Mccormick et al. |
| 6,616,657 B2 | 9/2003 | Simpson et al. |
| 6,627,421 B1 | 9/2003 | Unger et al. |
| D480,816 S | 10/2003 | McMichael et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,689,096 B1 | 2/2004 | Loubens et al. |
| 6,692,493 B2 | 2/2004 | Mcgovern et al. |
| 6,694,979 B2 | 2/2004 | Deem et al. |
| 6,694,984 B2 | 2/2004 | Habib |
| 6,695,861 B1 | 2/2004 | Rosenberg et al. |
| 6,697,669 B2 | 2/2004 | Dev et al. |
| 6,697,670 B2 | 2/2004 | Chomenky et al. |
| 6,702,808 B1 | 3/2004 | Kreindel |
| 6,712,811 B2 | 3/2004 | Underwood et al. |
| D489,973 S | 5/2004 | Root et al. |
| 6,753,171 B2 | 6/2004 | Karube et al. |
| 6,761,716 B2 | 7/2004 | Kadhiresan et al. |
| D495,807 S | 9/2004 | Agbodoe et al. |
| 6,795,728 B2 | 9/2004 | Chornenky et al. |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Alferness et al. |
| 6,865,416 B2 | 3/2005 | Dev et al. |
| 6,881,213 B2 | 4/2005 | Ryan et al. |
| 6,892,099 B2 | 5/2005 | Jaafar et al. |
| 6,895,267 B2 | 5/2005 | Panescu et al. |
| 6,905,480 B2 | 6/2005 | McGuckin et al. |
| 6,912,417 B1 | 6/2005 | Bernard et al. |
| 6,927,049 B2 | 8/2005 | Rubinsky et al. |
| 6,941,950 B2 | 9/2005 | Wilson et al. |
| 6,942,681 B2 | 9/2005 | Johnson |
| 6,958,062 B1 | 10/2005 | Gough et al. |
| 6,960,189 B2 | 11/2005 | Bates et al. |
| 6,962,587 B2 | 11/2005 | Johnson et al. |
| 6,972,013 B1 | 12/2005 | Zhang et al. |
| 6,972,014 B2 | 12/2005 | Eum et al. |
| 6,989,010 B2 | 1/2006 | Francischelli et al. |
| 6,994,689 B1 | 2/2006 | Zadno-Azizi et al. |
| 6,994,706 B2 | 2/2006 | Chornenky et al. |
| 7,011,094 B2 | 3/2006 | Rapacki et al. |
| 7,012,061 B1 | 3/2006 | Reiss et al. |
| 7,027,869 B2 | 4/2006 | Danek et al. |
| 7,036,510 B2 | 5/2006 | Zgoda et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,087,040 B2 | 8/2006 | McGuckin et al. |
| 7,097,612 B2 | 8/2006 | Bertolero et al. |
| 7,100,616 B2 | 9/2006 | Springmeyer |
| 7,113,821 B1 | 9/2006 | Sun et al. |
| 7,130,697 B2 | 10/2006 | Chornenky et al. |
| 7,211,083 B2 | 5/2007 | Chornenky et al. |
| 7,232,437 B2 | 6/2007 | Berman et al. |
| 7,250,048 B2 | 7/2007 | Francischelli et al. |
| D549,332 S | 8/2007 | Matsumoto et al. |
| 7,257,450 B2 | 8/2007 | Auth et al. |
| 7,264,002 B2 | 9/2007 | Danek et al. |
| 7,267,676 B2 | 9/2007 | Chornenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | Torre et al. |
| 7,344,533 B2 | 3/2008 | Pearson et al. |
| D565,743 S | 4/2008 | Phillips et al. |
| D571,478 S | 6/2008 | Horacek |
| 7,387,626 B2 | 6/2008 | Edwards et al. |
| 7,399,747 B1 | 7/2008 | Clair et al. |
| D575,399 S | 8/2008 | Matsumoto et al. |
| D575,402 S | 8/2008 | Sandor |
| 7,419,487 B2 | 9/2008 | Johnson et al. |
| 7,434,578 B2 | 10/2008 | Dillard et al. |
| 7,449,019 B2 | 11/2008 | Uchida et al. |
| 7,451,765 B2 | 11/2008 | Adler |
| 7,455,675 B2 | 11/2008 | Schur et al. |
| 7,476,203 B2 | 1/2009 | DeVore et al. |
| 7,520,877 B2 | 4/2009 | Lee et al. |
| 7,533,671 B2 | 5/2009 | Gonzalez et al. |
| D595,422 S | 6/2009 | Mustapha |
| 7,544,301 B2 | 6/2009 | Shah et al. |
| 7,549,984 B2 | 6/2009 | Mathis |
| 7,565,208 B2 | 7/2009 | Harris et al. |
| 7,571,729 B2 | 8/2009 | Saadat et al. |
| 7,632,291 B2 | 12/2009 | Stephens et al. |
| 7,655,004 B2 | 2/2010 | Long |
| 7,674,249 B2 | 3/2010 | Ivorra et al. |
| 7,680,543 B2 | 3/2010 | Azure |
| D613,418 S | 4/2010 | Ryan et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,765,010 B2 | 7/2010 | Chornenky et al. |
| 7,771,401 B2 | 8/2010 | Hekmat et al. |
| RE42,016 E | 12/2010 | Chornenky et al. |
| D630,321 S | 1/2011 | Hamilton |
| D631,154 S | 1/2011 | Hamilton |
| RE42,277 E | 4/2011 | Jaafar et al. |
| 7,918,852 B2 | 4/2011 | Tullis et al. |
| 7,937,143 B2 * | 5/2011 | Demarais ............ A61N 1/0514 604/21 |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chornenky et al. |
| D647,628 S | 10/2011 | Helfteren |
| 8,048,067 B2 | 11/2011 | Davalos et al. |
| RE43,009 E | 12/2011 | Chornenky et al. |
| 8,109,926 B2 | 2/2012 | Azure |
| 8,114,070 B2 | 2/2012 | Rubinsky et al. |
| 8,162,918 B2 | 4/2012 | Ivorra et al. |
| 8,187,269 B2 | 5/2012 | Shadduck et al. |
| 8,221,411 B2 | 7/2012 | Francischelli et al. |
| 8,231,603 B2 | 7/2012 | Hobbs et al. |
| 8,240,468 B2 | 8/2012 | Wilkinson et al. |
| 8,251,986 B2 | 8/2012 | Chornenky et al. |
| 8,267,927 B2 | 9/2012 | Dalal et al. |
| 8,267,936 B2 | 9/2012 | Hushka et al. |
| 8,282,631 B2 | 10/2012 | Davalos et al. |
| 8,298,222 B2 | 10/2012 | Rubinsky et al. |
| 8,348,921 B2 | 1/2013 | Ivorra et al. |
| D677,798 S | 3/2013 | Hart et al. |
| 8,425,455 B2 | 4/2013 | Nentwick |
| 8,425,505 B2 | 4/2013 | Long |
| 8,454,594 B2 | 6/2013 | Demarais et al. |
| 8,465,484 B2 * | 6/2013 | Davalos ............... A61N 1/327 128/898 |
| 8,511,317 B2 | 8/2013 | Thapliyal et al. |
| 8,518,031 B2 | 8/2013 | Boyden et al. |
| 8,562,588 B2 | 10/2013 | Hobbs et al. |
| 8,603,087 B2 | 12/2013 | Rubinsky et al. |

(56) References Cited

U.S. PATENT DOCUMENTS

| | | |
|---|---|---|
| 8,632,534 B2 | 1/2014 | Pearson et al. |
| 8,634,929 B2 | 1/2014 | Chornenky et al. |
| 8,647,338 B2 | 2/2014 | Chornenky et al. |
| 8,715,276 B2 | 5/2014 | Thompson et al. |
| 8,753,335 B2 | 6/2014 | Moshe et al. |
| 8,814,860 B2 | 8/2014 | Davalos et al. |
| 8,835,166 B2 | 9/2014 | Phillips et al. |
| 8,845,635 B2 | 9/2014 | Daniel et al. |
| 8,880,195 B2 | 11/2014 | Azure |
| 8,903,488 B2 | 12/2014 | Callas et al. |
| 8,906,006 B2 | 12/2014 | Chornenky et al. |
| 8,926,606 B2 | 1/2015 | Davalos et al. |
| 8,958,888 B2 | 2/2015 | Chornenky et al. |
| 8,968,542 B2 | 3/2015 | Davalos et al. |
| 8,992,517 B2 | 3/2015 | Davalos et al. |
| 9,005,189 B2 | 4/2015 | Davalos et al. |
| 9,078,665 B2 | 7/2015 | Moss et al. |
| 9,149,331 B2 | 10/2015 | Deem et al. |
| 9,173,704 B2 | 11/2015 | Hobbs et al. |
| 9,198,733 B2 | 12/2015 | Neal, II et al. |
| 9,283,051 B2 * | 3/2016 | Garcia .................. C12N 13/00 |
| 9,598,691 B2 | 3/2017 | Davalos |
| 9,867,652 B2 | 1/2018 | Sano et al. |
| 2001/0039393 A1 | 11/2001 | Mori et al. |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach et al. |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077676 A1 | 6/2002 | Schroeppel et al. |
| 2002/0082543 A1 | 6/2002 | Park et al. |
| 2002/0099323 A1 | 7/2002 | Dev et al. |
| 2002/0111615 A1 | 8/2002 | Cosman et al. |
| 2002/0112729 A1 | 8/2002 | DeVore et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards et al. |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Smith |
| 2003/0009110 A1 | 1/2003 | Tu et al. |
| 2003/0016168 A1 | 1/2003 | Jandrell |
| 2003/0055220 A1 | 3/2003 | Legrain |
| 2003/0055420 A1 | 3/2003 | Kadhiresan et al. |
| 2003/0059945 A1 | 3/2003 | Dzekunov et al. |
| 2003/0060856 A1 | 3/2003 | Chornenky et al. |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Atala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky et al. |
| 2003/0154988 A1 | 8/2003 | DeVore et al. |
| 2003/0159700 A1 | 8/2003 | Laufer et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | DeVore |
| 2003/0195406 A1 | 10/2003 | Jenkins et al. |
| 2003/0199050 A1 | 10/2003 | Mangano et al. |
| 2003/0208200 A1 | 11/2003 | Palanker et al. |
| 2003/0208236 A1 | 11/2003 | Heil et al. |
| 2003/0212394 A1 | 11/2003 | Pearson et al. |
| 2003/0212412 A1 | 11/2003 | Dillard et al. |
| 2003/0225360 A1 | 12/2003 | Eppstein et al. |
| 2003/0228344 A1 | 12/2003 | Fields et al. |
| 2004/0009459 A1 | 1/2004 | Anderson et al. |
| 2004/0019371 A1 | 1/2004 | Jaafar et al. |
| 2004/0055606 A1 | 3/2004 | Hendricksen et al. |
| 2004/0059328 A1 | 3/2004 | Daniel et al. |
| 2004/0059389 A1 | 3/2004 | Chornenky et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0138715 A1 | 7/2004 | Groeningen et al. |
| 2004/0146877 A1 | 7/2004 | Diss et al. |
| 2004/0153057 A1 | 8/2004 | Davison |
| 2004/0176855 A1 | 9/2004 | Badylak |
| 2004/0193097 A1 | 9/2004 | Hofmann et al. |
| 2004/0199159 A1 | 10/2004 | Lee et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0230187 A1 | 11/2004 | Lee et al. |
| 2004/0236376 A1 | 11/2004 | Miklavcic et al. |
| 2004/0243107 A1 | 12/2004 | Macoviak et al. |
| 2004/0267189 A1 | 12/2004 | Mavor et al. |
| 2004/0267340 A1 | 12/2004 | Cioanta et al. |
| 2005/0010209 A1 | 1/2005 | Lee et al. |
| 2005/0010259 A1 | 1/2005 | Gerber |
| 2005/0013870 A1 | 1/2005 | Freyman et al. |
| 2005/0020965 A1 | 1/2005 | Rioux et al. |
| 2005/0043726 A1 | 2/2005 | Mchale et al. |
| 2005/0049541 A1 | 3/2005 | Behar et al. |
| 2005/0061322 A1 | 3/2005 | Freitag |
| 2005/0066974 A1 | 3/2005 | Fields et al. |
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0197619 A1 | 9/2005 | Rule et al. |
| 2005/0261672 A1 | 11/2005 | Deem et al. |
| 2005/0267407 A1 | 12/2005 | Goldman |
| 2005/0282284 A1 | 12/2005 | Rubinsky et al. |
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski et al. |
| 2006/0004400 A1 | 1/2006 | McGurk et al. |
| 2006/0009748 A1 | 1/2006 | Mathis |
| 2006/0015147 A1 | 1/2006 | Persson et al. |
| 2006/0020347 A1 | 1/2006 | Barrett et al. |
| 2006/0024359 A1 | 2/2006 | Walker et al. |
| 2006/0025760 A1 | 2/2006 | Podhajsky |
| 2006/0074413 A1 | 4/2006 | Behzadian |
| 2006/0079838 A1 | 4/2006 | Walker et al. |
| 2006/0079845 A1 | 4/2006 | Howard et al. |
| 2006/0079883 A1 | 4/2006 | Elmouelhi et al. |
| 2006/0085054 A1 | 4/2006 | Zikorus et al. |
| 2006/0089635 A1 | 4/2006 | Young et al. |
| 2006/0121610 A1 | 6/2006 | Rubinsky et al. |
| 2006/0142801 A1 | 6/2006 | Demarais et al. |
| 2006/0149123 A1 | 7/2006 | Vidlund et al. |
| 2006/0173490 A1 | 8/2006 | Lafontaine et al. |
| 2006/0182684 A1 | 8/2006 | Beliveau |
| 2006/0195146 A1 | 8/2006 | Tracey et al. |
| 2006/0212032 A1 | 9/2006 | Daniel et al. |
| 2006/0212078 A1 | 9/2006 | Demarais et al. |
| 2006/0217703 A1 | 9/2006 | Chornenky et al. |

(56) References Cited

U.S. PATENT DOCUMENTS

| | | |
|---|---|---|
| 2006/0224188 A1 | 10/2006 | Libbus et al. |
| 2006/0235474 A1 | 10/2006 | Demarais |
| 2006/0247619 A1 | 11/2006 | Kaplan et al. |
| 2006/0264752 A1 | 11/2006 | Rubinsky et al. |
| 2006/0264807 A1 | 11/2006 | Westersten et al. |
| 2006/0269531 A1 | 11/2006 | Beebe et al. |
| 2006/0276710 A1 | 12/2006 | Krishnan |
| 2006/0283462 A1 | 12/2006 | Fields et al. |
| 2006/0293713 A1* | 12/2006 | Rubinsky ............ A61N 1/0412 607/2 |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016183 A1 | 1/2007 | Lee et al. |
| 2007/0016185 A1 | 1/2007 | Tullis et al. |
| 2007/0021803 A1 | 1/2007 | Deem et al. |
| 2007/0025919 A1 | 2/2007 | Deem et al. |
| 2007/0043345 A1* | 2/2007 | Davalos ............... A61B 18/12 606/32 |
| 2007/0060989 A1 | 3/2007 | Deem et al. |
| 2007/0078391 A1 | 4/2007 | Wortley et al. |
| 2007/0088347 A1 | 4/2007 | Young et al. |
| 2007/0093789 A1 | 4/2007 | Smith |
| 2007/0096048 A1 | 5/2007 | Clerc |
| 2007/0118069 A1* | 5/2007 | Persson ............... A61N 1/044 604/20 |
| 2007/0129711 A1 | 6/2007 | Altshuler et al. |
| 2007/0129760 A1 | 6/2007 | Demarais et al. |
| 2007/0156135 A1 | 7/2007 | Rubinsky et al. |
| 2007/0191889 A1 | 8/2007 | Lang |
| 2007/0203486 A1 | 8/2007 | Young |
| 2007/0230757 A1 | 10/2007 | Trachtenberg et al. |
| 2007/0239099 A1 | 10/2007 | Goldfarb et al. |
| 2007/0244521 A1 | 10/2007 | Bornzin et al. |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0015571 A1 | 1/2008 | Rubinsky et al. |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0071262 A1 | 3/2008 | Azure |
| 2008/0097139 A1 | 4/2008 | Clerc et al. |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0125772 A1 | 5/2008 | Stone et al. |
| 2008/0132826 A1 | 6/2008 | Shadduck et al. |
| 2008/0132884 A1 | 6/2008 | Rubinsky et al. |
| 2008/0132885 A1 | 6/2008 | Rubinsky et al. |
| 2008/0140064 A1 | 6/2008 | Vegesna |
| 2008/0146934 A1 | 6/2008 | Czygan et al. |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0190434 A1 | 8/2008 | Wai |
| 2008/0200911 A1 | 8/2008 | Long |
| 2008/0200912 A1 | 8/2008 | Long |
| 2008/0208052 A1 | 8/2008 | LePivert et al. |
| 2008/0210243 A1 | 9/2008 | Clayton et al. |
| 2008/0214986 A1 | 9/2008 | Ivorra et al. |
| 2008/0236593 A1 | 10/2008 | Nelson et al. |
| 2008/0249503 A1 | 10/2008 | Fields et al. |
| 2008/0262489 A1 | 10/2008 | Steinke |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0281319 A1 | 11/2008 | Paul et al. |
| 2008/0283065 A1 | 11/2008 | Chang et al. |
| 2008/0288038 A1 | 11/2008 | Paul et al. |
| 2008/0300589 A1 | 12/2008 | Paul et al. |
| 2008/0306427 A1 | 12/2008 | Bailey |
| 2008/0312599 A1 | 12/2008 | Rosenberg |
| 2009/0018206 A1 | 1/2009 | Barkan et al. |
| 2009/0024075 A1 | 1/2009 | Schroeppel et al. |
| 2009/0029407 A1 | 1/2009 | Gazit et al. |
| 2009/0038752 A1 | 2/2009 | Weng et al. |
| 2009/0062788 A1 | 3/2009 | Long et al. |
| 2009/0062792 A1 | 3/2009 | Vakharia et al. |
| 2009/0081272 A1 | 3/2009 | Clarke et al. |
| 2009/0105703 A1 | 4/2009 | Shadduck |
| 2009/0114226 A1 | 5/2009 | Deem et al. |
| 2009/0125009 A1 | 5/2009 | Zikorus et al. |
| 2009/0138014 A1 | 5/2009 | Bonutti |
| 2009/0143705 A1 | 6/2009 | Danek et al. |
| 2009/0157166 A1 | 6/2009 | Singhal et al. |
| 2009/0163904 A1 | 6/2009 | Miller et al. |
| 2009/0171280 A1 | 7/2009 | Samuel et al. |
| 2009/0177111 A1 | 7/2009 | Miller et al. |
| 2009/0186850 A1 | 7/2009 | Kiribayashi et al. |
| 2009/0192508 A1 | 7/2009 | Laufer et al. |
| 2009/0198231 A1 | 8/2009 | Esser et al. |
| 2009/0228001 A1 | 9/2009 | Pacey |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0275827 A1 | 11/2009 | Aiken et al. |
| 2009/0281477 A1 | 11/2009 | Mikus et al. |
| 2009/0292342 A1 | 11/2009 | Rubinsky et al. |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318905 A1 | 12/2009 | Bhargav et al. |
| 2009/0326436 A1 | 12/2009 | Rubinsky et al. |
| 2009/0326570 A1 | 12/2009 | Brown |
| 2010/0004623 A1 | 1/2010 | Hamilton et al. |
| 2010/0023004 A1 | 1/2010 | Francischelli et al. |
| 2010/0030211 A1 | 2/2010 | Davalos et al. |
| 2010/0049190 A1 | 2/2010 | Long et al. |
| 2010/0057074 A1 | 3/2010 | Roman et al. |
| 2010/0069921 A1 | 3/2010 | Miller et al. |
| 2010/0087813 A1 | 4/2010 | Long |
| 2010/0130975 A1 | 5/2010 | Long |
| 2010/0152725 A1 | 6/2010 | Pearson et al. |
| 2010/0160850 A1 | 6/2010 | Ivorra et al. |
| 2010/0168735 A1 | 7/2010 | Deno et al. |
| 2010/0174282 A1 | 7/2010 | Demarais et al. |
| 2010/0179530 A1 | 7/2010 | Long et al. |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0222677 A1 | 9/2010 | Placek et al. |
| 2010/0228234 A1 | 9/2010 | Hyde et al. |
| 2010/0228247 A1 | 9/2010 | Paul et al. |
| 2010/0241117 A1 | 9/2010 | Paul et al. |
| 2010/0249771 A1 | 9/2010 | Pearson et al. |
| 2010/0250209 A1* | 9/2010 | Pearson ............ A61B 18/1206 703/2 |
| 2010/0255795 A1 | 10/2010 | Rubinsky et al. |
| 2010/0256628 A1 | 10/2010 | Pearson et al. |
| 2010/0256630 A1 | 10/2010 | Hamilton, Jr. et al. |
| 2010/0261994 A1 | 10/2010 | Davalos et al. |
| 2010/0286690 A1 | 11/2010 | Paul et al. |
| 2010/0298823 A1 | 11/2010 | Cao et al. |
| 2010/0331758 A1 | 12/2010 | Davalos et al. |
| 2011/0017207 A1 | 1/2011 | Hendricksen et al. |
| 2011/0034209 A1 | 2/2011 | Rubinsky et al. |
| 2011/0064671 A1 | 3/2011 | Bynoe |
| 2011/0106221 A1 | 5/2011 | Neal, II et al. |
| 2011/0112531 A1 | 5/2011 | Landis et al. |
| 2011/0118727 A1 | 5/2011 | Fish et al. |
| 2011/0118732 A1 | 5/2011 | Rubinsky et al. |
| 2011/0130834 A1 | 6/2011 | Wilson et al. |
| 2011/0144524 A1 | 6/2011 | Fish et al. |
| 2011/0144635 A1 | 6/2011 | Harper et al. |
| 2011/0144657 A1 | 6/2011 | Fish et al. |
| 2011/0152678 A1 | 6/2011 | Aljuri et al. |
| 2011/0202053 A1 | 8/2011 | Moss et al. |

(56) References Cited

U.S. PATENT DOCUMENTS

| | | |
|---|---|---|
| 2011/0217730 A1 | 9/2011 | Gazit et al. |
| 2011/0251607 A1 | 10/2011 | Kruecker et al. |
| 2011/0301587 A1 | 12/2011 | Deem et al. |
| 2012/0034131 A1 | 2/2012 | Rubinsky et al. |
| 2012/0059255 A1 | 3/2012 | Paul et al. |
| 2012/0071872 A1 | 3/2012 | Rubinsky et al. |
| 2012/0071874 A1 | 3/2012 | Davalos et al. |
| 2012/0085649 A1 | 4/2012 | Sano et al. |
| 2012/0089009 A1 | 4/2012 | Omary et al. |
| 2012/0095459 A1 | 4/2012 | Callas et al. |
| 2012/0109122 A1 | 5/2012 | Arena et al. |
| 2012/0130289 A1 | 5/2012 | Demarais et al. |
| 2012/0150172 A1 | 6/2012 | Ortiz et al. |
| 2012/0165813 A1 | 6/2012 | Lee et al. |
| 2012/0179091 A1 | 7/2012 | Ivorra et al. |
| 2012/0226218 A1 | 9/2012 | Phillips et al. |
| 2012/0226271 A1 | 9/2012 | Callas et al. |
| 2012/0265186 A1 | 10/2012 | Burger et al. |
| 2012/0277741 A1 | 11/2012 | Davalos et al. |
| 2012/0303020 A1 | 11/2012 | Chornenky et al. |
| 2012/0310236 A1 | 12/2012 | Placek et al. |
| 2013/0090646 A1 | 4/2013 | Moss et al. |
| 2013/0108667 A1 | 5/2013 | Soikum et al. |
| 2013/0110106 A1 | 5/2013 | Richardson |
| 2013/0184702 A1 | 7/2013 | Neal, II et al. |
| 2013/0196441 A1 | 8/2013 | Rubinsky et al. |
| 2013/0197425 A1 | 8/2013 | Golberg et al. |
| 2013/0202766 A1 | 8/2013 | Rubinsky et al. |
| 2013/0218157 A1 | 8/2013 | Callas et al. |
| 2013/0253415 A1 | 9/2013 | Sano et al. |
| 2013/0281968 A1 | 10/2013 | Davalos et al. |
| 2013/0345697 A1 | 12/2013 | Garcia et al. |
| 2013/0345779 A1 | 12/2013 | Maor et al. |
| 2014/0039489 A1 | 2/2014 | Davalos et al. |
| 2014/0046322 A1 | 2/2014 | Callas et al. |
| 2014/0081255 A1 | 3/2014 | Johnson et al. |
| 2014/0088578 A1 | 3/2014 | Rubinsky et al. |
| 2014/0121663 A1 | 5/2014 | Pearson et al. |
| 2014/0163551 A1 | 6/2014 | Maor et al. |
| 2014/0207133 A1 | 7/2014 | Model et al. |
| 2014/0296844 A1 | 10/2014 | Kevin et al. |
| 2014/0309579 A1 | 10/2014 | Rubinsky et al. |
| 2014/0378964 A1 | 12/2014 | Pearson |
| 2015/0088120 A1 | 3/2015 | Garcia et al. |
| 2015/0088220 A1 | 3/2015 | Callas et al. |
| 2015/0112333 A1 | 4/2015 | Chorenky et al. |
| 2015/0126922 A1 | 5/2015 | Willis |
| 2015/0164584 A1 | 6/2015 | Davalos et al. |
| 2015/0173824 A1 | 6/2015 | Davalos et al. |
| 2015/0201996 A1 | 7/2015 | Rubinsky et al. |
| 2015/0265349 A1 | 9/2015 | Moss et al. |
| 2015/0289923 A1 | 10/2015 | Davalos et al. |
| 2015/0320488 A1 | 11/2015 | Moshe et al. |
| 2015/0327944 A1 | 11/2015 | Davalos et al. |
| 2016/0022957 A1 | 1/2016 | Hobbs et al. |
| 2016/0066977 A1 | 3/2016 | Neal et al. |
| 2016/0074114 A1 | 3/2016 | Pearson et al. |
| 2016/0113708 A1 | 4/2016 | Moss et al. |
| 2016/0143698 A1 | 5/2016 | Garcia et al. |
| 2016/0235470 A1 | 8/2016 | Callas et al. |
| 2016/0287313 A1 | 10/2016 | Rubinsky et al. |
| 2016/0287314 A1 | 10/2016 | Arena et al. |
| 2016/0338761 A1 | 11/2016 | Chornenky et al. |
| 2016/0354142 A1 | 12/2016 | Pearson et al. |
| 2017/0035501 A1 | 2/2017 | Chornenky et al. |
| 2017/0189579 A1 | 7/2017 | Davalos |
| 2017/0209620 A1 | 7/2017 | Davalos et al. |
| 2017/0266438 A1 | 9/2017 | Sano |
| 2017/0360326 A1 | 12/2017 | Davalos |
| 2018/0125565 A1 | 5/2018 | Sano et al. |
| 2018/0161086 A1 | 6/2018 | Davalos et al. |

FOREIGN PATENT DOCUMENTS

| | | |
|---|---|---|
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| DE | 863111ltr | 1/1953 |
| DE | 4000893tr | 7/1991 |
| DE | 60038026 | 2/2009 |
| EP | 0218275 A1 | 4/1987 |
| EP | 0339501 A2 | 11/1989 |
| EP | 0378132 A | 7/1990 |
| EP | 0528891 B1 | 3/1993 |
| EP | 0533511 A1 | 3/1993 |
| EP | 0998235 A1 | 5/2000 |
| EP | 1196550 A2 | 4/2002 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1796568 A1 | 6/2007 |
| EP | 1207797 B1 | 2/2008 |
| EP | 1406685 B1 | 6/2008 |
| EP | 1424970 B1 | 12/2008 |
| EP | 2381829 A1 | 11/2011 |
| EP | 2413833 A1 | 2/2012 |
| EP | 1791485 B1 | 12/2014 |
| EP | 2373241 B1 | 1/2015 |
| EP | 1962710 B1 | 8/2015 |
| EP | 1962708 B1 | 9/2015 |
| EP | 1962945 B1 | 4/2016 |
| ES | 2300272 | 6/2008 |
| ES | 2315493 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2008508946 A | 3/2008 |
| JP | 4252316 B2 | 4/2009 |
| JP | 2009518130 A | 5/2009 |
| JP | 2009518150 A | 5/2009 |
| JP | 2009518151 A | 5/2009 |
| JP | 2012510332 A | 5/2012 |
| JP | 2012521863 A | 9/2012 |
| KR | 101034682 A | 5/2011 |
| WO | 9104014 A | 4/1991 |
| WO | 9634571 | 11/1996 |
| WO | 9639531 A | 12/1996 |
| WO | 9810745 | 3/1998 |
| WO | 9814238 A | 4/1998 |
| WO | 9901076 | 1/1999 |
| WO | 9904710 | 2/1999 |
| WO | 0020554 A | 4/2000 |
| WO | 0107583 A | 2/2001 |
| WO | 0107584 A | 2/2001 |
| WO | 0107585 A | 2/2001 |
| WO | 0110319 A | 2/2001 |

(56) References Cited

FOREIGN PATENT DOCUMENTS

| | | |
|---|---|---|
| WO | 0148153 A | 7/2001 |
| WO | 2001048153 A1 | 7/2001 |
| WO | 0170114 A1 | 9/2001 |
| WO | 0181533 A | 11/2001 |
| WO | 02078527 A | 10/2002 |
| WO | 02089686 A | 11/2002 |
| WO | 02100459 A | 12/2002 |
| WO | 2003020144 A1 | 3/2003 |
| WO | 2003047684 A2 | 6/2003 |
| WO | 03099382 A | 12/2003 |
| WO | 2004037341 A2 | 5/2004 |
| WO | 2004080347 A2 | 9/2004 |
| WO | 2005065284 A | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007123690 A2 | 11/2007 |
| WO | 2007137303 A | 11/2007 |
| WO | 2008063195 A1 | 5/2008 |
| WO | 2009046176 A1 | 4/2009 |
| WO | 2009134876 A | 11/2009 |
| WO | 2009135070 A1 | 11/2009 |
| WO | 2009137800 A2 | 11/2009 |
| WO | 2010064154 A1 | 6/2010 |
| WO | 2010117806 A1 | 10/2010 |
| WO | 2010118387 A | 10/2010 |
| WO | 2010132472 A1 | 11/2010 |
| WO | 2010151277 A | 12/2010 |
| WO | 2011047387 A | 4/2011 |
| WO | 2011062653 A1 | 5/2011 |
| WO | 2011072221 A1 | 6/2011 |
| WO | 2012051433 A2 | 4/2012 |
| WO | 2012071526 A | 5/2012 |
| WO | 2012088149 A | 6/2012 |
| WO | 2015175570 A1 | 11/2015 |
| WO | 2016100325 A1 | 6/2016 |
| WO | 2016164930 A1 | 10/2016 |

OTHER PUBLICATIONS

Okino, et al., Effects of High-Voltage Electrical Impulse and an Anticancer Drug on In Vivo Growing Tumors, Japanese Journal of Cancer Research, vol. 78, pp. 1319-1321, 1987.
Onik, et al., Sonographic Monitoring of Hepatic Cryosurgery in an Experimental Animal Model, AJR American J. of Roentgenology, vol. 144, pp. 1043-1047, May 1985.
Onik, et al., Ultrasonic Characteristics of Frozen Liver, Cryobiology, vol. 21, pp. 321-328, 1984.
Organ, L.W., Electrophysiological principles of radiofrequency lesion making, Apply. Neurophysiol., 1976. 39: p. 69-76.
Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.
Pavselj, N. et al. The course of tissue permeabilization studied on a mathematical model of a subcutaneous tumor in small animals. IEEE Trans Biomed Eng 52, 1373-1381 (2005).
PCT International Preliminary Report on Patentability of Corresponding International Application No. PCT/2011/062067, dated May 28, 2013.
PCT International Preliminary Report on Patentability of Corresponding International Application No. PCT/2011/066239, dated Jun. 25, 2013.

PCT International Search Report (dated Aug. 2, 2011), Written Opinion (dated Aug. 2, 2011), and International Preliminary Report on Patentability (dated Apr. 17, 2012) of PCT/US10/53077.
PCT International Search Report (dated Aug. 22, 2012), and Written Opinion (dated Aug. 22, 2012) of PCT/US11/66239.
PCT International Search Report (dated Aug. 26, 2005), Written Opinion (dated Aug. 26, 2005), and International Preliminary Report on Patentability (dated Jun. 26, 2006) of PCT/US2004/043477.
PCT International Search Report (dated Jan. 19, 2010), Written Opinion (dated Jan. 19, 2010), and International Preliminary Report on Patentability (dated Jan. 4, 2010) of PCT/US09/62806, 15 pgs.
PCT International Search Report (dated Jul. 15, 2010), Written Opinion (dated Jul. 15, 2010), and International Preliminary Report on Patentability (dated Oct. 11, 2011) from PCT/US2010/030629.
PCT International Search Report (dated Jul. 9, 2009), Written Opinion (dated Jul. 9, 2009), and International Preliminary Report on Patentability (dated Nov. 2, 2010) of PCT/US2009/042100.
PCT International Search Report and Written Opinion (dated Jul. 25, 2012) of PCT/US2011/062067.
PCT International Search Report, 4 pgs, (dated Jul. 30, 2010), Written Opinion, 7 pgs, (dated Jul. 30, 2010), and International Preliminary Report on Patentability, 8 pgs, (dated Oct. 4, 2011) from PCT/US2010/029243.
Phillips, M., Maor, E. & Rubinsky, B. Non-Thermal Irreversible Electroporation for Tissue Decellularization. J. Biomech. Eng, doi:10.1115/1.4001882 (2010).
Piñero, et al., Apoptotic and Necrotic Cell Death Are Both Induced by Electroporation in HL60 Human Promyeloid Leukaemia Cells, Apoptosis, vol. 2, No. 3, 330-336, Aug. 1997.
Precision Office Tuna System, When Patient Satisfaction is Your Goal, VidaMed 2001.
Rajagopal, V. and S.G. Rockson, Coronary restenosis: a review of mechanisms and management, The American Journal of Medicine, 2003, 115(7): p. 547-553.
Rols, M.P., et al., Highly Efficient Transfection of Mammalian Cells by Electric Field Pulses: Application to Large Volumes of Cell Culture by Using a Flow System, Eur. J. Biochem. 1992, 206, pp. 115-121.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Rubinsky, B., et al., "Irreversible Electroporation: A New Ablation Modality—Clinical Implications" Technol. Cancer Res. Treatment 6(1), 37-48 (2007).
Salford, L.G., et al. "A new brain tumour therapy combining bleomycin with in vivo electropermeabilization", Biochem. Biophys. Res. Commun., 194(2): 938-943 (1993).
Sano, M. B., et al., "Towards the creation of decellularized organ constructs using irreversible electroporation and active mechanical perfusion", Biomedical Engineering Online, Biomed Central LTD, London, GB, vol. 9, No. 1, Dec. 10, 2010, p. 83.
Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.
Sel, D. et al. Sequential finite element model of tissue electropermeabilization. IEEE Transactions on Biomedical Engineering 52, 816-827, doi:10.1109/tbme.2005.845212 (2005).
Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Sersa, et al., Reduced Blood Flow and Oxygenation in SA-1 Tumours after Electrochemotherapy with Cisplatin, British Journal of Cancer, 87, 1047-1054, 2002.
Sersa, et al., Tumour Blood Flow Modifying Effects of Electrochemotherapy: a Potential Vascular Targeted Mechanism, Radiol. Oncol., 37(1): 43-8, 2003.

(56) References Cited

OTHER PUBLICATIONS

Sharma, A., et al., "Review on Thermal Energy Storage with Phase Change Materials and Applications", Renewable Sustainable Energy Rev. 13(2), 318-345 (2009).
Sharma, et al., Poloxamer 188 Decreases Susceptibility of Artificial Lipid Membranes to Electroporation, Biophysical Journal, vol. 71, No. 6, pp. 3229-3241, Dec. 1996.
Shiina, S., et al, Percutaneous ethanol injection therapy for hepatocellular carcinoma: results in 146 patients. AJR, 1993, 160: p. 1023-8.
Tekle, Ephrem, R. Dean Astumian, and P. Boon Chock, Electroporation by using bipolar oscillating electric field: An improved method for DNA transfection of NIH 3T3 cells, Proc. Natl. Acad. Sci., vol. 88, pp. 4230-4234, May 1991, Biochemistry.
Thompson, et al., To determine whether the temperature of 2% lignocaine gel affects the initial discomfort which may be associated with its instillation into the male urethra, BJU International (1999), 84, 1035-1037.
Thomson, K. R., et al., "Investigation of the Safety of Irreversible Electroporation in Humans" J. Vascular Int. Radiol. 22 (5), 611-621 (2011).
Vidamed, Inc., Transurethral Needle Ablation (TUNA): Highlights from Worldwide Clinical Studies, Vidamed's Office TUNA System, 2001.
Weaver, Electroporation: A General Phenomenon for Manipulating Cells and Tissues, Journal of Cellular Biochemistry, 51: 426-435, 1993.
Weaver, et al., Theory of Electroporation: A Review, Bioelectrochemistry and Bioenergetics, vol. 41, pp. 136-160, 1996.
Weaver, J. C., Electroporation of biological membranes from multicellular to nano scales, IEEE Trns. Dielectr. Electr. Insul. 10, 754-768 (2003).
Weisstein: Cassini Ovals. From MathWorld—A. Wolfram Web Resource; Apr. 30, 2010; http://mathworld.wolfram.com/ (updated May 18, 2011).
Zimmermann, et al., Dielectric Breakdown of Cell Membranes, Biophysical Journal, vol. 14, No. 11, pp. 881-899, 1974.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.
Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.
Co-Pending U.S. Appl. No. 12/432,295, Response to Non-Final Office Action, dated Apr. 28, 2014, 14 pages.
Co-Pending U.S. Appl. No. 12/491,151, Non-Final Rejection dated Apr. 4, 2014, 12 pages.
Co-Pending U.S. Appl. No. 12/432,295, Final Office Action dated Mar. 21, 2012, 13 pages.
Co-Pending U.S. Appl. No. 12/432,295, Response to Final Office Action Filed with RCE dated Jul. 23, 2012, 13 pages.
Co-Pending U.S. Appl. No. 12/432,295, Response to Jun. 16, 2014 Final Rejection filed Oct. 16, 2014, 13 pages.
Co-Pending U.S. Appl. No. 12/491,151, Non-Final Rejection dated Dec. 28, 2011, 7 pages.
Co-Pending U.S. Appl. No. 12/491,151, Response to Non-Final Rejection dated Mar. 28, 2012, 10 pages.
Co-Pending U.S. Appl. No. PCT/US15/30429, filed May 12, 2015.
Co-Pending U.S. Appl. No. 12/432,295, Non-Final Office Action dated Jun. 23, 2015, 12 pages.
Co-Pending U.S. Appl. No. 12/432,295, Supplemental Response After RCE, filed Nov. 17, 2014, 9 pages.
Co-Pending U.S. Appl. No. 14/686,380, filed Apr. 14, 2015.
Golberg, A. and Rubinsky, B., "A statistical model for multidimensional irreversible electroporation cell death in tissue." Biomed Eng Online, 9, 13 pages, 2010.

Neal II et al., "A Case Report on the Successful Treatment of a Large Soft-Tissue Sarcoma with Irreversible Electroporation," Journal of Clinical Oncology, 29, pp. 1-6, 2011.
Co-Pending U.S. Appl. No. 12/432,295, Final Rejection dated Jun. 16, 2014, 14 pages.
Co-Pending U.S Appl. No. 12/491,151, Response to Apr. 4, 2014 Non-Final Rejection dated Aug. 22, 2014, 12 pages.
Agerholm-Larsen, B., et al., "Preclinical Validation of Electrochemotherapy as an Effective Treatment for Brain Tumors", Cancer Research 71: 3753-3762 (2011).
Al-Sakere, B. et al., 2007, "Tumor ablation with irreversible electroporation." PLoS ONE 2.
Amasha, et al., Quantitative Assessment of Impedance Tomography for Temperature Measurements in Microwave Hyperthermia, Clin. Phys. Physiol. Meas., 1998, Suppl. A, 49-53.
Andreason, Electroporation as a Technique for the Transfer of Macromolecules into Mammalian Cell Lines, J. Tiss. Cult. Meth., 15:56-62, 1993.
Appelbaum, L., et al., "US Findings after Irreversible Electroporation Ablation: Radiologic-Pathologic Correlation" Radiology 262(1), 117-125 (2012).
Arena, Christopher B., et al., "Towards the development of latent heat storage electrodes for electroporation-based therapies", Applied Physics Letters, 101, 083902 (2012).
Arena, Christopher B., et al.,"Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Baker, et al., Calcium-Dependent Exocytosis in Bovine Adrenal Medullary Cells with Leaky Plasma Membranes, Nature, vol. 276, pp. 620-622, 1978.
Bancroft, et al., Design of a Flow Perfusion Bioreactor System for Bone Tissue-Engineering Applications, Tissue Engineering, vol. 9, No. 3, 2003, p. 549-554.
Barber, Electrical Impedance Tomography Applied Potential Tomography, Advances in Biomedical Engineering, Beneken and Thevenin, eds., IOS Press, pp. 165-173, 1993.
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-15, vol. I, Piscataway, NJ, USA.
Ben-David, E.,et al., "Characterization of Irreversible Electroporation Ablation in In Vivo Procine Liver" Am. J. Roentgenol. 198(1), W62-W68 (2012).
Blad, et al., Impedance Spectra of Tumour Tissue in Comparison with Normal Tissue; a Possible Clinical Application for Electrical Impedance Tomography, Physiol. Meas. 17 (1996) A105-A115.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Boone, K., Barber, D. & Brown, B. Review—Imaging with electricity: report of the European Concerted Action on Impedance Tomography. J. Med. Eng. Technol. 21, 201-232 (1997).
BPH Management Strategies: Improving Patient Satisfaction, Urology Times, May 2001, vol. 29, Supplement 1.
Brown, et al., Blood Flow Imaging Using Electrical Impedance Tomography, Clin. Phys. Physiol. Meas., 1992, vol. 13, Suppl. A, 175-179.
Brown, S.G., Phototherapy of tumors. World J. Surgery, 1983. 7: p. 700-9.
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).

(56) References Cited

OTHER PUBLICATIONS

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Coates, C.W.,et al., "The Electrical Discharge of the Electric Eel, Electrophorous Electricus," Zoologica, 1937, 22(1), pp. 1-32.
Cook, et al., ACT3: A High-Speed, High-Precision Electrical Impedance Tomograph, IEEE Transactions on Biomedical Engineering, vol. 41, No. 8, Aug. 1994.
Co-pending U.S. Appl. No. 10/571,162, filed Oct. 18, 2006 (published as 2007/0043345 on Feb. 22, 2007).
Co-Pending U.S. Appl. No. 12/432,295, filed Apr. 29, 2009.
Co-Pending U.S. Appl. No. 12/432,295, Final Rejection dated Mar. 21, 2012, 14 pages.
Co-Pending U.S. Appl. No. 12/432,295, Non-Final Office Action dated Nov. 26, 2013, 15 pages.
Co-Pending U.S. Appl. No. 12/432,295, Non-Final Rejection dated Nov. 10, 2011, 10 pages.
Co-Pending U.S. Appl. No. 12/432,295, Requirement for Restriction/Election dated Aug. 9, 2011, 7 pages.
Co-Pending U.S. Appl. No. 12/432,295, Response to Non-Final Rejection dated Jan. 23, 2012, 9 pages.
Co-Pending U.S. Appl. No. 12/432,295, Response to Requirement for Restriction/Election dated Sep. 2, 2011, 2 pages.
Co-Pending U.S. Appl. No. 12/432,295, Response with RCE to Final Rejection dated Jul. 23, 2012, 13 pages.
Co-Pending U.S. Appl. No. 12/491,151, Final Rejection dated Apr. 20, 2012, 8 pages.
Co-Pending U.S. Appl. No. 12/491,151, Requirement for Restriction/Election dated Dec. 2, 2011, 6 pages.
Co-Pending U.S. Appl. No. 12/491,151, Response to Requirement for Restriction/Election dated Dec. 13, 2011, 2 pages.
Co-Pending U.S. Appl. No. 12/491,151, Response with RCE to Final Rejection dated Aug. 20, 2012, 14 pages.
Co-Pending U.S. Appl. No. 12/491,151, Supplemental Amendment dated Dec. 17, 2012, 6 pages.
Co-Pending U.S. Appl. No. 12/609,779, filed Oct. 30, 2009.
Co-pending U.S. Appl. No. 12/751,826, filed Mar. 31, 2010 (published as 2010/0250209 on Sep. 30, 2010).
Co-pending U.S. Appl. No. 12/751,854, filed Mar. 31, 2010 (published as 2010/0249771 on Sep. 30, 2010).
Co-Pending U.S. Appl. No. 12/757,901, filed Apr. 9, 2010.
Co-Pending U.S. Appl. No. 12/906,923, filed Oct. 18, 2010.
Co-Pending Application No. PCT/US04/43477, filed Dec. 21, 2004.
Co-Pending Application No. PCT/US09/42100, filed Apr. 29, 2009.
Co-Pending Application No. PCT/US09/62806, filed Oct. 30, 2009.
Co-Pending Application No. PCT/US10/30629, filed Apr. 9, 2010.
Co-Pending Application No. PCT/US10/53077, filed Oct. 18, 2010.
Co-Pending Application No. PCT/US11/62067, filed Nov. 23, 2011.
Co-Pending Application No. PCT/US11/66239, filed Dec. 20, 2011.
Co-pending Application No. PCT/US2010/029243, filed Mar. 30, 2010, published as WO 2010/117806 on Oct. 14, 2010.
Co-Pending U.S. Appl. No. 12/491,151, filed Jun. 24, 2009.
Co-Pending U.S. Appl. No. 13/332,133, filed Dec. 20, 2011.
Co-Pending U.S. Appl. No. 13/550,307, filed Jul. 16, 2012.
Co-Pending U.S. Appl. No. 13/919,640, filed Jun. 17, 2013.
Co-Pending U.S. Appl. No. 13/958,152, filed Aug. 2, 2013.
Co-Pending U.S. Appl. No. 13/989,175, filed May 23, 2013.
Co-Pending U.S. Appl. No. 14/012,832 , filed Aug. 28, 2013.
Co-pending European Application No. 10 824 248.8, Invitation Pursuant to rule 62a(1) EPC (Sep. 25, 2013).
Corovic, S. et al., "Analytical and numerical quantification and comparison of the local electric field in the tissue for different electrode configurations," Biomed Eng Online, 6, 2007.
Cowley, Good News for Boomers, Newsweek, Dec. 30, 1996/Jan. 6, 1997.
Cox, et al., Surgical Treatment of Atrial Fibrillation: A Review, Europace (2004) 5, S20-S-29.

Crowley, Electrical Breakdown of Biomolecular Lipid Membranes as an Electromechanical Instability, Biophysical Journal, vol. 13, pp. 711-724, 1973.
Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos, et al ., Theoretical Analysis of the Thermal Effects During In Vivo Tissue Electroporation, Bioelectrochemistry, vol. 61, pp. 99-107, 2003.
Davalos, et al., A Feasibility Study for Electrical Impedance Tomography as a Means to Monitor T issue Electroporation for Molecular Medicine, IEEE Transactions on Biomedical Engineering, vol. 49, No. 4, Apr. 2002.
Davalos, et al., Tissue Ablation with Irreversible Electroporation, Annals of Biomedical Engineering, vol. 33, No. 2, p. 223-231, Feb. 2005.
Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).
Davalos, R.V., et al., "Electrical impedance tomography for imaging tissue electroporation," IEEE Transactions on Biomedical Engineering, 51, 761-767, 2004.
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
Dean, Nonviral Gene Transfer to Skeletal, Smooth, and Cardiac Muscle in Living Animals, Am J. Physiol Cell Physiol 289: 233-245, 2005.
Demirbas, M. F., "Thermal Energy Storage and Phase Change Materials: An Overview" Energy Sources Part B 1(1), 85-95 (2006).
Dev, et al., Medical Applications of Electroporation, IEEE Transactions of Plasma Science, vol. 28, No. 1, pp. 206-223, Feb. 2000.
Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.
Duraiswami, et al., Boundary Element Techniques for Efficient 2-D and 3-D Electrical Impedance Tomography, Chemical Engineering Science, vol. 52, No. 13, pp. 2185-2196, 1997.
Duraiswami, et al., Efficient 2D and 3D Electrical Impedance Tomography Using Dual Reciprocity Boundary Element Techniques, Engineering Analysis with Boundary Elements 22, (1998) 13-31.
Duraiswami, et al., Solution of Electrical Impedance Tomography Equations Using Boundary Element Methods, Boundary Element Technology XII, 1997, pp. 226-237.
Edd, J., et al., In-Vivo Results of a New Focal Tissue Ablation Technique: Irreversible Electroporaton, IEEE Trans. Biomed. Eng. 53 (2006) p. 1409-1415.
Edd, J.F, et al., 2007, "Mathematical modeling of irreversible electroporation fortreatment planning.", Technology in Cancer Research and Treatment., 6:275-286.
Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).
Erez, et al., Controlled Destruction and Temperature Distributions in Biological Tissues Subjected to Monoactive Electrocoagulation, Transactions of the ASME: Journal of Mechanical Design, vol. 102, Feb. 1980.
Extended European Search Report. May 11, 2012. PCT/US2009042100 from EP 09739678.2.
Faroja, M., et al., "Irreversible Electroporation Ablation: Is the entire Damage Nonthermal?", Radiology, 266(2), 462-470 (2013).
Foster RS, "High-intensity focused ultrasound in the treatment of prostatic disease", European Urology, 1993, vol. 23 Suppl 1, pp. 29-33.
Foster, R.S., et al., Production of Prostatic Lesions in Canines Using Transrectally Administered High-Intensity Focused Ultrasound. Eur. Urol., 1993; 23: 330-336.
Fox, et al., Sampling Conductivity Images via MCMC, Mathematics Department, Auckland University, New Zealand, May 1997.

(56) References Cited

OTHER PUBLICATIONS

Garcia et al., "Irreversible electroporation (IRE) to treat brain cancer." ASME Summer Bioengineering Conference, Marco Island, FL, Jun. 25-29, 2008.

Garcia P.A., et al., "7.0-T Magnetic Resonance Imaging Characterization of Acute Blood-Brain-Barrier Disruption Achieved with Intracranial Irreversible Electroporation", PLOS ONE, Nov. 2012, 7:11, e50482.

Garcia P.A., et al., "Pilot study of irreversible electroporation for intracranial surgery", Conf Proc IEEE Eng Med Biol Soc, 2009:6513-6516, 2009.

Garcia PA, Rossmeisl JH, Jr., Neal RE, 2nd, Ellis TL, Davalos RV, "A Parametric Study Delineating Irreversible Electroporation from Thermal Damage Based on a Minimally Invasive Intracranial Procedure", Biomed Eng Online 10: 34 (2011).

Garcia, P. A., et al., "Towards a predictive model of electroporation-based therapies using pre-pulse electrical measurements," Conf Proc IEEE Eng Med Biol Soc, vol. 2012, pp. 2575-2578, 2012.

Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).

Garcia, P. et al. Intracranial nonthermal irreversible electroporation: in vivo analysis. J Membr Biol 236, 127-136 (2010).

Gauger, et al., A Study of Dielectric Membrane Breakdown in the Fucus Egg, J. Membrane Biol., vol. 48, No. 3, pp. 249-264, 1979.

Gehl, et al., In Vivo Electroporation of Skeletal Muscle: Threshold, Efficacy and Relation to Electric Field Distribution, Biochimica et Biphysica Acta 1428, 1999, pp. 233-240.

Gençer, et al., Electrical Impedance Tomography: Induced-Current Imaging Achieved with a Multiple Coil System, IEEE Transactions on Biomedical Engineering, vol. 43, No. 2, Feb. 1996.

Gilbert, et al., Novel Electrode Designs for Electrochemotherapy, Biochimica et Biophysica Acta 1334, 1997, pp. 9-14.

Gilbert, et al., The Use of Ultrasound Imaging for Monitoring Cryosurgery, Proceedings 6th Annual Conference, IEEE Engineering in Medicine and Biology, 107-111, 1984.

Gilbert, T. W., et al., "Decellularization of tissues and organs", Biomaterials, Elsevier Science Publishers, Barking, GB, vol. 27, No. 19, Jul. 1, 2006, pp. 3675-3683.

Glidewell, et al., The Use of Magnetic Resonance Imaging Data and the Inclusion of Anisotropic Regions in Electrical Impedance Tomography, Biomed, Sci. Instrum. 1993; 29: 251-7.

Gothelf, et al., Electrochemotherapy: Results of Cancer Treatment Using Enhanced Delivery of Bleomycin by Electroporation, Cancer Treatment Reviews 2003: 29: 371-387.

Griffiths, et al., A Dual-Frequency Electrical Impedance Tomography System, Phys. Med. Biol., 1989, vol. 34, No. 10, pp. 1465-1476.

Griffiths, The Importance of Phase Measurement in Electrical Impedance Tomography, Phys. Med. Biol., 1987, vol. 32, No. 11, pp. 1435-1444.

Griffiths, Tissue Spectroscopy with Electrical Impedance Tomography: Computer Simulations, IEEE Transactions on Biomedical Engineering, vol. 42, No. 9, Sep. 1995.

Gumerov, et al., The Dipole Approximation Method and Its Coupling with the Regular Boundary Element Method for Efficient Electrical Impedance Tomography, Boundary Element Technology XIII, 1999.

Hapala, Breaking the Barrier: Methods for Reversible Permeabilization of Cellular Membranes, Critical Reviews in Biotechnology, 17(2): 105-122, 1997.

Heller, et al., Clinical Applications of Electrochemotherapy, Advanced Drug Delivery Reviews, vol. 35, pp. 119-129, 1999.

Hjouj, M., et al., "Electroporation-Induced BBB Disruption and Tissue Damage Depicted by MRI", Neuro-Oncology 13: Issue suppl 3, abstract ET-32 (2011).

Hjouj, M., et al., "MRI Study on Reversible and Irreversible Electroporation Induced Blood Brain Barrier Disruption", PLOS ONE, Aug. 2012, 7:8, e42817.

Ho, et al., Electroporation of Cell Membranes: A Review, Critical Reviews in Biotechnology, 16(4): 349-362, 1996.

Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical BI, pp. 512-519, 1999.

Huang, et al., Micro-Electroporation: Improving the Efficiency and Understanding of Electrical Permeabilization of Cells, Biomedical Microdevices, vol. 2, pp. 145-150, 1999.

Hughes, et al., An Analysis of Studies Comparing Electrical Impedance Tomography with X-Ray Videofluoroscopy in the Assessment of Swallowing, Physiol. Meas. 15, 1994, pp. A199-A209.

Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998.

Ivanuša, et al., MRI Macromolecular Contrast Agents as Indicators of Changed Tumor Blood Flow, Radiol. Oncol. 2001; 35(2): 139-47.

Jaroszeski, et al., In Vivo Gene Delivery by Electroporation, Advanced Drug Delivery Review, vol. 35, pp. 131-137, 1999.

Jossinet et al., Electrical Impedance Endo-Tomography: Imaging Tissue From Inside, IEEE Transactions on Medical Imaging, vol. 21, No. 6, June 2002, pp. 560-565.

Kinosita, et al., Hemolysis of Human Erythrocytes by a Transient Electric Field, Proc. Natl. Acad. Sci. USA, vol. 74, No. 5, pp. 1923-1927, 1977.

Lee, E. W. et al. Advanced Hepatic Ablation Technique for Creating Complete Cell Death : Irreversible Electroporation. Radiology 255, 426-433, doi:10.1148/radiol.10090337 (2010).

Lee, E.W., et al., "Imaging guided percutaneous irreversible electroporation: ultrasound and immunohistological correlation", Technol Cancer Res Treat 6: 287-294 (2007).

Li, W., et al., "The Effects of Irreversible Electroporation (IRE) on Nerves" PloS One, Apr. 2011, 6(4), e18831.

Liu, et al., Measurement of Pharyngeal Transit Time by Electrical Impedance Tomography, Clin. Phys. Physiol. Meas., 1992, vol. 13, Suppl. A, pp. 197-200.

Lundqvist, et al., Altering the Biochemical State of Individual Cultured Cells and Organelles with Ultramicroelectrodes, Proc. Natl. Acad. Sci. USA, vol. 95, pp. 10356-10360, Sep. 1998.

Lurquin, Gene Transfer by Electroporation, Molecular Biotechnology, vol. 7, 1997.

Lynn, et al., A New Method for the Generation and Use of Focused Ultrasound in Experimental Biology, The Journal of General Physiology, vol. 26, 179-193, 1942.

Mahmood, F., et al., "Diffusion-Weighted MRI for Verification of Electroporation-Based Treatments", Journal of Membrane Biology 240: 131-138 (2011).

Mahnic-Kalamiza, S., et al., "Educational application for visualization and analysis of electric field strength in multiple electrode electroporation," BMC Med Educ, vol. 12, p. 102, 2012.

Maor et al., The Effect of Irreversible Electroporation on Blood Vessels, Tech. in Cancer Res. and Treatment, vol. 6, No. 4, Aug. 2007, pp. 307-312.

Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.

Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.

Marty, M., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.

Miklavčič, et al., A Validated Model of an in Vivo Electric Field Distribution in Tissues for Electrochemotherapy and for DNA Electrotransfer for Gene Therapy, Biochimica et Biophysica Acta 1523 (2000), pp. 73-83.

Miklavčič, et al., The Importance of Electric Field Distribution for Effective in Vivo Electroporation of Tissues, Biophysical Journal, vol. 74, May 1998, pp. 2152-2158.

(56) References Cited

OTHER PUBLICATIONS

Miller, L., et al., Cancer cells ablation with irreversible electroporation, Technology in Cancer Research and Treatment 4 (2005) 699-706.
Mir et al., "Mechanisms of Electrochemotherapy" Advanced Drug Delivery Reviews 35:107-118 (1999).
Mir, et al., Effective Treatment of Cutaneous and Subcutaneous Malignant Tumours by Electrochemotherapy, British Journal of Cancer, vol. 77, No. 12, pp. 2336-2342, 1998.
Mir, et al., Electrochemotherapy Potentiation of Antitumour Effect of Bleomycin by Local Electric Pulses, European Journal of Cancer, vol. 27, No. 1, pp. 68-72, 1991.
Mir, et al., Electrochemotherapy, a Novel Antitumor Treatment: First Clinical Trial, C.R. Acad. Sci. Paris, Ser. III, vol. 313, pp. 613-618, 1991.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Mir, L.M., et al., Electric Pulse-Mediated Gene Delivery to Various Animal Tissues, in Advances in Genetics, Academic Press, 2005, p. 83-114.
Mir, Therapeutic Perspectives of In Vivo Cell Electropermeabilization, Bioelectrochemistry, vol. 53, pp. 1-10, 2000.
Narayan, et al., Establishment and Characterization of a Human Primary Prostatic Adenocarcinoma Cell Line (ND-1), The Journal of Urology, vol. 148, 1600-1604, Nov. 1992.
Naslund, Cost-Effectiveness of Minimally Invasive Treatments and Transurethral Resection (TURP) in Benign Prostatic Hyperplasia (BPH), (Abstract), Presented at 2001 AUA National Meeting Anaheim, CA, Jun. 5, 2001.
Naslund, Michael J., Transurethral Needle Ablation of the Prostate, Urology, vol. 50, No. 2, Aug. 1997.
Neal II, R. E., et al., "Experimental characterization and numerical modeling of tissue electrical conductivity during pulsed electric fields for irreversible electroporation treatment planning," IEEE Trans Biomed Eng., vol. 59:4, pp. 1076-85. Epub 2012 Jan. 6, 2012.
Neal II, R. E., et al., "Successful Treatment of a Large Soft Tissue Sarcoma with Irreversible Electroporation", Journal of Clinical Oncology, 29:13, e372-e377 (2011).
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Neumann, et al., Gene Transfer into Mouse Lyoma Cells by Electroporation in High Electric Fields, J. Embo., vol. 1, No. 7, pp. 841-845, 1982.
Neumann, et al., Permeability Changes Induced by Electric Impulses in Vesicular Membranes, J. Membrane Biol., vol. 10, pp. 279-290, 1972.
Co-Pending U.S. Appl. No. 12/491,151, Offcial Notice of Allowance dated Nov. 6, 2014, 15 pages.
Co-Pending U.S. Appl. No. 14/558,631, filed Dec. 2, 2014.
Co-Pending U.S. Appl. No. 14/627,046, filed Feb. 20, 2015.
Co-Pending U.S. Appl. No. 13/550,307, Response to Final Office Action filed Feb. 23, 2016, 9 pages.
Hjouj, Mohammad et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, p. ii114.
Reberšek, M. and D. Miklavčič, "Advantages and Disadvantages of Different Concepts of Electroporation Pulse Generation," Automatika 52(2011) 1, 12-19.
Alberts et al., "Molecular Biology of the Cell," 3rd edition, Garland Science, New York, 1994, 1 page.

Arena et al. "High-Frequency Irreversible Electroporation (H-FIRE) for Non-thermal Ablation without Muscle Contraction." Biomed. Eng. Online, vol. 10, 20 pages (2011).
Arena, C.B., et al., "A three-dimensional in vitro tumor platform for modeling therapeutic irreversible electroporation." Biophysical Journal, 2012.103(9): p. 2033-2042.
Asami et al., "Dielectric properties of mouse lymphocytes and erythrocytes." Biochimica et Biophysica Acta (BBA)—Molecular Cell Research, 1010 (1989) pp. 49-55.
Ball, C., K.R. Thomson, and H. Kavnoudias, "Irreversible electroporation: a new challenge in "out of-operating theater" anesthesia." Anesth Analg, 2010. 110(5): p. 1305-9.
Bower et al., "Irreversible electroporation of the pancreas: definitive local therapy without systemic effects." Journal of surgical oncology, 2011. 104(1): p. 22-28.
Cannon et al., "Safety and early efficacy of irreversible electroporation for hepatic tumors in proximity to vital structures." Journal of Surgical Oncology, 6 pages (2012).
Carpenter A.E. et al., "CellProfiler: image analysis software for identifying and quantifying cell phenotypes." Genome Biol. 2006; 7(10): R100. Published online Oct. 31, 2006, 11 pages.
Charpentier, K.P., et al., "Irreversible electroporation of the pancreas in swine: a pilot study." HPB: the official journal of the International Hepato Pancreato Biliary Association, 2010. 12(5): p. 348-351.
Chen et al., "Classification of cell types using a microfluidic device for mechanical and electrical measurement on single cells." Lab on a Chip, vol. 11, pp. 3174-3181 (2011).
Clark et al., "The electrical properties of resting and secreting pancreas." The Journal of Physiology, vol. 189, pp. 247-260 (1967).
Co-Pending U.S. Appl. No. 14/808,679, filed Jul. 24, 2015.
Dahl et al., "Nuclear shape, mechanics, and mechanotransduction." Circulation Research vol. 102, pp. 1307-1318 (2008).
Eppich et al., "Pulsed electric fields for selection of hematopoietic cells and depletion of tumor cell contaminants." Nature Biotechnology 18, pp. 882-887 (2000).
Ermolina et al., "Study of normal and malignant white blood cells by time domain dielectric spectroscopy." IEEE Transactions on Dielectrics and Electrical Insulation, 8 (2001) pp. 253-261.
Fischbach et al., "Engineering tumors with 3D scaffolds." Nat Meth 4, pp. 855-860 (2007).
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Gascoyne et al., "Membrane changes accompanying the induced differentiation of Friend murine erythroleukemia cells studied by dielectrophoresis." Biochimica et Biophysica Acta (BBA)—Biomembranes, vol. 1149, pp. 119-126 (1993).
Gimsa et al., "Dielectric spectroscopy of single human erythrocytes at physiological ionic strength: dispersion of the cytoplasm." Biophysical Journal, vol. 71, pp. 495-506 (1996).
Helczynska et al., "Hypoxia promotes a dedifferentiated phenotype in ductal breast carcinoma in situ." Cancer Research, vol. 63, pp. 1441-1444 (2003).
Ibey et al., "Selective cytotoxicity of intense nanosecond-duration electric pulses in mammalian cells." Biochimica Et Biophysica Acta-General Subjects, vol. 1800, pp. 1210-1219 (2010).
Jarm et al., "Antivascular effects of electrochemotherapy: implications in treatment of bleeding metastases." Expert Rev Anticancer Ther. vol. 10, pp. 729-746 (2010).
Jensen et al., "Tumor volume in subcutaneous mouse xenografts measured by microCT is more accurate and reproducible than determined by 18FFDG-microPET or external caliper." BMC medical Imaging vol. 8:16, 9 Pages (2008).
Kingham et al., "Ablation of perivascular hepatic malignant tumors with irreversible electroporation." Journal of the American College of Surgeons, 2012. 215(3), p. 379-387.
Kinosita and Tsong, "Formation and resealing of pores of controlled sizes in human erythrocyte membrane." Nature, vol. 268 (1977) pp. 438-441.

(56) References Cited

OTHER PUBLICATIONS

Kinosita and Tsong, "Voltage-induced pore formation and hemolysis of human erythrocytes." Biochimica et Biophysica Acta (BBA)—Biomembranes, 471 (1977) pp. 227-242.
Kinosita et al., "Electroporation of cell membrane visualized under a pulsed-laser fluorescence microscope." Biophysical Journal, vol. 53, pp. 1015-1019 (1988).
Kirson et al., "Alternating electric fields arrest cell proliferation in animal tumor models and human brain tumors." Proceedings of the National Academy of Sciences vol. 104, pp. 10152-10157 (2007).
Kotnik and Miklavcic, "Theoretical evaluation of voltage inducement on internal membranes of biological cells exposed to electric fields." Biophysical Journal, vol. 90(2), pp. 480-491 (2006).
Labeed et al., "Differences in the biophysical properties of membrane and cytoplasm of apoptotic cells revealed using dielectrophoresis." Biochimica et Biophysica Acta (BBA)—General Subjects, vol. 1760, pp. 922-929 (2006).
Lebar et al., "Inter-pulse interval between rectangular voltage pulses affects electroporation threshold of artificial lipid bilayers." IEEE Transactions on NanoBioscience, vol. 1 (2002) pp. 116-120.
Maček Lebar and Miklavčič, "Cell electropermeabilization to small molecules in vitro: control by pulse parameters." Radiology and Oncology, vol. 35(3), pp. 193-202 (2001).
Malpica et al., "Grading ovarian serous carcinoma using a two-tier system." The American Journal of Surgical Pathology, vol. 28, pp. 496-504 (2004).
Marszalek et al., "Schwan equation and transmembrane potential induced by alternating electric field." Biophysical Journal, vol. 58, pp. 1053-1058 (1990).
Martin, n.R.C.G., et al., "Irreversible electroporation therapy in the management of locally advanced pancreatic adenocarcinoma." Journal of the American College of Surgeons, 2012. 215(3): p. 361-369.
Mulhall et al., "Cancer, pre-cancer and normal oral cells distinguished by dielectrophoresis." Analytical and Bioanalytical Chemistry, vol. 401, pp. 2455-2463 (2011).
Neal II, R.E., et al., "Treatment of breast cancer through the application of irreversible electroporation using a novel minimally invasive single needle electrode." Breast Cancer Research and Treatment, 2010. 123(1): p. 295-301.
Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).
O'Brien et al., "Investigation of the Alamar Blue (resazurin) fluorescent dye for the assessment of mammalian cell cytotoxicity." European Journal of Biochemistry, vol. 267, pp. 5421-5426 (2000).
Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.
Onik, G., P. Mikus, and B. Rubinsky, "Irreversible electroporation: implications for prostate ablation." Technol Cancer Res Treat, 2007. 6(4): p. 295-300.
Paszek et al., "Tensional homeostasis and the malignant phenotype." Cancer Cell, vol. 8, pp. 241-254 (2005).
Polak et al., "On the Electroporation Thresholds of Lipid Bilayers: Molecular Dynamics Simulation Investigations." The Journal of Membrane Biology, vol. 246, pp. 843-850 (2013).
Pucihar et al., "Numerical determination of transmembrane voltage induced on irregularly shaped cells." Annals of Biomedical Engineering, vol. 34, pp. 642-652 (2006).
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rubinsky et al., "Optimal Parameters for the Destruction of Prostate Cancer Using Irreversible Electroporation." The Journal of Urology, 180 (2008) pp. 2668-2674.
Sabuncu et al., "Dielectrophoretic separation of mouse melanoma clones." Biomicrofluidics, vol. 4, 7 pages (2010).
Co-Pending U.S. Appl. No. 14/940,863, filed Nov. 13, 2015 and Published as US 2016/0066977 on Mar. 10, 2016.
Co-Pending U.S. Appl. No. 15/011,752, filed Feb. 1, 2016.
Ivorra et al., "In vivo electric impedance measurements during and after electroporation of rat live." Bioelectrochemistry, vol. 70, pp. 287-295 (2007).
Ivorra et al., "In vivo electrical conductivity measurements during and after tumor electroporation: conductivity changes reflect the treatment outcome." Physics in Medicine and Biology, vol. 54, pp. 5949-5963 (2009).
Ivorra, "Bioimpedance monitoring for physicians: an overview." Biomedical Applications Group, 35 pages (2002).
Laufer et al., "Electrical impedance characterization of normal and cancerous human hepatic tissue." Physiological Measurement, vol. 31, pp. 995-1009 (2010).
Salmanzadeh et al., "Investigating dielectric properties of different stages of syngeneic murine ovarian cancer cells" Biomicrofluidics 7, 011809 (2013), 12 pages.
Salmanzadeh et al., "Dielectrophoretic differentiation of mouse ovarian surface epithelial cells, macrophages, and fibroblasts using contactless dielectrophoresis." Biomicrofluidics, vol. 6, 13 Pages (2012).
Salmanzadeh et al., "Sphingolipid Metabolites Modulate Dielectric Characteristics of Cells in a Mouse Ovarian Cancer Progression Model." Integr. Biol., 5(6), pp. 843-852 (2013).
Sano et al., "Contactless Dielectrophoretic Spectroscopy: Examination of the Dielectric Properties of Cells Found in Blood." Electrophoresis, 32, pp. 3164-3171, 2011.
Sano et al., "In-vitro bipolar nano- and microsecond electro-pulse bursts for irreversible electroporation therapies." Bioelectrochemistry vol. 100, pp. 69-79 (2014).
Sano et al., "Modeling and Development of a Low Frequency Contactless Dielectrophoresis (cDEP) Platform to Sort Cancer Cells from Dilute Whole Blood Samples." Biosensors & Bioelectronics, 8 pages (2011).
Saur et al., "CXCR4 expression increases liver and lung metastasis in a mouse model of pancreatic cancer." Gastroenterology, vol. 129, pp. 1237-1250 (2005).
Schoenbach et al., "Intracellular effect of ultrashort electrical pulses." Bioelectromagnetics, 22 (2001) pp. 440-448.
Seibert et al., "Clonal variation of MCF-7 breast cancer cells in vitro and in athymic nude mice." Cancer Research, vol. 43, pp. 2223-2239 (1983).
Seidler et al., "A Cre-loxP-based mouse model for conditional somatic gene expression and knockdown in vivo by using avian retroviral vectors." Proceedings of the National Academy of Sciences, vol. 105, pp. 10137-10142 (2008).
Szot et al., "3D in vitro bioengineered tumors based on collagen I hydrogels." Biomaterials vol. 32, pp. 7905-7912 (2011).
Verbridge et al., "Oxygen-Controlled Three-Dimensional Cultures to Analyze Tumor Angiogenesis." Tissue Engineering, Part A vol. 16, pp. 2133-2141 (2010).
Weaver et al., "A brief overview of electroporation pulse strength-duration space: A region where additional intracellular effects are expected." Bioelectrochemistry vol. 87, pp. 236-243 (2012).
Yang et al., "Dielectric properties of human leukocyte subpopulations determined by electrorotation as a cell separation criterion." Biophysical Journal, vol. 76, pp. 3307-3314 (1999).
Yao et al., "Study of transmembrane potentials of inner and outer membranes induced by pulsed-electric-field model and simulation." IEEE Trans Plasma Sci, 2007. 35(5): p. 1541-1549.
Zhang, Y., et al., MR imaging to assess immediate response to irreversible electroporation for targeted ablation of liver tissues: preclinical feasibility studies in a rodent model. Radiology, 2010. 256(2): p. 424-32.
Baptista et al., "The Use of Whole Organ Decellularization for the Generation of a Vascularized Liver Organoid," Heptatology, vol. 53, No. 2, pp. 604-617 (2011).

(56) References Cited

OTHER PUBLICATIONS

Co-Pending U.S. Appl. No. 14/686,380, filed Apr. 14, 2015 and Published as US 2015/0289923 on Oct. 15, 2015.
Co-Pending U.S. Appl. No. PCT/US15/30429, International Search Report and Written Opinion dated Oct. 16, 2015, 19 pages.
Co-Pending Application No. PCT/US2015/030429, Published on Nov. 19, 2015 as WO 2015/175570.
Co-Pending U.S. Appl. No. 12/432,295, Response to Jun. 23, 2015 Non-Final Office Action dated Oct. 23, 2015, 46 pages.
Co-Pending U.S. Appl. No. 12/432,295, Final Office Action dated Nov. 25, 2015, 14 pages.
Co-Pending U.S. Appl. No. 12/432,295, Response to Nov. 25, 2015 Final Office Action, filed Jan. 25, 2016, 12 pages.
Co-Pending U.S. Appl. No. 13/550,307, Final Office Action dated Oct. 23, 2015, 10 pages.
Co-Pending U.S. Appl. No. 13/550,307, Non-Final Office Action dated Apr. 15, 2015, 10 pages.
Co-Pending U.S. Appl. No. 13/550,307, Response to Non-Final Office Action filed Jul. 15, 2015, 9 pages.
Co-Pending U.S. Appl. No. 13/550,307, Response to Restriction Requirement filed Mar. 9, 2015, 3 pages.
Co-Pending U.S. Appl. No. 13/550,307, Restriction Requirement dated Jan. 7, 2015, 8 pages.
Co-Pending U.S. Appl. No. 12/432,295, Notice of Allowance and Interview Summary dated Nov. 3, 2016, 9 pages.
Co-Pending U.S. Appl. No. 13/550,307, Non-Final Office Action dated Aug. 26, 2016, 12 pages.
PCT IPRP for PCT/US15/30429 (WO2015175570), dated Nov. 15, 2016.
Beebe, S.J., et al., "Diverse effects of nanosecond pulsed electric fields on cells and tissues", DNA and Cell Biology, 22(12): 785-796 (2003).
Chang, D.C., "Cell Poration and Cell-Fusion Using an Oscillating Electric-Field". Biophysical Journal, 56(4): p. 641-552 (1989).
Chen, M.T., et al., "Two-dimensional nanosecond electric field mapping based on cell electropermeabilization", PMC Biophys, 2(1):9 (2009).
Co-Pending U.S. Appl. No. 12/432,295, Advisory Action and Examiner Interview Summary dated Feb. 9, 2016, 5 pages.
Co-Pending U.S. Appl. No. 12/432,295, Appeal Brief and Appendices dated Jul. 25, 2016, 94 pages.
Co-pending U.S. Appl. No. 15/186,653, filed June 20, 2016.
Co-Pending U.S. Appl. No. 13/550,307, Final Office Action dated Aug. 26, 2016, 12 pages.
De Vuyst, E. et al., "In situ bipolar Electroporation for localized cell loading with reporter dyes and investigating gap junctional coupling", Biophysical Journal, 94(2): p. 469-479 (2008).
Esser, A.T., et al., "Towards solid tumor treatment by irreversible electroporation: intrinsic redistribution of fields and currents in tissue". Technol Cancer Res Treat, 6(4): p. 261-74 (2007).
Esser, A.T., et al., "Towards Solid Tumor Treatment by Nanosecond Pulsed Electric Fields", Technology in Cancer Research & Treatment, 8(4): p. 289-306 (2009).
Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).
Gowrishankar T.R., et al., "Microdosimetry for conventional and supra-electroporation in cells with organelles". Biochem Biophys Res Commun, 341(4): p. 1266-76 (2006).
Kotnik, T. and D. Miklavcic, "Theoretical evaluation of the distributed power dissipation in biological cells exposed to electric fields", Bioelectromagnetics, 21(5): p. 385-394 (2000).
Kotnik, T., et al., "Cell membrane electropermeabilization by symmetrical bipolar rectangular pulses. Part II. Reduced electrolytic contamination", Bioelectrochemistry, 54(1): p. 91-5 (2001).
Kotnik, T., et al., "Role of pulse shape in cell membrane electropermeabilization", Biochimica Et Biophysica Acta-Biomembranes, 1614(2): p. 193-200 (2003).

Lackovic, I., et al., "Three-dimensional Finite-element Analysis of Joule Heating in Electrochemotherapy and in vivo Gene Electrotransfer", Ieee Transactions on Dielectrics and Electrical Insulation, 16(5): p. 1338-1347 (2009).
Long, G., et al., "Targeted Tissue Ablation With Nanosecond Pulses". Ieee Transactions on Biomedical Engineering, 58(8) (2011).
Nikolova, B., et al., "Treatment of Melanoma by Electroporation of Bacillus Calmette-Guerin". Biotechnology & Biotechnological Equipment, 25(3): p. 2522-2524 (2011).
Nuccitelli, R., et al., "A new pulsed electric field therapy for melanoma disrupts the tumor's blood supply and causes complete remission without recurrence", Int J Cancer, 125(2): p. 438-45 (2009).
Talele, S., et al., "Modelling single cell electroporation with bipolar pulse parameters and dynamic pore radii". Journal of Electrostatics, 68(3): p. 261-274 (2010).
Vernier, P.T., et al., "Nanoelectropulse-driven membrane perturbation and small molecule permeabilization", Bmc Cell Biology, 7 (2006).
Weaver, J.C., "Electroporation of cells and tissues", IEEE Transactions on Plasma Science, 28(1): p. 24-33 (2000).
Co-Pending U.S. Appl. No. 12/432,295, Amendment with RCE dated Oct. 19, 2016, 9 pages.
Co-pending U.S. Appl. No. 15/423,986, filed Feb. 3, 2017.
Co-pending U.S. Appl. No. 15/424,335, filed Feb. 3, 2017.
Co-Pending U.S. Appl. No. 13/550,307, Interview Summary and Misc. Internal Document dated Dec. 23, 2016, 4 pages.
Co-Pending U.S. Appl. No. 13/550,307, Response to Aug. 26, 2016 Non-Final Office Action, filed Nov. 28, 2016, 14 pages.
Co-Pending U.S. Appl. No. 13/550,307, Supplemental Amendment filed Dec. 21, 2016, 9 pages.
Co-Pending U.S. Appl. No. 12/609,779, Final Rejection dated Oct. 26, 2012, 20 pages.
Co-Pending U.S. Appl. No. 12/609,779, Non-Final Rejection dated May 23, 2012, 17 pages.
Co-Pending U.S. Appl. No. 12/609,779, Notice of Allowance dated Feb. 12, 2013, 7 pages.
Co-Pending U.S. Appl. No. 12/609,779, Notice of Allowance dated May 23, 2013, 2 pages.
Co-Pending U.S. Appl. No. 12/609,779, Response to Non-Final Rejection dated Sep. 24, 2012, 37 pages.
Co-Pending U.S. Appl. No. 12/609,779, Response with RCE to Final Rejection dated Dec. 18, 2012, 20 pages.
Co-Pending U.S. Appl. No. 12/757,901, Certificate of Correction, dated Aug. 2016, 3 pages.
Co-Pending U.S. Appl. No. 12/906,923, File History dated Jul. 2017, 55 pages.
Co-Pending U.S. Appl. No. 13/989,175, Final Office Action dated Feb. 29, 2016, 20 pages.
Co-Pending U.S. Appl. No. 13/989,175, Final Office Action dated May 10, 2017, 14 pages.
Co-Pending U.S. Appl. No. 13/989,175, Interview Summary dated May 31, 2016, 4 pages.
Co-Pending U.S. Appl. No. 13/989,175, Non-Final Office Action dated May 7, 2015, 21 pages.
Co-Pending U.S. Appl. No. 13/989,175, Non-Final Office Action dated Oct. 6, 2016, 11 pages.
Co-Pending U.S. Appl. No. 13/989,175, Response dated Jan. 6, 2017, 10 pages.
Co-Pending U.S. Appl. No. 13/989,175, Response to Feb. 29, 2016 Final Office Action dated May 31, 2016, 12 pages.
Co-Pending U.S. Appl. No. 13/989,175, Response to May 7, 2015 Non-Final Office Action, filed Nov. 6, 2015, 30 pages.
Co-Pending U.S. Appl. No. 14/808,679, Preliminary Amendment, filed Jul. 27, 2015, 9 pages.
Co-pending U.S. Appl. No. 15/186,653, Preliminary Amendment filed Jun. 21, 2016, 5 pages.
Co-Pending U.S. Appl. No. 15/310,114, filed Nov. 10, 2016.
Co-Pending U.S. Appl. No. 15/310,114, Preliminary Amendment filed Nov. 10, 2016, 9 pages.

(56) References Cited

OTHER PUBLICATIONS

Co-pending U.S. Appl. No. 15/424,335 Preliminary Amendment filed Apr. 17, 2017, 17 pages.
Co-Pending U.S. Appl. No. 13/332,133, File History dated Aug. 1, 2017, 160 pages.
Co-Pending U.S. Appl. No. 13/550,307, Final Office Action dated May 23, 2017, 13 pages.
Co-Pending U.S. Appl. No. 13/958,152, Interview Summary dated Mar. 2, 2017, 4 pages.
Co-Pending U.S. Appl. No. 13/958,152, Non-Final Office Action dated Jun. 15, 2017, 18 pages.
Co-Pending U.S. Appl. No. 13/989,175, Response to Restriction Requirement dated Feb. 2, 2015, Response filed Apr. 1, 2015, 2 pages.
Co-Pending U.S. Appl. No. 13/989,175, Restriction Requirement dated Feb. 2, 2015, 5 pages.
Co-Pending U.S. Appl. No. 14/627,046, Non-Final Office Action dated Mar. 29, 2017, 9 pages.
Co-Pending U.S. Appl. No. 14/627,046, Response to Mar. 29, 2017 Non-Final Office Action, dated Jun. 29, 2017, 8 pages.
Co-pending U.S. Appl. No. 13/958,152 Office Actions and Responses dated Aug. 2, 2017, 274 pages.
Co-Pending U.S. Appl. No. 13/989,175, Notice of Allowance dated Sep. 1, 2017, 7 pages.
Co-Pending U.S. Appl. No. 13/989,175, Office Actions and Responses dated Aug. 30, 2017, 172 pages.
Co-Pending U.S. Appl. No. 13/989,175, Response to May 10, 2017 Final Office Action dated Aug. 10, 2017, 9 pages.
Co-Pending U.S. Appl. No. 13/989,175, Supplemental Notice of Allowability, dated Dec. 6, 2017, 4 pages.
Co-Pending U.S. Appl. No. 13/989,175, Supplemental Notice of Allowability, dated Nov. 30, 2017, 4 pages.
Co-Pending U.S. Appl. No. 14/558,631, Final Office Action dated Sep. 1, 2017, 9 pages.
Co-Pending U.S. Appl. No. 14/558,631, Non-Final Office Action dated Jan. 8, 2018, 5 pages.
Co-Pending U.S. Appl. No. 14/558,631, Non-Final Office Action dated Mar. 13, 2017, 10 pages.
Co-pending U.S. Appl. No. 14/558,631, Response to Mar. 13, 2017 Non-Final Office Action dated Jul. 13, 2017, 10 pages.
Co-Pending U.S. Appl. No. 14/558,631, Response to Sep. 1, 2017 Final Office Action dated Dec. 1, 2017, 7 pages.
Co-Pending U.S. Appl. No. 13/958,152, Final Office Action dated Dec. 22, 2017, 19 pages.
Co-Pending U.S. Appl. No. 13/958,152, Response to Jun. 15, 2017 Non-Final Office Action dated Sep. 5, 2017, 10 pages.
Co-Pending U.S. Appl. No. 14/621,046, Final Office Action dated Sep. 14, 2017, 11 pages.
Co-Pending U.S. Appl. No. 14/627,046, Response to Sep. 14, 2017 Final Office Action dated Dec. 14, 2017, 7 pages.
Co-Pending U.S. Appl. No. 14/686,380, Non-Final Officce Action dated Nov. 22, 2017, 11 pages.
Co-Pending U.S. Appl. No. 14/686,380, Response to Jul. 19, 2017 Restriction Requirement, dated Sep. 15, 2017, 2 pages.
Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010, 22 pages.
Neal RE II, et al. (2013) Improved Local and Systemic Anti-Tumor Efficacy for Irreversible Electroporation in Immunocompetent versus Immunodeficient Mice. PLoS ONE 8(5): e64559. https://doi.org/10.1371/journal.pone.0064559.

Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi:10.1007/s00270-014-0905-2.
Co-Pending U.S. Appl. No. 12/757,901, File History 2018.
Co-Pending U.S. Appl. No. 14/558,631, Notice of Allowance dated Jun. 21, 2018, 7 pages.
Co-Pending U.S. Appl. No. 14/808,679, Restriction Requirement dated Mar. 19, 2018, 7 pages.
Co-Pending U.S. Appl. No. 14/808,679, Non-Final Office Action dated Sep. 10, 2018, 12 pages.
Co-Pending U.S. Appl. No. 14/808,679, Response to Mar. 19, 2018 Restriction Requirement dated May 21, 2018, 2 pages.
Co-pending U.S. Appl. No. 15/186,653, Notice of Allowance, dated Aug. 1, 2018, 7 pages.
Co-pending U.S. Appl. No. 15/424,335 Notice of Allowance dated Sep. 21, 2018, 7 pages.
Co-pending U.S. Appl. No. 15/881,414 Amendment and Petition for Priority Claim dated Jul. 26, 2018, 26 pages.
Co-pending U.S. Appl. No. 15/881,414 dated Apr. 26, 2018 Non-Final Office Action, 8 pages.
Co-pending U.S. Appl. No. 15/881,414 Corrected Notice of Allowability dated Nov. 13, 2018, 2 pages.
Co-pending U.S. Appl. No. 15/881,414 Notice of Allowance dated Oct. 24, 2018, 7 pages.
Co-pending U.S. Appl. No. 15/881,414 Petition Decision dated Oct. 9, 2018, 9 pages.
Co-pending U.S. Appl. No. 16/177,745 filed Nov. 1, 2018.
Co-Pending U.S. Appl. No. 13/550,307, Aug. 13, 2018 Applicant-Initiated Interview Summary, 3 pages.
Co-Pending U.S. Appl. No. 13/550,307, Final Office Action dated Dec. 5, 2018, 17 pages.
Co-Pending U.S. Appl. No. 13/550,307, Response to Mar. 14, 2018 Non-Final Office Action dated Jul. 16, 2018, 12 pages.
Co-Pending U.S. Appl. No. 13/958,152, Non-Final Office Action dated Oct. 18, 2018, 20 pages.
Co-Pending U.S. Appl. No. 14/627,046, Amendment dated Jun. 29, 2017, 8 pages.
Co-Pending U.S. Appl. No. 14/1627,046, Interview Summary dated dated Apr. 27, 2018, 3 pages.
Co-Pending U.S. Appl. No. 14/627,046, Notice of Allowance dated Sep. 19, 2018, 7 pages.
Co-Pending U.S. Appl. No. 14/627,046, Rule 132 Affidavit and Response to Feb. 15, 2018 Non-Final Office Action, dated Jun. 15, 2018, 13 pages.
Co-Pending U.S. Appl. No. 14/686,380, Response to May 9, 2018 Final Office Action with RCE, dated Aug. 30, 2018, 14 pages.
Co-pending U.S. Appl. No. 16/152,743, filed Oct. 5, 2018.
Co-Pending U.S. Appl. No. 14/558,631, Response to Jan. 8, 2018 Non-Final Office Action dated Apr. 9, 2018, 8 pages.
Co-pending U.S. Appl. No. 15/424,335 Non-Final Office Action dated Apr. 26, 2018, 9 pages.
Co-pending U.S. Appl. No. 15/843,888, filed Dec. 15, 2017.
Co-pending U.S. Appl. No. 15/881,414, filed Jan. 26, 2018.
Co-Pending U.S. Appl. No. 13/550,307, Non-Final Office Action dated Mar. 14, 2018, 18 pages.
Co-Pending U.S. Appl. No. 13/958,152, Response to Dec. 22, 2017 Final Office Action dated Mar. 22, 2018, 10 pages.
Co-Pending U.S. Appl. No. 14/627,046, Non-Final Office Action dated Feb. 15, 2018, 12 pages.
Co-Pending U.S. Appl. No. 14/686,380, Final Office Action dated May 9, 2018, 14 pages.
Co-Pending U.S. Appl. No. 14/686,380, Response to Nov. 22, 2017 Non-Final Office Action dated Mar. 28, 2018, 11 pages.
Kotnik et al., "Sensitivity of transmembrane voltage induced by applied electric fields—A theoretical analysis", Bioelectrochemistry and Bioenergetics, vol. 43, Issue 2, 1997, pp. 285-291.

\* cited by examiner

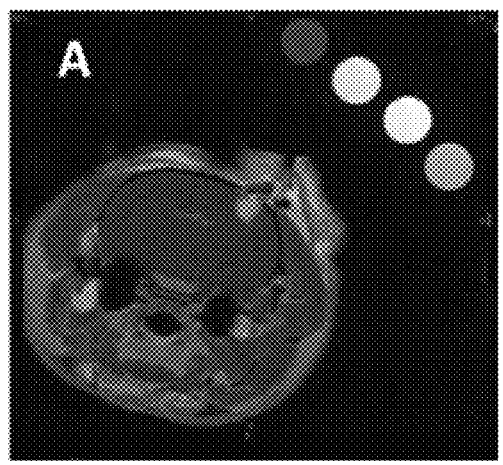
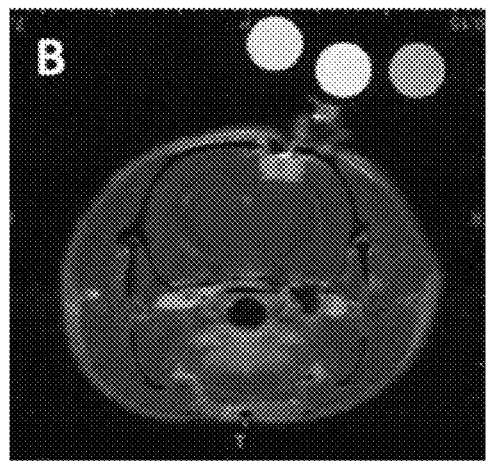
FIG. 8A  FIG. 8B
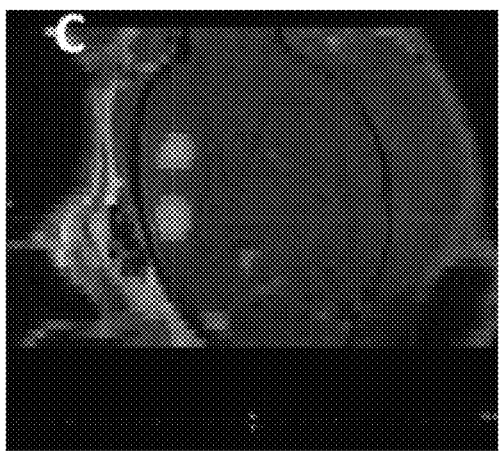
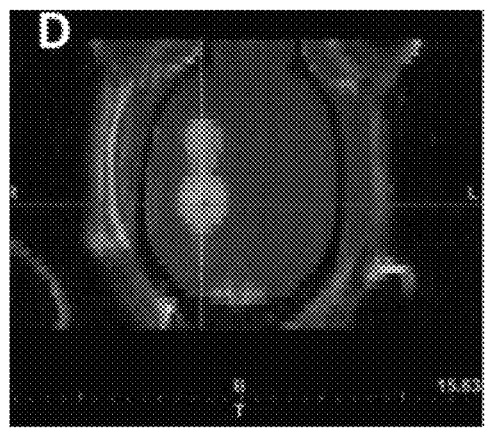
FIG. 8C  FIG. 8D

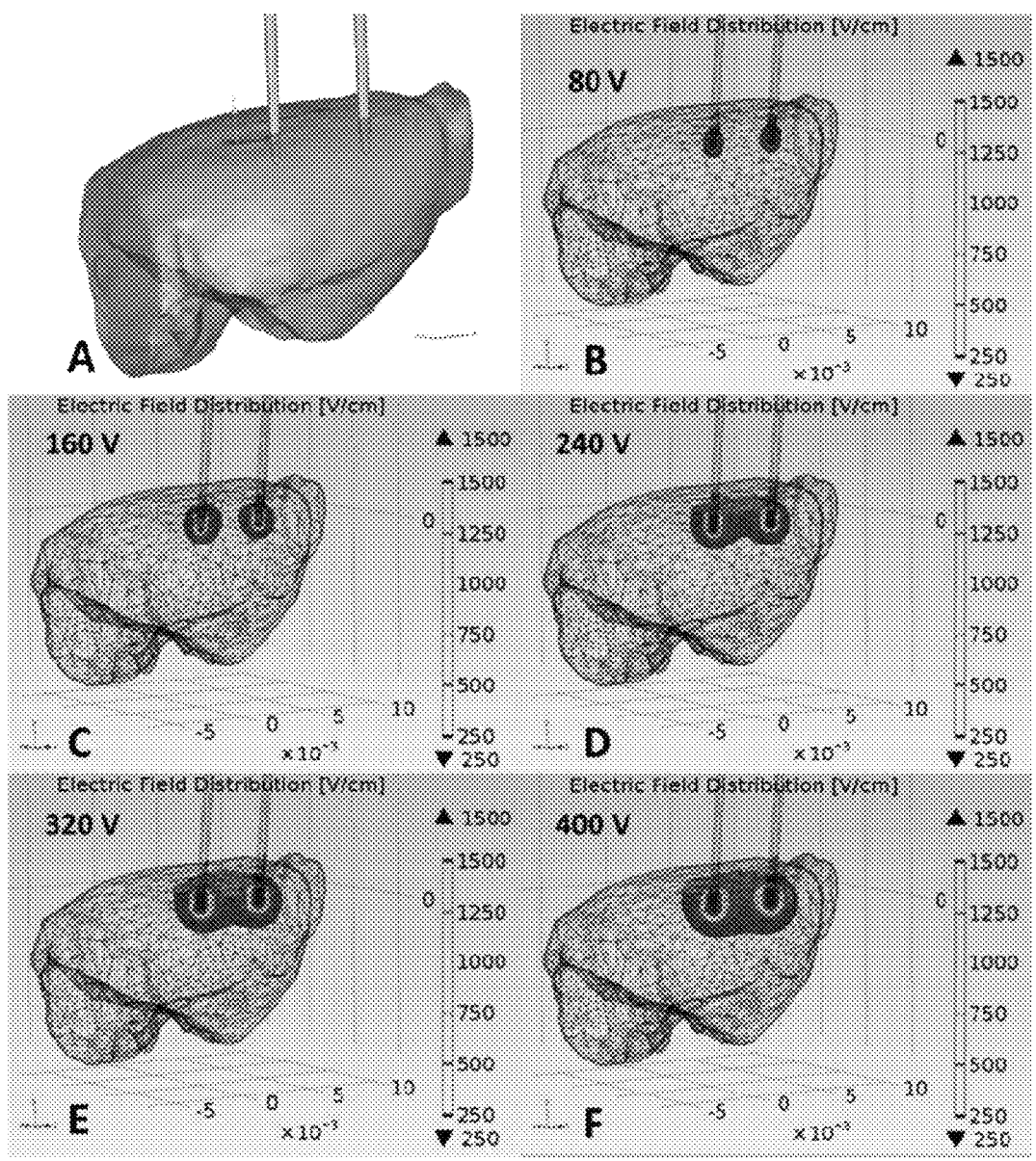
FIGS. 11A-F

ACUTE BLOOD-BRAIN BARRIER DISRUPTION USING ELECTRICAL ENERGY BASED THERAPY

CROSS-REFERENCE TO RELATED APPLICATIONS

The present application is a Continuation-in-Part application of parent application U.S. patent application Ser. No. 12/491,151, filed on Jun. 24, 2009, which published as U.S. Patent Application Publication No. 2010/0030211 on Feb. 4, 2010 and issued as U.S. Pat. No. 8,992,517 on Mar. 31, 2015, which relies on and claims the benefit of the filing dates of U.S. Provisional Patent Application Nos. 61/171, 564, filed Apr. 22, 2009, 61/167,997, filed Apr. 9, 2009, and 61/075,216, filed Jun. 24, 2008, which parent application is a Continuation-in-Part application of U.S. patent application Ser. No. 12/432,295, filed on Apr. 29, 2009, which published as U.S. Patent Application Publication No. 2009/0269317 on Oct. 29, 2009 and issued as U.S. Pat. No. 9,598,691 on Mar. 21, 2017, which relies on and claims the benefit of the filing date of U.S. Provisional Patent Application No. 61/125,840, filed Apr. 29, 2008. This application also relies on the disclosure of and claims priority to and the benefit of the filing date of U.S. Provisional Application No. 61/695,705, filed Aug. 31, 2012. The disclosures of these patent applications are hereby incorporated by reference in their entireties. Additionally, the present application is a Continuation-in-Part application of U.S. patent application Ser. No. 13/550,307, filed Jul. 16, 2012, which published as U.S. Patent Application Publication No. 2013/0184702 on Jul. 18, 2013.

BACKGROUND OF THE INVENTION

Field of the Invention

The present invention relates to the field of medical therapies involving administering electrical treatment energy, as well as the field of drug delivery. Embodiments of the invention provide electrical energy based methods for temporarily disrupting the blood-brain-barrier for increasing intracellular delivery of drugs across the blood-brain barrier. Generally, the present invention provides for a combination of an electroporation-based therapy such as ECT, EGT, and IRE with the administration of therapeutic and diagnostic agents to cause the uptake of these agents into brain tissue. More specifically, embodiments of the invention provide electrical energy based therapies for disrupting the blood-brain barrier in a manner sufficient for delivering chemotherapeutic agents across the blood-brain barrier surrounding a zone of ablation. Methods of the invention are useful for treating and/or diagnosing brain tumors.

Description of Related Art

In spite of aggressive therapy, the median survival for the majority of patients with glioblastoma multiforme (GBM) is approximately 15 months (Stupp R, Mason WP, van den Bent M J, Weller M, Fisher B, et al. (2005) Radiotherapy plus concomitant and adjuvant temozolomide for glioblastoma. N Engl J Med 352: 987-996). One of the reasons for poor survival is that tumor cells diffusely infiltrate the brain parenchyma (Hochberg F H, Pruitt A (1980) Assumptions in the radiotherapy of glioblastoma. Neurology 30: 907-911). Effective treatment of GBM may be limited by inefficient intracellular delivery of chemotherapy. Most agents demonstrating in vitro cytotoxic effects against glial tumors do not cross the blood-brain-barrier (BBB) in vivo.

A number of attempts have been made to circumvent the blood-brain barrier to deliver therapeutic agents to undesirable tissue such as brain tumors. Among these are intrathecal injections, surgical implants, and osmotic techniques. Intrathecal injection allows sustained delivery of agents directly into brain ventricles and spinal fluid through infusion pumps implanted surgically. Osmotic approaches involve intraarterial injection of mannitol to cause endothelial cells forming the barrier to shrink, causing brief disruptions of the barrier. However, both these techniques carry the risk of severe side effects, including seizures during or after the procedure.

Although the BBB is compromised in portions of GBM, there is convincing evidence that these heterogeneous tumors frequently contain areas of infiltrative tumor which do not show enhancement, and therefore which are not likely affected by systemic chemotherapeutic agents (Barajas R F, Jr., Phillips J J, Parvataneni R, Molinaro A, Essock-Burns E, et al. (2012) Regional variation in histopathologic features of tumor specimens from treatment-naive glioblastoma correlates with anatomic and physiologic MR Imaging. Neuro Oncol 14: 942-954; Saraswathy S, Crawford F, Lamborn K, Pirzkall A, Chang S, et al. (2009) Evaluation of MR markers that predict survival in patients with newly diagnosed GBM prior to adjuvant therapy. Journal of Neuro-Oncology 91: 69-81). A technique that uniformly increases BBB permeability and therefore delivery of cytotoxic agents into tumors, may yield improved tumor control (Liu H L, Hua M Y, Chen P Y, Chu P C, Pan C H, et al. (2010) Blood-brain barrier disruption with focused ultrasound enhances delivery of chemotherapeutic drugs for glioblastoma treatment. Radiology 255: 415-425 ("Liu et al., 2010")).

Electrochemotherapy (ECT) is a technique that uses pulsed electric fields to facilitate the uptake of chemotherapeutic agents, which then induces tumor cell death (Marty M, Sersa G, Garbay J R, Gehl J, Collins C G, et al. (2006) Electrochemotherapy—An easy, highly effective and safe treatment of cutaneous and subcutaneous metastases: Results of ESOPE (European Standard Operating Procedures of Electrochemotherapy) study. European Journal of Cancer Supplements 4: 3-13; Salford L G, Persson B R, Brun A, Ceberg C P, Kongstad P C, et al. (1993) A new brain tumour therapy combining bleomycin with in vivo electropermeabilization. Biochem Biophys Res Commun 194: 938-943; Agerholm-Larsen B, Iversen H K, Ibsen P, Moller J M, Mahmood F, et al. (2011) Preclinical Validation of Electrochemotherapy as an Effective Treatment for Brain Tumors. Cancer Research 71: 3753-3762).

Therapeutic irreversible electroporation (IRE) is an emerging technology that also uses pulsed electric fields to produce non-thermal ablation of tumors (Al-Sakere B, Andre F, Bernat C, Connault E, Opolon P, et al. (2007) Tumor ablation with irreversible electroporation. PLoS ONE 2: e1135 ("Al-Sakere et al., 2007"); Davalos R V, Mir L M, Rubinsky B (2005) Tissue ablation with irreversible electroporation. Ann Biomed Eng 33: 223-231; Edd J F, Horowitz L, Davalos R V, Mir L M, Rubinsky B (2006) In vivo results of a new focal tissue ablation technique: irreversible electroporation. IEEE Trans Biomed Eng 53: 1409-1415; Appelbaum L, Ben-David E, Sosna J, Nissenbaum Y, Goldberg S N (2012) US Findings after Irreversible Electroporation Ablation: Radiologic-Pathologic Correlation. Radiology 262: 117-125). IRE creates a sharply delineated volume of ablated tissue, with sub-millimeter resolution (Ben-David E, Appelbaum L, Sosna J, Nissenbaum I, Goldberg S N (2012) Characterization of Irreversible Electroporation Ablation in In vivo Porcine Liver. Am J Roentgenol 198: W62-W68). IRE treatments involve inserting needle-like electrodes into the tumor and delivering a series of low-energy pulses to permanently destabilize the cell membranes, inducing death without thermal damage (Al-Sakere et al., 2007; Davalos R V, Rubinsky B (2008) Temperature considerations during irreversible electroporation. International Journal of Heat and Mass Transfer 51: 5617-5622). IRE primarily affects the cell membrane of target cells, sparing important tissue components such as major blood vessels and extracellular matrix (Lee E W, Loh C T, Kee S T (2007) Imaging guided percutaneous irreversible electroporation: ultrasound and immunohistological correlation. Technol Cancer Res Treat 6: 287-294).

It has been demonstrated that IRE safely disrupts the BBB and precisely ablates normal and neoplastic brain tissue (Garcia P A, Rossmeisl J H Jr, Robertson J, Ellis T L, Davalos R V: Pilot study of irreversible electroporation for intracranial surgery. Conf Proc IEEE Eng Med Biol Soc 2009:6513-6516, 2009 (Abstract); Ellis T L, Garcia P A, Rossmeisl J H, Jr., Henao-Guerrero N, Robertson J, et al. (2011) Nonthermal irreversible electroporation for intracranial surgical applications. Laboratory investigation. J Neurosurg 114: 681-688 ("Ellis et al., 2011"); Garcia P A, Rossmeisl J H, Neal II R E, Ellis T L, Olson J, et al. (2010) Intracranial nonthermal irreversible electroporation: In vivo analysis. J Membr Biol 236: 127-136 ("Garcia et al., 2010"); Garcia P A, Pancotto T, Rossmeisl J H, Henao-Guerrero N, Gustafson N R, et al. (2011) Non-thermal irreversible electroporation (N-TIRE) and adjuvant fractionated radiotherapeutic multimodal therapy for intracranial malignant glioma in a canine patient. Technol Cancer Res Treat 10: 73-83 ("Garcia et al., 2011"); Hjouj M, Last D, Guez D, Daniels D, Lavee J, et al. (2011) Electroporation-Induced BBB Disruption and Tissue Damage Depicted by MRI. Neuro-Oncology 13: 114).

It is believed that there is a minimal electric field at which BBB disruption occurs surrounding an IRE-induced zone of ablation and that this transient response can be measured using Gd uptake as a surrogate marker for BBB disruption (Liu et al., 2010; Frigeni V, Miragoli L, Grotti A, Lorusso V (2001) Comparative Study Between Gadobenate Dimeglumine and Gadobutrol in Rats with Brain Ischemia: Evaluation of Somatosensory Evoked Potentials. Investigative Radiology 36: 561-572 ("Frigeni et al., 2001"); Noce A L, Frigeni V, Demicheli F, Miragoli L, Tirone P (1999) Neurotolerability of Gadobenate Dimeglumine in a Rat Model of Focal Brain Ischemia: EEG Evaluation. Investigative Radiology 34: 262 ("Noce et al., 1999"); Köhrmann M, Struffert T, Frenzel T, Schwab S, Doerfler A (2012) The Hyperintense Acute Reperfusion Marker on Fluid-Attenuated Inversion Recovery Magnetic Resonance Imaging Is Caused by Gadolinium in the Cerebrospinal Fluid. Stroke 43: 259-261 ("Köhrmann et al., 2012")). This phenomenon may be used to improve delivery of otherwise poorly diffusible antitumoral agents across the BBB into regions containing microscopic glioma infiltrates. Thus, irreversible electroporation in combination with pharmacotherapy may be a much more effective treatment for GBM due to its ability to destroy tumor cells within a discrete zone while increasing susceptibility to exogenous agents outside the zone of ablation. Using IRE to destroy the tumor and/or increase the delivery of therapeutic agents to facilitate treatment of surrounding "at risk" tumor margins may therefore result in improved tumor control by treating the area in which most recurrences occur.

SUMMARY OF THE INVENTION

The present invention provides electrical energy based methods wherein pulsed electric fields are delivered into brain tissue (such as a tumor) of an animal, to cause temporary disruption of the Blood-Brain-Barrier (BBB) in a volume of brain tissue in the vicinity of the source of the pulsed electric fields over an interval, and wherein an agent is administered to the animal so that it is present in blood to provide for uptake of the agent into the volume of brain tissue in which the BBB is disrupted over the interval.

In one embodiment, the invention provides a method of delivering an agent, such as an exogenous agent, to a volume of brain tissue of an animal through disruption of the blood-brain barrier, comprising one or more or a combination of: a. administering an exogenous agent to the animal; b. inserting a probe into or proximal brain tissue of the animal; and c. delivering pulsed electric fields through the probe. In embodiments, the pulsed electric fields can be administered in a manner that reversibly disrupts the blood-brain barrier for an interval in a volume of brain tissue in the vicinity of the probe. Additionally, the agent is administered to the animal at such a time wherein the agent is present in the blood during the interval of blood-brain barrier disruption, such that it may cross the blood-brain barrier and be delivered to the volume of brain tissue in the vicinity of the probe/electrode during the period of disruption.

Methods within the scope of the invention include a method for ablating brain tissue of a living mammal comprising: placing first and second electrodes in a brain of the living mammal; applying a plurality of electrical pulses through the first and second placed electrodes which are predetermined to: cause irreversible electroporation (IRE) of brain tissue of the mammal within a target ablation zone; and cause a temporary disruption of a blood brain barrier (BBB) within a surrounding zone that surrounds the target ablation zone to allow material in a blood vessel to be transferred to the surrounding zone through the temporarily disrupted BBB.

Such methods can further comprise delivering large molecule material within a blood vessel of the brain, the large molecule being sufficiently large to be blocked by the BBB from passing through the blood vessel. In embodiments, the large molecule material is delivered to the blood vessel prior to applying the plurality of electrical pulses. Specific embodiments include wherein the large molecule includes a chemotherapeutic agent.

Methods of the invention can further comprise, after applying the plurality of electrical pulses, detecting the occurrence of IRE in the target ablation zone and temporary BBB disruption in the surrounding zone.

The step of applying can include applying each electrical pulse as a direct current pulse having a pulse duration of at least 5 microseconds. For example, in embodiments, the step of applying can include applying each electrical pulse as a direct current pulse having a pulse duration of between 5 and 100 microseconds.

In embodiments, the step of applying can include applying the plurality of pulses which are predetermined to be: sufficiently strong to cause non-thermal irreversible electroporation (NTIRE) of the brain tissue within the target ablation zone; and sufficiently strong to cause a temporary disruption of BBB within the surrounding zone, but insufficient to cause NTIRE in the surrounding zone.

The target tissue, such as brain tissue, is a tumor in or near the brain, such as glioblastoma multiforme.

The pulsed electric fields can be used to deliver electrical energy that is at a level that provides reversible electroporation, electrochemotherapy, electrogenetherapy, irreversible electroporation, and/or supraporation. Electrical pulses used in the methods, systems, and devices of the invention can have a waveform which is square, triangular, trapezoidal, exponential decay, sawtooth, sinusoidal, or of alternating polarity, or comprise a combination of one or more waveforms. For example, embodiments of the invention can comprise devices, systems, and methods operably configured such that one or more electrical pulse characterized by any one or more of the following can be administered: (a) an amplitude in the range of about 10 V/cm to about 6000 V/cm; (b) a duration in the range of about 10 ns to about 10 seconds; (c) a DC pulse or an AC signal with a frequency in the range of about 1 Hz to about 10 MHz; or (d) a number of pulses in the range of about 1 to about 1000.

Methods of the invention can include ablating a tumor, an anatomical structure, or target tissue at least partially or completely using irreversible electroporation.

In embodiments of the invention, the material such as an active agent is a bioactive agent. The material or bioactive agent can be at least one cancer therapeutic agent chosen from one or more of a chemotherapy agent, a targeted cancer therapy agent, a differentiating therapy agent, a hormone therapy agent, and an immunotherapy agent. The bioactive agent can be a combination of cancer therapeutic agents.

According to various embodiments, the agent can be a diagnostic agent, such as an imaging agent.

Methods of the invention include administering the agent or material before, during, simultaneously with, or after the electrical energy based therapy is applied.

The agent can be administered at a selected dose, route of administration, and/or timing to provide a therapeutic concentration of the agent in blood during the interval of blood-brain barrier disruption.

In embodiments of the invention, the pulsed electric fields are delivered through the probe at a voltage-to-distance ratio of at least about 50 V/cm up to about 5,000 V/cm. For example, the electrical energy based therapy can be administered at a voltage-to-distance ratio of at least about 200 V/cm, 400 V/cm, 600 V/cm, 800 V/cm, or 1000 V/cm, or any combination thereof. Further, for example, the pulsed electric fields can be delivered at a voltage-to-distance ratio ranging from about 200-1000 V/cm.

According to embodiments, the pulsed electric fields can be delivered through the probe at a cycle time of about 1 Hz.

In embodiments of the invention, the pulsed electric fields are delivered through the probe such that the length of the pulses is in the range of about 10 microseconds to about 90 microseconds.

In embodiments of the invention, the pulsed electric fields are delivered through the probe such that the length of the pulses is about 50 microseconds.

In embodiments of the invention, the pulsed electric fields are delivered such that the number of pulses is about 8 or more, such as about 80 pulses or more, or for example about 90 pulses or more.

In embodiments of the invention, the animal is a laboratory animal selected from the group consisting of a rat, mouse, hamster, a cat, a dog, a sheep, a Cynomolgus macaque, a Rhesus macaque, a common marmoset, a squirrel monkey, an olive baboon, a vervet monkey, a night monkey, or a chimpanzee. Further, for example, according to the invention the animal can be an animal under veterinary care including a cat, a dog, a sheep, a goat, a horse, a cow, or an exotic animal. In embodiments of the invention, the animal is a human subject, or a human under a physician's care.

In embodiments of the invention, the volume of brain tissue in vicinity of the electrode is parenchyma.

In embodiments of the invention, the exogenous agent is a small molecule, a radioisotope, a natural protein, a synthetic protein, a natural peptide, synthetic peptide, a peptidomimetic, an antibody, an antibody fragment, an antibody conjugate, a small interfering RNA (siRNA), an antisense RNA, an aptamer, a ribozyme, an oligonucleotide, a viral vector, or an engineered cell.

In embodiments of the invention, the exogenous agent is administered to the animal through a route of administration chosen from one or more of parenteral, intravenous, intraarterial, intradermal, transdermal, intranasal, intraperitoneal, intramuscular, buccal, oral, and transmucosal.

Systems are also included within the scope of the invention, such as a system for ablating brain tissue of a living mammal comprising: a voltage generator operable to generate a plurality of electrical pulses between first and second electrodes; and a treatment planning module adapted to control the voltage generator to generate the plurality of pulses which are predetermined to: cause irreversible electroporation (IRE) of brain tissue of the mammal within a target ablation zone; and cause a temporary disruption of a blood brain barrier (BBB) within a surrounding zone that surrounds the target ablation zone to allow material in a blood vessel to be transferred to the surrounding zone through the temporarily disrupted BBB.

Such systems can further comprise a detector that detects the occurrence of IRE in the target ablation zone and temporary BBB disruption in the surrounding zone.

Additionally or alternatively, the treatment planning module of such systems can be adapted to control the voltage generator to generate each electrical pulse as a direct current pulse having a pulse duration of at least 5 microseconds. For example, the treatment planning module in embodiments can be adapted to control the voltage generator to generate each electrical pulse as a direct current pulse having a pulse duration of between 5 and 100 microseconds.

Even further, included within the scope of the invention is a system for ablating brain tissue of a living mammal comprising: a voltage generator operable to generate a plurality of electrical pulses between first and second electrodes; a memory; a processor coupled to the memory; and a treatment planning module stored in the memory and executable by the processor, the treatment planning module adapted to control the voltage generator to generate the plurality of pulses which are predetermined to be: sufficiently strong to cause non-thermal irreversible electroporation (NTIRE) of brain tissue of the mammal within a target ablation zone; and sufficiently strong to cause a temporary disruption of a blood brain barrier (BBB) within a surrounding zone that surrounds the target ablation zone, but insufficient to cause NTIRE in the surrounding zone, to allow material in a blood vessel to be transferred to the surrounding zone through the temporarily disrupted BBB.

Such systems can further comprise a detector that detects the occurrence of IRE in the target ablation zone and temporary BBB disruption in the surrounding zone.

In embodiments, the systems can be configured such that the treatment planning module is adapted to control the voltage generator to generate each electrical pulse as a direct current pulse having a pulse duration of at least 5 microseconds. For example, the treatment planning module can be adapted to control the voltage generator to generate each electrical pulse as a direct current pulse having a pulse duration of between 5 and 100 microseconds.

Additional embodiments, features, and advantages of the invention can be found in the foregoing Detailed Description of Various Embodiments of the Invention.

BRIEF DESCRIPTION OF THE DRAWINGS

The accompanying drawings illustrate certain aspects of embodiments of the present invention, and should not be used to limit or define the invention. Together with the written description the drawings serve to explain certain principles of the invention.

FIGS. 8A-8H are magnetic resonance images of brain sections showing qualitative representations of IRE-induced BBB disruption and in particular, 2D IRE lesion tracing on the coronal (FIG. 8A, FIG. 8B), dorsal (FIG. 8C, FIG. 8D), and sagittal (FIG. 8E, FIG. 8F) planes with the corresponding non-contiguous (FIG. 8G) and contiguous (FIG. 8H) 3D reconstruction zones of ablation representative of 400 V/cm and 1000 V/cm IRE treatments, respectively.

FIG. 10B compares the volume of IRE ablation with the volume of temperature elevated to at least 50° C. FIG. 10C displays the cross-sectional areas of IRE ablation (H&E), BBB disruption (Gd in MRI), and elevated temperatures (T≥50° C.) surrounding the rostral electrode as described in Table 2.

FIGS. 11A-11F are the electric field distributions (FIGS. 11B-F) using the 3D MRI reconstruction (FIG. 11A) of a rat brain. FIGS. 11B-11F display the electric field threshold necessary for match the volume of BBB disruption as measured experimentally with the Gd enhancement in the 7.0-T in vivo MRI. The required electric field to achieve BBB disruption was 298 V/cm (9.07 mm$^3$), 328 V/cm (19.83 mm$^3$), 406 V/cm (24.61 mm$^3$), and 476 V/cm (27.69 mm$^3$) for the 400, 600, 800, and 1000 V/cm IRE treatments, respectively. Note: Due to the 4-mm separation distance between the electrodes, a 400 V pulse represents a 1000 V/cm voltage-to-distance ratio.

DETAILED DESCRIPTION OF VARIOUS EMBODIMENTS OF THE INVENTION

Figure 1:
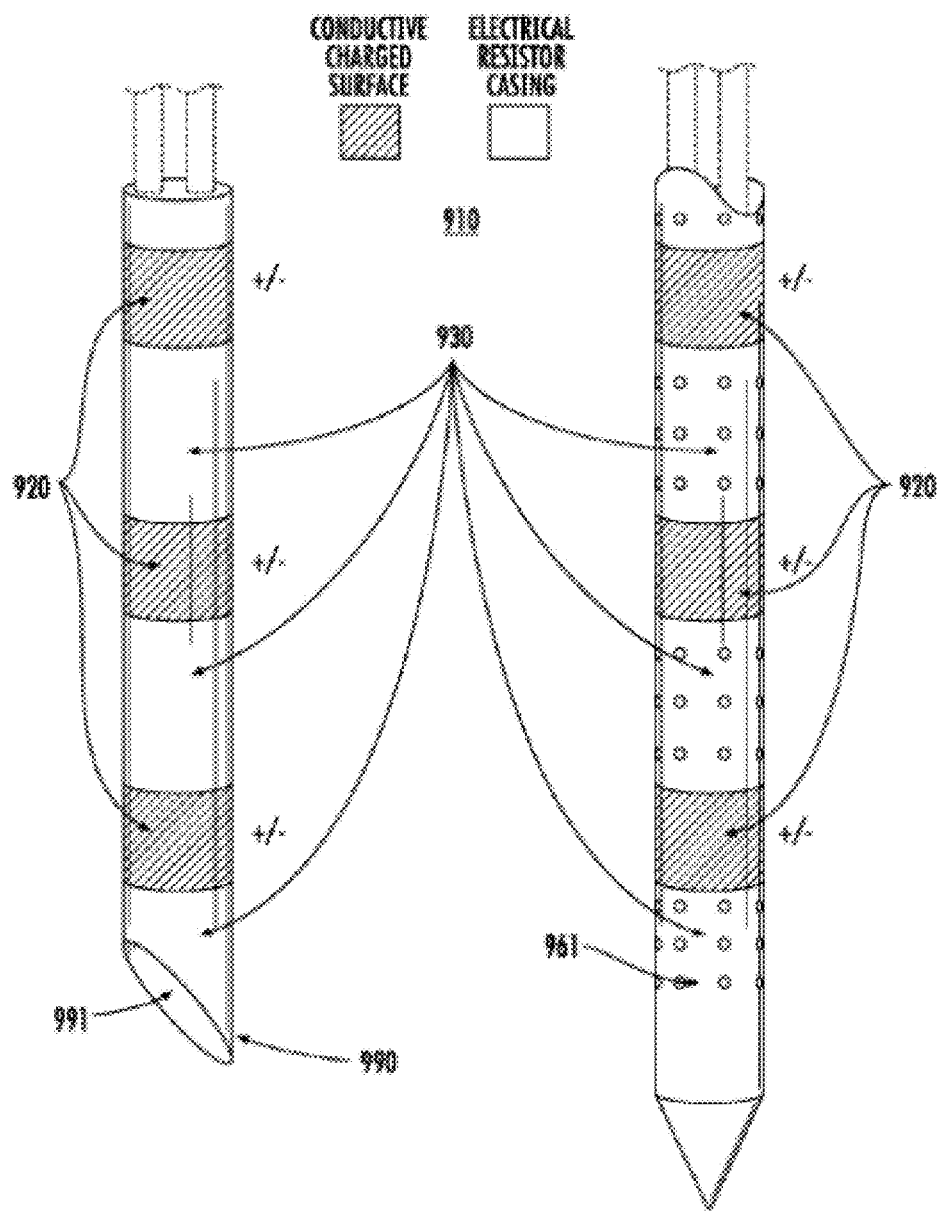
FIG. 1 is a schematic diagram of a hollow core device according to embodiments of the invention.

Reference will now be made in detail to various exemplary embodiments of the invention. However, the embodiments described in the description and shown in the figures are illustrative only and are not intended to limit the scope of the invention, and changes may be made in the specific embodiments described in this specification and accompanying drawings that a person of ordinary skill in the art will recognize are within the scope and spirit of the invention.

Throughout the present teachings, any and all of the one, two, or more features and/or components disclosed or suggested herein, explicitly or implicitly, may be practiced and/or implemented in any combination of two, three, or more thereof, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the inventions presented herein or in any future applications claiming priority to the instant application.

In one embodiment, the present invention provides a method of delivering an exogenous agent to a volume of brain tissue of an animal through disruption of the BBB, comprising: a. administering an agent to the animal, such as an exogenous agent; b. advancing a probe with an energizable electrode into or adjacent brain tissue of the animal; and c. delivering one or more pulsed electric fields through the probe; wherein: d. the pulsed electric fields reversibly disrupt the BBB for an interval in a volume of brain tissue in the vicinity of the probe; and e. the agent is administered to the animal at such a time wherein the agent is present in the blood during the interval of BBB disruption, such that the agent is capable of crossing the BBB and capable of being delivered to the volume of brain tissue in the vicinity of the electrode during the period of disruption. According to embodiments, the pulsed electric fields are of a magnitude and duration capable of administering IRE to a target tissue within the volume of brain tissue.

The animal can be any vertebrate or craniate. In one aspect, the animal is a laboratory animal including, without limitation, a rodent (e.g. rat, mouse, hamster), a cat, a dog, a sheep, or a non-human primate (e.g. Cynomolgus macaque, Rhesus macaque, common marmoset, squirrel monkey, olive baboon, vervet monkey (also known as grivet or African green monkey), and night monkey (also known as owl monkey), or chimpanzee). In another aspect, the animal is an animal under veterinary care, including a companion animal such as a cat or a dog, or a farm animal such as a sheep, a goat, a horse, a cow, or an exotic animal. In another aspect, the animal is a human such as a human under medical care (i.e., a human subject or patient).

The pulsed electric fields can deliver energy that is below the threshold for creating a zone of ablation, or greater than the threshold for creating a zone of ablation. In other words, the pulsed electric fields may deliver energy that is below the threshold for irreversible electroporation (e.g., at a level providing reversible electroporation or blood-brain-barrier disruption), or greater than the threshold for irreversible electroporation. If the pulsed electric fields provide a level of energy suitable for blood-brain-barrier disruption, they may be provided at a level suitable for delivery of chemicals or genes (e.g., electrochemotherapy (ECT) or electrogenetherapy (EGT)).

In a preferred embodiment, the pulsed electric fields delivery energy to brain tissue that is greater than the threshold for irreversible electroporation. In one aspect, the energy delivered to brain tissue is an electric field distribution. The electric field distribution may be influenced by factors such as the geometry (e.g., shape, diameter, and length) and positioning of the electrodes, the dielectric properties of the brain tissue to be treated, and the applied voltage. Such factors determine whether the electric field distribution is sufficient for irreversible electroporation.

The target tissue within the volume of brain tissue is preferably undesirable tissue such as a tumor. Examples of tumors that may be treated with the present invention include, without limitation, Astrocytic tumors (e.g. Subependymal giant cell astrocytoma, Pilocytic astrocytoma, Pilomyxoid astrocytoma, Diffuse astrocytoma, Pleomorphic xanthoastrocytoma, Anaplastic astrocytoma, Glioblastoma, Giant cell glioblastoma, Gliosarcoma), Oligondendroglial tumors (e.g. Oligodendroglioma, Anaplastic oligodendroglioma), Oligoastrocytic tumors (e.g. Oligoastrocytoma, Anaplastic oligoastrocytoma), Ependymal tumor (e.g. Subependymoma, Myxopapillary ependymoma, Ependymoma, Anaplastic ependymoma), Choroid plexus tumors (e.g. Choroid plexus papilloma, Atypical choroid plexus papilloma, Choroid plexus carcinoma), Other neuroepithelial tumors (e.g. Angiocentric glioma, Chordoid glioma of the third ventricle), Neuronal and mixed neuronal-glial tumors (e.g. Gangliocytoma, Ganglioglioma, Anaplastic ganglioma, Desmoplastic infantile astrocytoma and ganglioglioma, Dysembryoplastic neuroepithelial tumor, Central neurocytoma, Extraventricular neurocytoma, Cerebellar liponeurocytoma, Paraganglioma of the spinal cord, Papillary glioneuronal tumor, Rosette-forming glioneural tumor of the fourth ventricle), Pineal tumors (e.g. Pineocytoma, Pineal parenchymal tumor of intermediate differentiation, Pineoblastoma, Papillary tumor of the pineal region), Embryonal tumors (e.g. Medulloblastoma, CNS primitive neuroectodermal tumor (PNET), Atypical teratoid/rhabdoid tumor) Tumors of the cranial and paraspinal nerves (e.g. Schwannoma, Neurofibroma, Perineurioma, Malignant peripheral nerve sheath tumor (MPNST), Meningeal tumors (e.g. Meningioma, Atypical meningioma, Anaplastic/malignant meningioma, Hemangiopericytoma, Anaplastic hemangiopericytoma, Hemangioblastoma), and tumors of the sellar region (e.g. Craniopharyngioma, Granular cell tumor of the neurohypophysis, Pituicytoma, Spindle cell oncocytoma of the adenohypophysis). Brain tumors may also include metastases from primary tumors originating from tissues and organs outside the brain, including but not limited to breast, ovary, prostate, lung, liver, colon, bladder, kidney, and skin. It is conceived that the present invention may be used to treat any tumor of the central nervous system classified by the World Health Organization in any edition of such classification, such as the 2007 edition (Louis, D N, Ohgaki H, Wiestler, O D, Cavenee, W K. World Health Organization Classification of Tumours of the Nervous System. IARC, Lyon, 2007). In a preferred embodiment, the present invention is used to treat glioblastoma multiforme.

The present invention extends and improves on prior electroporation-based therapies (EBT) by providing new methods for electroporation-based treatment of tumors of the brain. Tumors of the brain such as glioblastoma multiforme have poor survival in part because the regions surrounding the solid tumor may contain diffuse infiltrations of tumor cells in the brain parenchyma. While IRE is effective in treating solid tumors, it may spare the killing of infiltrating tumor cells in these regions. Further, because the brain is protected by the BBB, a number of therapeutic and diagnostic agents are unable to be taken up into brain tumor cells using conventional techniques. As demonstrated in the Examples, the present inventors have found that delivery of pulsed electric fields through irreversible electroporation causes a transient disruption in the BBB (e.g., using voltage-to-distance ratios of 200 V/cm to 1000 V/cm) in regions surrounding the zone of ablation. The extent and duration of BBB disruption was positively correlated with electric field strength and occurred even at electric field strengths in which electroporation was predominately or exclusively reversible. The irreversible electroporation protocols resulted in the uptake of both low and higher molecular weight agents, indicating increased BBB permeability to solutes, ions, and protein. Thus, the present invention provides for a combination of an electroporation-based therapy such as ECT, EGT, and IRE with the administration of therapeutic and diagnostic agents to cause the uptake of these agents into brain tissue. Embodiments of the present invention include therapeutic methods that employ IRE in combination with an exogenous agent to kill undesirable cells (e.g. infiltrating tumor cells) in the vicinity of treated tumors (e.g. tumor margins).

In general, the present invention is a method providing 1) pulsed electric fields into brain tissue (such as a tumor) of an animal, to cause temporary disruption of the BBB in a volume of brain tissue in the vicinity of the source of the pulsed electric fields over an interval and 2) administration of an exogenous agent to the animal so that it is present in blood to provide for uptake of the agent into the volume of brain tissue in which the BBB is disrupted over the interval.

As provided in the Examples, the volume of brain tissue and duration in which the BBB is disrupted positively correlates with electric field strength of the pulsed electric fields. Thus, the skilled artisan can design protocols to target a particular volume of tissue to be treated with an exogenous agent through adjusting the voltage-to-distance ratio used in the protocol, among any other parameters involved in the treatment. In a preferred embodiment, the voltage-to-distance ratio is sufficient to cause partial or complete ablation of brain tumor through IRE, and treat a volume of brain tissue in the vicinity of the treated tumor (e.g. tumor margin) with an exogenous agent, such as a cancer therapeutic agent.

Devices, systems, and methods for causing partial or complete ablation of a brain tumor through IRE are known, and have been described in part in U.S. Patent Application Publication No. 2010/0030211 A1, which the present application is a Continuation-in-Part application of. Thus, the following description will demonstrate the present invention as it applies to methods of treating a brain tumor with IRE.

In general, methods of treating with IRE comprise temporarily implanting or disposing one or more electrodes, which may be present on the same or different devices, into or immediately adjacent a tumor, and applying an electrical field to the tumor in multiple pulses or bursts over a prescribed or predetermined period of time to cause irreversible cell death to some or all of the tumor cells. Preferably, irreversible damage to non-tumor cells in proximity to the tumor is minimal and does not result in significant or long-lasting damage to healthy tissues or organs (or a significant number of cells of those tissues or organs). According to methods of the invention, cell killing is predominantly, essentially, or completely due to non-thermal effects of the electrical pulsing. Methods can further comprise removing the electrode(s) after suitable treatment with the electrical fields. As a general matter, because the methods involve temporary implantation of relatively small electrodes, it is minimally invasive and does not result in the need for significant post-treatment procedures or care. Likewise, it does not result in significant ancillary or collateral damage to the subject being treated.

In practicing the methods, the number of electrodes, either on a single or multiple devices, used can be selected by the practitioner based on the size and shape of the tumor to be treated and the size and shape of the electrode. Thus, embodiments of the invention include the use of one, two, three, four, five, six, seven, eight, nine, ten or more electrodes. Each electrode can be independently sized, shaped, and positioned in or adjacent the tumor to be treated. In addition, the number and spacing of electrodes on a single device can be adjusted as desired. As detailed below, the location, shape, and size of electrodes can be selected to produce three-dimensional killing zones of numerous shapes and sizes, allowing for non-thermal treatment of tumors of varying shapes and sizes.

In embodiments, pulse durations for ablation of solid tumors can be relatively short, thus reducing the probability of generation of thermal conditions and excessive charges that cause collateral damage to healthy tissues. More specifically, the present invention recognizes that, the pulse length for highly efficient tissue ablation can be lower than 100 microseconds (100 µs). Indeed, it has surprisingly been determined that a pulse length of 25 us or lower can successfully cause non-thermal cell death. Thus, in embodiments, the methods of treatment can use pulse lengths of 10 µs, 15 µs, 20 µs, 25 µs, 30 µs, 35 µs, 40 µs, 45 µs, 50 µs, 55 µs, 60 µs, 65 µs, 70 µs, 75 us, 80 µs, 85 µs, or 90 µs. Preferably, to most effectively minimize peripheral damage due to heat, pulse lengths are limited to 90 µs or less, for example 50 µs or less, such as 25 µs. By reducing the pulse length, as compared to prior art techniques for IRE, larger electric fields can be applied to the treatment area while avoiding thermal damage to non-target tissue (as well as to target tissue). As a result of the decreased pulse length and concomitant reduction in heat production, the methods of the invention allow for treatment of tissues having higher volumes (e.g., larger tumors) than possible if prior art methods were to be employed for in vivo treatment of tumors.

In exemplary embodiments, the pulse duration of the electroporation-based therapy can exceed 100 µs. Any length pulse or pulse train can be administered in embodiments according to the invention. For example, pulse lengths of about 1 picosecond to 100 seconds can be used, such as from 10 picoseconds to about 10 seconds, or for example from about 100 picoseconds to about 1 second, or from 1 nanosecond to 100 milliseconds, or from about 10 nanoseconds to about 10 milliseconds, or from about 100 nanoseconds to about 1 millisecond, or from about 1 microsecond or 10 microseconds to about 100 microseconds. It is preferred in some embodiments to have a pulse length ranging from about 100 microseconds to about 1 second, such as a pulse length of about 110, or 120, or 130, or 140, or 150, or 200, or 300, or 350, or 400, 500, or 600, or 700, or 800 or 900 microseconds, or about 1, 2, 3, 4, 5, 6, 7, 8, 9, or 10 milliseconds, or even 15, 20, 30, 40, 50, 60, 70, 80, 90, or 100 milliseconds, or even for example from about 200, 300, 400, 500, 600, 700, 800, or 900 milliseconds and so on.

It has also been determined that voltages traditionally used for IRE are too high for beneficial treatment of tumors in situ. For example, typically, IRE is performed using voltages of between 4000 V/cm to 1500 V/cm. The present invention provides for use of voltages of much lower power. For example, the present methods can be performed using less than 1500 V/cm. Experiments performed by the inventors have shown that 2000 V/cm at greater than or equal to 1 cm between electrodes can cause excessive edema and stroke in patients when applied to brain tissue. Advantageously, for treatment of brain tumors, applied fields of about 500 V/cm to 1000 V/cm are used. Thus, in general for treatment of brain tumors, applied fields of less than 1000 V/cm can be used.

In embodiments of methods of the invention, the electroporation-based therapy is provided at a higher energy than conventional electroporation-based therapies. In an exemplary embodiment, the amplitude of the pulses of the electroporation-based therapy exceeds 2000 V/cm, including an amplitude of about 2200 V/cm, or 2500 V/cm, such as about 3000 V/cm, or 3500 V/cm, or about 4000 V/cm, such as 4500 V/cm, or about 5000 V/cm, such as about 5500 V/cm, or about 6000 V/cm, or about 6500 V/cm, such as about 7000 V/cm, or about 7500 V/cm, such as 8000 V/cm, or about 8500 V/cm, including 9000 V/cm, or about 9500 V/cm, such as about 10,000 V/cm and so on.

Further, it has been discovered that the number of electrical pulses that can be applied to successfully treat tumors can be quite high. The present invention provides for the use of a relatively high number of pulses, on the order of 90 pulses or greater. For example, in exemplary embodiments, 90 pulses are used. Other embodiments include the use of more than 90 pulses, such as 100 pulses, 110 pulses, or more. In exemplary embodiments, the number of pulses of the electroporation-based therapy can exceed 100. According to embodiments, the number of pulses can range from about 5 to about 400 pulses, such as from about 10 to about 350 pulses, or for example from about 15 to about 300 pulses, including from about 20 to about 250 pulses, or from about 25 to about 200 pulses, such as from about 30 to about 150 pulses, for example from about 50 to about 125 pulses, such as from about 75 to about 175 pulses, or from about 90 to 110 pulses, such as about 100 pulses.

According to methods of the invention, cycle times for pulses are set generally about 1 Hz. Furthermore, it has been found that alternating polarity of adjacent electrodes minimizes charge build up and provides a more uniform treatment zone. More specifically, in experiments performed by the inventors, a superficial focal ablative IRE lesion was created in the cranial aspect of the temporal lobe (ectosylvian gyrus) using the NanoKnife® (Angiodynamics, Queensbury, N.Y.) generator, blunt tip bipolar electrode (Angiodynamics, No. 204002XX) by delivering 9 sets of ten 50 us pulses (voltage-to-distance ratio 2000 V/cm) with alternating polarity between the sets to prevent charge build-up on the stainless steel electrode surfaces. These parameters were determined from ex-vivo experiments on canine brain and they ensured that the charge delivered during the procedure was lower than the charge delivered to the human brain during electroconvulsive therapy (an FDA approved treatment for major depression). Excessive charge delivery to the brain can induce memory loss, and thus is preferably avoided.

In exemplary embodiments, the pulse rate of the electroporation-based therapy can exceed 1 Hz. Specific method embodiments may employ administering electroporation based therapy using a pulse rate of about 1 Hz to 20 GHz, such as for example from about 10 Hz to 20 GHz, or about 50 Hz to 500 Hz, or 100 Hz to 1 kHz, or 10 kHz to 100 kHz, or from 250 kHz to 10 MHz, or 500 kHz to 1 MHz, such as from 900 kHz to 2 MHz, or from about 100 MHz to about 10 GHz, including from about 200 MHz to about 15 GHz and so on.

The present invention provides advancements over conventional tissue electroporation by utilizing high-frequency, bipolar pulses. Pulsing protocols according to embodiments of the invention involve bursts of bipolar pulses with a burst width on the order of microseconds and duration of single polarity on the microsecond to nanosecond scale. The total burst width of the high-frequency pulses (~100-1000 ns duration of single polarity) is on the order of hundreds of microseconds, the time delay in between bursts is on the order of seconds, and the total number of bursts can be adjusted. In addition to being bipolar, the pulses can have a duration of single polarity (~1 μs) that is two orders of magnitude less than the duration of a conventional electroporation pulse (~100 μs). For example, a first positive electrical pulse can be initiated and at a desired time following administration of the first pulse, a second pulse equal in magnitude to the first pulse but opposite in charge can be initiated. Also, the positive and negative applied voltages do not have to be of equal magnitude.

A delay can be included between pulses within the train, or the total number of pulses within the train can be controlled, to limit the Joule heating in the tissue while still delivering a lethal dose of energy. The repetition rate of pulse trains can also be controlled to minimize interference with, and allow treatment of vital organs that respond to electrical signals, such as the heart.

According to embodiments, the delay between pulses is on the order of microseconds and the delay between bursts is on the order of seconds, such as administering two or more electric pulse bursts with a delay between bursts on the order of seconds. An example treatment plan can include 12, 1 ms pulses separated by a delay of 1 s. Further, for example, a burst width of a bipolar waveform that includes delays can be twice as long (40 μs) as the corresponding burst with no delays in order to generate an equivalent pulse on-time (20 μs).

For example, a time delay between pulses can be any desired duration as well, including from 5 times the pulse length, to 3 times the pulse length, to 1 time the pulse length, to no delay (or effectively no delay).

Appropriate electrical fields and durations of exposure are those that have been reported in the literature as being suitable for medical treatment of tissues for tumor ablation. Exemplary exposure parameters include: ninety 90 microsecond (μs) pulses at 1.5 kV/cm at a frequency of 1 Hz; eighty 100 μs pulses at 2.5 kV/cm at a frequency of 1 Hz; one 20 millisecond pulse at 400 V/cm; ten 100 μs pulses at 3800 V/cm at a frequency of 10 pulses per second; ninety 100 μs pulses ranging from 1000 to 1667 V/cm at a frequency of about 1 Hz; and eighty pulses of 100 μs ranging from 1000 to 3000 V/cm at about 1 Hz. In general, the frequency of pulsing can be as low as twice the pulse width and can be quite a bit farther apart. Any suitable frequency that allows for electroporation without significant thermal damage to the tissue is acceptable. Furthermore, electrical current can be supplied as either DC or AC.

High-frequency, bipolar waveforms are also included in embodiments of the invention for mitigating or completely eliminating muscle contractions during electroporation based therapies. It is well known in the field of functional electrical stimulation that the threshold for nerve stimulation increases as the center frequency of bipolar waveforms increases. Further, muscle twitch forces are reduced as frequency increases. The present invention demonstrates that a range of frequencies exist where non-thermal tissue ablation can be achieved without causing nerve excitation or muscle contraction. In the context of this specification, it is noted that the term ablation is used to indicate destruction of cells, but not necessarily destruction of the supportive stroma.

Clinically, this translates to performing IRE without the requirement of paralytic agents (or a reduction in the amount of paralytic agents administered) in all procedures, and without the further requirement of general anesthesia in minimally invasive procedures. Additionally, other complications caused by IRE with unipolar electric pulses are alleviated, including electrode displacement and pain associated with intense muscle contractions.

The present invention applies to all electroporation based therapies. Recently, electroporation has been utilized in vivo as a means to destroy cancer cells within tissues in both reversible and irreversible modalities. Reversible electroporation is being studied to facilitate the delivery of anticancer drugs and DNA into cancer cells through the plasma membrane in the form of electrochemotherapy (ECT) and electrogenetherapy (EGT), respectively. Irreversible electroporation (IRE) promotes cell death resulting in the development of a tissue lesion. It is an independent means to ablate substantial volumes of targeted tissue without the use of harmful adjuvant chemicals if used prior to the onset of thermal injury. See Davalos 2005. By not relying on thermal processes, IRE has been shown to spare the extracellular matrix and architecture of nerves and blood vessels.

Included in embodiments of the invention is a method of treating a subject suffering from a neoplasia comprising: implanting at least one device for emitting electric pulses into or adjacent a neoplastic site within the body of a subject; and delivering one or more electric pulse to the neoplastic site, such that amplitude and duration of the pulse are in the range of about 1500 V/cm to 2500 V/cm for 10 μs or less which is capable of inducing irreversible electroporation. Methods of the invention also include non-invasive methods of treating a subject comprising non-invasively placing at least one device for emitting electric pulses around a region of the body containing a neoplastic site within; and delivering one or more electric pulse, such that amplitude and duration of the pulse are in the range of about 1500 V/cm to 2500 V/cm for 10 μs or less which is capable of inducing irreversible electroporation.

According to embodiments of the invention, such methods can employ multiple pulses administered in a pulse burst having a duration of less than 10 ms.

Such methods can employ one or more pulses or a plurality of pulses in a pulsing protocol, wherein the amplitude of the pulse is in the range of about 500 V/cm to 1500 V/cm. Amplitude in the context of this specification refers to the voltage-distance ratio of a pulse, such as for 1500 V/cm the voltage is 750V over a distance of 0.5 cm.

Such methods can have a pulse duration in the range of about 2 MHz (250 ns) to about 500 kHz (1 μs). For example, the pulse duration can be about 1 MHz (500 ns). In preferred embodiments, the duration of each pulse is in the range of about 100 to 10,000 ns.

Any number of probes or electrodes can be used invasively, semi-invasively, or non-invasively according to embodiments of the invention. In preferred embodiments, two or more electrically conductive regions are used within a single device for emitting the electrical pulses. Similarly, in any of the methods according to the invention, two or more devices can be used to deliver multiple electric pulses at different positions within, on, or near a body.

Custom treatment area shapes can be created through varying electrode activation patterns in combination with any of the embodiments of the invention.

The methods can also employ delivery of a bipolar burst of pulses. In embodiments, a bipolar burst of pulses can be delivered with multiple pulses in a single phase before a polarity switch. Even further, total burst width of any pulse protocol according to the invention can be between 1 µs and 10,000 µs. In preferred embodiments, the methods can have a duration of single polarity within a bipolar burst of between about 100 ns and 100,000 ns.

The shape of the electric pulses delivered using methods of the invention can be square, ramp, sinusoidal, exponential, or trapezoidal.

In preferred embodiments, two or more electric pulse bursts can be administered with a delay between bursts. In preferred embodiments, a delay between bursts can be on the order of seconds. For example, in bipolar protocols a selected positive voltage (+V) can be applied for a selected period of time (e.g., 50 µs), then a zero voltage applied for a selected period of time (e.g., 75 µs), then a negative voltage (−V) can be applied (e.g., 50 µs). The voltage can be applied in any number of individual pulses, as a pulse or pulse burst. Instructions for implementing the treatment protocols can comprise specifying a number of bipolar pulses to be delivered, a length of pulse duration, and a length of any delay between pulses.

Also included in embodiments of the invention is a method of delivering electric pulses such that amplitude and duration of single polarity are selected to be capable of administering electroporation to electrically excitable tissue without stimulation of the tissue.

Further included is a method of delivering electric pulses such that amplitude and duration of single polarity are selected to be capable of administering electroporation to electrically excitable tissue with reduced stimulation of the tissue as compared with higher amplitude and longer duration pulse protocols. Preferably tissue stimulation that is avoided or prevented refers to a muscle contraction.

In embodiments, the neoplastic site, region of the body, or electrically excitable tissue can be nerve tissue, muscle, or an organ containing nerves and/or muscle tissue.

Any embodiment of the invention can employ applying electric pulses having an amplitude and duration in the range of about 1500 V/cm to 2500 V/cm for 10 ms or less which is capable of inducing irreversible electroporation.

Method embodiments of the invention can be used to build up the transmembrane potential of a tissue to a critical value (~1V) by delivering trains of less than 1 µs bipolar pulses. For example, multiple monopolar pulses can be delivered at a pulse duration of about 5 MHz prior to a polarity switch, then delivered at a pulse duration of about 5 MHz after polarity switch.

Methods of the invention may or may not employ administering of a drug designed to induce a neural blockade. The methods can include administration of general, local, or no anesthesia for treatment of tissues with electroporation based therapies. In preferred embodiments, no neural blockade is required for treatment of tissues with electroporation based therapies, or lower dosages of a neural blockade can be used in embodiments of the invention to achieve the same results as using higher doses with lower frequency pulsing protocols.

The pulses of any method of the invention can be delivered on a short enough timescale to flow through epithelial cells but are long enough to induce electroporation in underlying cells. In specific embodiments, a frequency of 500 kHz or 1 MHz or 250 kHz is used to treat underlying fat cells in a layer of fat disposed under the epidermis.

Methods according to the invention can be modified to provide for administering non-thermal IRE, IRE, and/or reversible electroporation.

Non-thermal IRE is a method to kill undesirable cells using electric fields in tissue while preserving the ECM, blood vessels, and nerves. Certain electrical fields, when applied across a cell, have the ability to permeabilize the cell membrane through a process that has come to be called "electroporation". When electrical fields permeabilize the cell membrane temporarily, after which the cells survive, the process is known as "reversible electroporation". Reversible electroporation has become an important tool in biotechnology and medicine. Other electrical fields can cause the cell membrane to become permeabilized, after which the cells die. This deadly process is known as "irreversible electroporation". Non-thermal irreversible electroporation is a new, minimally invasive surgical technique to ablate undesirable tissue, for example, tumor tissue. The technique is easy to apply, can be monitored and controlled, is not affected by local blood flow, and does not require the use of adjuvant drugs. The minimally invasive procedure involves placing needle-like electrodes into or around the targeted area to deliver a series of short and intense electric pulses that induce structural changes in the cell membranes that promote cell death. The voltages are applied in order to electroporate tissue without inducing significant joule heating that would significantly damage major blood vessels and the ECM. For a specific tissue type and set of pulse conditions, the primary parameter determining the volume irreversibly electroporated is the electric field distribution within the tissue. Recent IRE animal experiments have verified the many beneficial effects resulting from this special mode of non-thermal cell ablation, such as preservation of major structures including the extracellular matrix, major blood vessels, and myelin sheaths, no scar formation, as well as its promotion of a beneficial immune response.

Treatment planning according to embodiments of the invention can result in more predictable outcomes in homogeneous and heterogeneous tissues than compared with lower frequency pulsing protocols.

Any one or more of the methods, devices, or systems, or parts thereof, can be combined with other methods, devices, systems, or parts thereof mentioned in this specification to obtain additional embodiments within the scope of this invention.

Devices and systems for implementing any one or more of the above mentioned methods are also within the scope of the invention.

The present invention provides an advancement over tissue ablation techniques previously devised by providing methods for precisely and rapidly killing diseased, damaged, disordered, or otherwise undesirable biological tissues in situ. More specifically, the present invention provides methods comprising electric pulse therapies for ablating target cells and tissues for the treatment of diseases and disorders. Surprisingly, it has been found that the use of ultra-short pulses that have the ability to cause cell death can be effective as a treatment process for aberrant cell growths. The inventors have developed electroporation techniques using nanosecond-scale pulses as a controlled, precise way to destroy aberrant cells of a tissue or organ, without the deleterious side effect of heating the healthy cells in the vicinity of the undesirable cells. In these methods, one or more electrodes are placed within, near, or around the targeted region to deliver a series of high energy electric pulses to promote cell death. The packing of cells within a tissue is largely heterogeneous, and most organs are covered with epithelial cells joined by tight junctions to form a continuous sheet that rests on a layer of fibrous connective tissue. Further, organs can contain multiple sites of epithelial cells within underlying layers of tissue, for example, the cells forming the lining of ducts. Tight junctions are the preferred sites for electroporation when microsecond-scale pulses longer than the charging time of the membrane are employed, because current is confined to the extracellular space once the surrounding cell membranes are fully charged. Therefore, the voltage drop and resulting electric field is larger across layers of tissue containing tight junctions where current pathways are reduced. This, in turn, reduces the amount of underlying tissue that can be treated. The epithelial layer acts as a shield, absorbing a majority of the voltage drop. This problem can be alleviated through the use of electric pulses with durations shorter than the charging time of plasma membranes, such as on the order of about 1-1,000 nanoseconds. Then it is possible for the field to reach the underlying layers of tissue, because current can flow through both the extracellular and intracellular spaces. All cells present in the organ, regardless of their packing, experience a homogenous electric field distribution. It is advantageous to tune the pattern of pulse delivery to the tissue of interest. Depending on electrode and tissue geometry, pulses can be "stacked" in a monopolar or bipolar train, and individual pulses within each train can be delivered from different electrodes, such that cell death only occurs in targeted regions where the integration of pulses both temporally and spatially yields electroporation. The present disclosure documents how electroporation can effectively be done with nanosecond pulses using a series of pulses (applied from differing electrode pairs or the same set).

For in vivo practice of the method, the debris remaining from the irreversibly permeabilized cells may be left in situ and may be removed by natural processes, such as the body's own circulation and immune system.

The advantages of electric pulse therapies over other ablation techniques lay within their ability to kill tissue through a non-thermal mechanism. The methods of the invention use electroporation to kill target cells while preserving the extracellular matrix, nerves, major blood vessels, and other sensitive structures of the treated tissues, enhancing treatment outcome. Furthermore, the ablation area can be predicted using numerical modeling for accurate treatment planning, and application of the procedure can be monitored in real-time using ultrasound and confirmed with both ultrasound and MRI, among other imaging techniques. The methods of the invention allow for killing of target cells and tissues, and exhibit rapid lesion creation and resolution, prompting the repopulation of the region with healthy cells. Though treatment success is not dependent upon the immune system, a tumor specific immune response capable of helping to destroy any residual micro-metastases occurs when the invention is practiced to kill tumor cells, decreasing the chances of recurrence.

In some embodiments, two or more electrodes are used to treat aberrant cell growth and effect cell death. The electrodes may be present on the same or different devices for delivering electrical pulses. Preferably, the parameters for electroporation are selected to minimize or avoid excessive heating of the treated tissue and surrounding tissue, thus reducing collateral damage to healthy tissue near the aberrant cell region. In some embodiments, discussed in more detail below, energized electrodes are distributed outside and about/around a subject and the grounded electrode is placed directly into the region where cells to be treated are found. In other embodiments, no ground electrode is necessary, making the entire procedure completely noninvasive.

The step of providing an electric charge involves applying an appropriate series of electrical pulses to the cells to be treated, where the pulses are characterized by being of relatively high voltage and relatively short duration. According to the invention, the electrical pulses have a duration that is less than the charging time of plasma membranes and have a voltage that is sufficient for cell killing but not so high as to cause substantial killing of surrounding, non-target, healthy cells by thermal heating. Because the method of treating can be applied to numerous cells, tissues, and organs, the precise pulse duration and voltage will vary depending on the particular application. However, pulse lengths in general are on the nanosecond range and voltages are at least about 500 V. Further guidance on selecting parameters is provided below.

It thus should be apparent that the present invention provides a method of treating a subject suffering from an aberrant cell growth, where the method comprises: implanting an electrode into or adjacent the aberrant growth region within the body of a subject, and causing multiple electrical pulses to be emitted from the electrode into the aberrant growth region in 10 microsecond or shorter pulses to cause predominantly non-thermal killing of aberrantly growing cells by IRE. In embodiments, the method uses pulses of between about 10,000 nanoseconds and about 1 picosecond. In embodiments, the electrical pulses are provided as a series of pulses of from 1 picosecond (ps) to 1,000 nanoseconds (ns) or higher (e.g., 10,000 ns) at voltages above about 500 V. Even further, in embodiments, durations of the electric pulses include less than 1 microsecond, such as less than 900 nanoseconds, less than 500 nanoseconds, less than 100 nanoseconds, and less than 50 nanoseconds. While no particular lower limit is envisioned, from a practical standpoint, pulse durations of greater than 1 picosecond is the current lower limit, due to device dimensions. Two or more electrodes can be used in the method and can be provided as part of a single device. In some embodiments, the method includes positioning the electrodes at a distance apart from each other to create custom treatment area shapes through varying electrode activation patterns. The methods of the invention can be used to treat neoplasias, such as leukemia or pancreatic cancer. The methods can be used to treat human subjects. Further, according to embodiments of the method, two or more electrodes are used, where one electrode is a current input electrode that is implanted in or adjacent an aberrant growth, and another electrode is a current return electrode that is implanted within the body of the subject at a site adjacent to or distant from the aberrant growth region, or is provided external to the subject. Of course, the alternative configuration can be implemented as well, where the implanted electrode is a return electrode and where a current input electrode is implanted within the body of the subject at a site adjacent to or distant from the aberrant growth region, or is provided external to the subject.

In some embodiments, the method results in a reduction in cell proliferation of the aberrant cells. In other embodiments, the method results in a reduction in the size of a tumor. Yet in other embodiments, the method results in ablation of a tumor.

The method can include emitting multiple electric pulses such that the temporal and spatial summation of such pulses results in the generation of an electric field of about 500 V/cm to 2500 V/cm for 10000 microseconds or less to induce IRE. Alternatively, the method can include emitting multiple electric pulses such that the temporal and spatial summation of such pulses results in the generation of an electric field of about 1 kV/cm to 50 kV/cm for 1000 nanoseconds or less to induce supra-poration in addition to IRE. It is to be recognized that, in various embodiments, the individual electric pulses can be monophasic while in other embodiments, the individual electric pulses can be biphasic. In certain preferred embodiments, a train of monophasic pulses is delivered in one direction, followed by a subsequent pulse train of opposite polarity. Depending on the outcome desired, the waveforms or the electric pulses are triangular, square, sinusoidal, exponential, or trapezoidal. Other geometric shapes are contemplated as well. In some embodiments, an electrode is connected to a system for employing electrical impedance tomography (EIT), computer tomography (CT), Magnetic Resonance Imaging (MRI), or ultrasound to image the tissue prior to treatment by applying small alternating currents that themselves do not damage the tissue.

In embodiments, the invention provides a method of treating a subject suffering from an aberrant cell growth, where the method comprises: contacting the subject with a first electrode, placing at least two additional electrodes outside the subject's body at positions that permit electrical charges to be delivered to the aberrant cell growth, and causing multiple electrical pulses to be emitted from one or more of the electrodes into the aberrant growth region in ten microsecond or shorter pulses to cause predominantly non-thermal killing of aberrantly growing cells by IRE. In certain embodiments, the step of contacting comprises contacting the first electrode with the skin of the subject, while in other embodiments, the step of contacting comprises implanting the first electrode at a site in the subject's body that is adjacent to the aberrant cell growth. Other embodiments contemplate different means of contacting, which will be evident to those of skill in the art without the need to list them herein.

The method can be considered to be a method of delivering an electric pulse through a layer using short pulses. For example, the layer can be bone, muscle, fat, connective tissue, nervous tissue, an endothelial layer, or any other layer present in a subject to be treated. According to some embodiments of the method of the invention, electrical pulses induce a combination of both IRE and supra-poration.

Yet again, the method of the invention can be considered a method of treating a subject suffering from an aberrant growth, where the method comprises: implanting an electrode into or adjacent the aberrant growth, and causing multiple electrical pulses to be emitted from the electrode into the aberrant growth in 10 microsecond or shorter pulses, where the electrical pulses cause reversible electroporation of cells of the aberrant growth and/or cells adjacent the aberrant growth, which results in uptake of bioactive substances into the treated cells.

In another general aspect, devices are provided for carrying out the method of the invention. Broadly speaking, the devices of the invention include one or more electrically conductive elements (i.e., electrodes) that can be used for electroporation induced cell killing of target cells within the body of a subject. In embodiments, the devices comprise one or more electrodes for reversible implantation into a subject and for delivering electrical pulses to target tissues and cells in the subject. In other embodiments, the devices comprise a combination of electrically conductive elements for combined delivery of electrical pulses, where one or more elements is designed for reversible implantation into the subject and one or more of the elements is designed for use external to the subject's body. In exemplary embodiments, the devices comprise at least one electrode for placement into the body of a subject and at least one electrically conductive element for placement outside of a subject, where the multiple elements/electrodes work in conjunction to deliver cell-killing nanosecond pulses to target tissues.

The present invention provides an advancement over tissue ablation techniques previously devised by providing methods for precisely and rapidly killing diseased, damaged, disordered, or otherwise undesirable biological tissues in situ. More specifically, the present invention provides methods comprising electric pulse therapies for ablating target cells and tissues for the treatment of diseases and disorders. Surprisingly, it has been found that the use of ultra-short pulses that have the ability to cause cell death can be effective as a treatment process for aberrant cell growths. The inventors have developed electroporation techniques using nanosecond-scale pulses as a controlled, precise way to destroy aberrant cells of a tissue or organ, without the deleterious side effect of heating the healthy cells in the vicinity of the undesirable cells. In these methods, one or more electrodes are placed within, near, or around the targeted region to deliver a series of high energy electric pulses to promote cell death. The packing of cells within a tissue is largely heterogeneous, and most organs are covered with epithelial cells joined by tight junctions to form a continuous sheet that rests on a layer of fibrous connective tissue. Further, organs can contain multiple sites of epithelial cells within underlying layers of tissue, for example, the cells forming the lining of ducts. Tight junctions are the preferred sites for electroporation when microsecond-scale pulses longer than the charging time of the membrane are employed, because current is confined to the extracellular space once the surrounding cell membranes are fully charged. Therefore, the voltage drop and resulting electric field is larger across layers of tissue containing tight junctions where current pathways are reduced. This, in turn, reduces the amount of underlying tissue that can be treated. The epithelial layer acts as a shield, absorbing a majority of the voltage drop. This problem can be alleviated through the use of electric pulses with durations shorter than the charging time of plasma membranes, such as on the order of about 1-1,000 nanoseconds. Then it is possible for the field to reach the underlying layers of tissue, because current can flow through both the extracellular and intracellular spaces. All cells present in the organ, regardless of their packing, experience a homogenous electric field distribution. It is advantageous to tune the pattern of pulse delivery to the tissue of interest. Depending on electrode and tissue geometry, pulses can be "stacked" in a monopolar or bipolar train, and individual pulses within each train can be delivered from different electrodes, such that cell death only occurs in targeted regions where the integration of pulses both temporally and spatially yields electroporation. The present disclosure documents how electroporation can effectively be done with nanosecond pulses using a series of pulses (applied from differing electrode pairs or the same set).

The methods of the invention comprise, in embodiments, treatment of tissue surrounding a site of aberrant cell growth.

In embodiments, this treatment causes cell killing of some healthy cells surrounding the aberrant cell growth. For example, in treating an invasive or aggressive tumor, it is often advisable to eliminate a zone of apparently healthy cells surrounding a tumor site to improve treatment outcome by destroying tumor cells that have invaded the healthy tissue outside of the defined tumor.

In other instances, treatment of tissue surrounding a site of aberrant cell growth includes causing reversible electroporation of cells of the surrounding tissue. The reversible electroporation can be an unavoidable consequence of the method, but can also be an intended result. In either case, reversible electroporation can be a mere side-effect of the treatment, or can be used as a secondary treatment. More specifically, reversible electroporation can be used to cause cells of healthy tissue surrounding an aberrant cell mass to have different physical and biochemical properties than it had prior to treatment. For example, bioactive agents can be introduced into the reversibly electroporated cells. The bioactive agents can be agents that cause the healthy cells to be killed. In such embodiments, additional cell killing, under controlled conditions, can be effected in healthy tissue. Alternatively, the bioactive agents can be agents that protect the cells from destruction, for example by immune cells that respond to the tissue injury resulting from the electroporation treatment of the aberrant cells.

The method of the invention can be part of a multi-modal treatment. The method thus may comprise other cell-killing techniques known in the art. For example, the method may further comprise exposing a tumor region to radiation, or treating the patient with a chemotherapeutic agent. It likewise may be performed after or between surgical intervention to remove all or part of a tumor region. Those of skill in the art are fully aware of the parameters for treatment with other modalities; thus, details of those treatment regimens need not be detailed herein.

The step of providing an electric charge involves applying an appropriate series of electrical pulses to the cells to be treated, where the pulses are characterized by being of relatively high voltage and relatively short duration. According to the invention, the electrical pulses have a duration that is less than the charging time of plasma membranes and have a voltage that is sufficient for cell killing but not so high as to cause substantial killing of surrounding, non-target, healthy cells by thermal heating. Because the method of treating can be applied to numerous cells, tissues, and organs, the precise pulse duration and voltage will vary depending on the particular application. However, pulse lengths in general are on the nanosecond range and voltages are at least about 500 V. Further guidance on selecting parameters is provided below.

The method of treating can be considered a method of treating an animal (including a human) having an aberrant cell growth or mass in or on a tissue or an organ. In exemplary embodiments, the organ is pancreas, brain, bone, heart, or any other organ where electrode puncture of the tissue or tissue heterogeneities limit the extent and predictability of conventional IRE or supra-poration treatment. Under this view, the method can be a method of treating an animal suffering from a disease or disorder resulting from aberrant cell growth by reducing or eliminating some or all of a region of aberrant cells (e.g., tumor). The method can also be a method of treating an animal suffering from a disease or disorder characterized by cell cycle dysfunctions, including cells that are not dying or undergoing apoptotic mechanisms of cell death or similar programmed cell death at appropriate, natural, or naturally induced times, such as those mediated through protein bindings or intracellular cascades. Likewise, the method can be a method of treating an animal suffering from a disease or disorder involving cells with alterations that allow for immune system evasion or immune system indifference.

It thus should be apparent that the present invention provides a method of treating a subject suffering from an aberrant cell growth, where the method comprises: implanting an electrode into or adjacent the aberrant growth region within the body of a subject, and causing multiple electrical pulses to be emitted from the electrode into the aberrant growth region in ten microsecond or shorter pulses to cause predominantly non-thermal killing of aberrantly growing cells by IRE. In embodiments, the method uses pulses of between about 10,000 nanoseconds and about 1 picosecond. Two or more electrodes can be used in the method and can be provided as part of a single device. In some embodiments, the method includes positioning the electrodes at a distance apart from each other to create custom treatment area shapes through varying electrode activation patterns. The methods of the invention can be used to treat neoplasias, such as leukemia or pancreatic cancer. The methods can be used to treat human subjects. Further, according to embodiments of the method, two or more electrodes are used, where one electrode is a current input electrode that is implanted in or adjacent an aberrant growth, and another electrode is a current return electrode that is implanted within the body of the subject at a site adjacent to or distant from the aberrant growth region, or is provided external to the subject. Of course, the alternative configuration can be implemented as well, where the implanted electrode is a return electrode and where a current input electrode is implanted within the body of the subject at a site adjacent to or distant from the aberrant growth region, or is provided external to the subject.

In some embodiments, the method results in a reduction in cell proliferation of the aberrant cells. In other embodiments, the method results in a reduction in the size of a tumor. Yet in other embodiments, the method results in ablation of a tumor.

In embodiments, the invention provides a method of treating a subject suffering from an aberrant cell growth, where the method comprises: contacting the subject with a first electrode, placing at least two additional electrodes outside the subject's body at positions that permit electrical charges to be delivered to the aberrant cell growth, and causing multiple electrical pulses to be emitted from one or more of the electrodes into the aberrant growth region in ten microsecond or shorter pulses to cause predominantly non-thermal killing of aberrantly growing cells by IRE. In certain embodiments, the step of contacting comprises contacting the first electrode with the skin of the subject, while in other embodiments, the step of contacting comprises implanting the first electrode at a site in the subject's body that is adjacent to the aberrant cell growth. Other embodiments contemplate different means of contacting, which will be evident to those of skill in the art without the need to list them herein.

The method can be considered to be a method of delivering an electric pulse through a layer using short pulses. For example, the layer can be bone, muscle, fat, connective tissue, nervous tissue, an endothelial layer, or any other layer present in a subject to be treated. According to some embodiments of the method of the invention, electrical pulses induce a combination of both IRE and supra-poration.

Yet again, the method of the invention can be considered a method of treating a subject suffering from an aberrant growth, where the method comprises: implanting an electrode into or adjacent the aberrant growth, and causing multiple electrical pulses to be emitted from the electrode into the aberrant growth in ten microsecond or shorter pulses, where the electrical pulses cause reversible electroporation of cells of the aberrant growth and/or cells adjacent the aberrant growth, which results in uptake of bioactive substances into the treated cells.

In another general aspect, devices are provided for carrying out the method of the invention. Broadly speaking, the devices of the invention include one or more electrically conductive elements (i.e., electrodes) that can be used for electroporation induced cell killing of target cells within the body of a subject. In embodiments, the devices comprise one or more electrodes for reversible implantation into a subject and for delivering electrical pulses to target tissues and cells in the subject. In other embodiments, the devices comprise a combination of electrically conductive elements for combined delivery of electrical pulses, where one or more elements is designed for reversible implantation into the subject and one or more of the elements is designed for use external to the subject's body. In exemplary embodiments, the devices comprise at least one electrode for placement into the body of a subject and at least one electrically conductive element for placement outside of a subject, where the multiple elements/electrodes work in conjunction to deliver cell-killing nanosecond pulses to target tissues.

The concept of alternating polarity of pulses can be extended to the use of multiple electrodes. For example, a combination of three electrodes can be used to deliver three sequential sets of alternating polarity pulses to a target tissue. More specifically, Electrode A can be used to deliver a 500 ns pulse at 1000 V at a starting time (T=0) and a 500 ns pulse at −1000 V at T=1 µs. Electrode B can be used to deliver a 500 ns pulse at 1000 V at T=500 ns, and a 500 ns pulse at −1000 V at T=1.5 µs. Electrode C can be used to deliver a 500 ns pulse at 1000 V at T=1 µs, and a −1000V pulse at T=2.0 µs. Of course, this concept can be applied using any numbers of electrodes and pulse times to achieve highly directed cell killing.

Methods of the invention encompass the use of multiple electrodes and different voltages applied for each electrode to precisely control the three-dimensional shape of the electric field for tissue ablation. More specifically, it has been found that varying the amount of electrical energy emitted by different electrodes placed in a tissue to be treated allows the practitioner to finely tune the three-dimensional shape of the electrical field that irreversibly disrupts cell membranes, causing cell death. Likewise, the polarity of electrodes can be varied to achieve different three-dimensional electrical fields. Furthermore, one of the advantages of embodiments of the invention is to generate electric field distributions that match complex tumor shapes by manipulating the potentials of multiple electrodes. In these embodiments, multiple electrodes are energized with different potential combinations, as opposed to an "on/off" system like radio frequency ablation, to maximize tumor treatment and minimize damage to surrounding healthy tissue.

For example, a treatment protocol according to the invention could include a plurality of electrodes. According to the desired treatment pattern, the plurality of electrodes can be disposed in various positions relative to one another. In a particular example, a plurality of electrodes can be disposed in a relatively circular pattern with a single electrode disposed in the interior of the circle, such as at approximately the center. Any configuration of electrodes is possible and the arrangement need not be circular but any shape periphery can be used depending on the area to be treated, including any regular or irregular polygon shape, including convex or concave polygon shapes. The single centrally located electrode can be a ground electrode while the other electrodes in the plurality can be energized. Any number of electrodes can be in the plurality such as from about 1 to 20. Indeed, even 3 electrodes can form a plurality of electrodes where one ground electrode is disposed between two electrodes capable of being energized, or 4 electrodes can be disposed in a manner to provide two electrode pairs (each pair comprising one ground and one electrode capable of being energized). During treatment, methods of treating can involve energizing the electrodes in any sequence, such as energizing one or more electrode simultaneously, and/or energizing one or more electrode in a particular sequence, such as sequentially, in an alternating pattern, in a skipping pattern, and/or energizing multiple electrodes but less than all electrodes simultaneously, for example.

According to methods of the invention, the separation of the electrodes within or about the tissue to be treated can be varied to provide a desired result. For example, the distance between two or more electrodes (whether ground or energizable) can be varied to achieve different three-dimensional electrical fields for irreversible disruption of cell membranes. Indeed, depending on the target region to be treated, the electrodes can be placed at a separation distance from one another ranging for example from 1 mm to about 10 cm, such as from 2 mm to about 5 cm, or from 3 mm to 2 cm, or from 5 mm to 1 cm, and so on. Any combination of number and placement of electrodes can be used for a particular treatment desired. The three-dimensional shape can thus be set to ablate diseased tissue, but partially or completely avoid healthy tissue in situations where the interface between healthy and diseased tissue shows a complex three dimensional shape.

Methods of embodiments of the invention may include, in addition to use of the electrodes and devices of the invention, other measures to further reduce the potential for thermal damage to non-target tissue. This may include, but is not limited to, use of a range of pulse durations, duty cycles and frequencies of pulse trains, amplitudes, number of pulses, voltages, pulse shapes, etc. that have been shown by the inventors to induce cell death in a target tissue while minimizing thermal damage to surrounding cells and tissue. Ranges that may be useful for the practice of methods of the invention are discussed in several U.S. patent applications and patents, including U.S. Patent Application Publication Nos. 2009/0269317, 2010/0030211, 2010/0331758, 2010/0261994, 2011/0106221, 2012/0109122, 2013/0184702; as well as U.S. Pat. Nos. 8,282,631 and 8,465,484, and International Patent Application Publication Nos. WO2009/134876, WO2010/151277, WO2010/118387, WO2011/047387, WO2012/071526, WO2012/088149, as well as U.S. patent application Ser. No. 14/012,832 entitled "System and Method for Estimating a Treatment Volume for Administering Electrical-Energy-Based Therapies," filed Aug. 28, 2013, and U.S. Published Patent Application No. 2010/0250209, entitled System and Method for Estimating a Treatment Region for a Medical Treatment Device, published Sep. 30, 2010, the disclosure of each of which is hereby incorporated by reference herein in its entirety.

The methods of the invention are well suited for treatment of tumors using non-thermal IRE. To better ensure that cell ablation is a result of non-thermal effect, and to better protect healthy tissue surrounding the site of treatment, the methods can further comprise cooling the electrodes during the treatment process. By applying a heat sink, such as a cooling element in an electrode (discussed below), generation of heat in and around tissue in close proximity to the electrodes can be minimized, resulting in a more consistent application of non-thermal IRE to the tissue and a more controlled application of cell killing to only those tissues desired to be treated.

The methods of the invention, in embodiments, include the use of electrodes of different sizes and shapes, including plate-type and/or needle-type (whether blunt tip or sharp tip) ground and/or energizable electrodes. In embodiments, the electrical field distribution may be altered by use of electrodes having different diameters, lengths, and shapes. Thus, the use of different sizes and shapes of conducting surfaces can be used to control the electrical fields used for cell ablation. In certain embodiments, the methods can include the use of a variable size electrode. For example, an electrode may be used that, in one configuration has a relatively small diameter, which is used for minimally invasive implantation of the electrode into the site to be treated. Once inserted, a sheath or other covering can be retracted to allow expansion of the electrode tip to a different size for application of the electric field. After treatment, the sheath can be moved to cover the tip again, thus reducing the size of the tip to its original size, and the electrode withdrawn from the treated tissue. The expandable element can be thought of as a balloon structure, which can have varying diameters and shapes, depending on original material shape and size.

In addition to treatment of brain tumors using non-thermal IRE, the methods of the invention further comprise administration of an exogenous agent to the animal, so that it is present in blood to provide for uptake of the agent into a volume of brain tissue surrounding the treated brain tumor. The surrounding tissue is exposed to the exogenous agent as a result of a period of disruption of the BBB in tissue surrounding ablated tumor tissue. This period of disruption is reversible such that the BBB will eventually be restored after the cessation of IRE. As such, exogenous agents such as bioactive or diagnostic agents can be introduced into the surrounding tissue during the period in which the BBB is disrupted. Such a treatment is preferred when treating highly aggressive malignant tumors, which often show invasion of as healthy tissue surrounding the tumor. In embodiments, the agent is administered to the subject parenterally.

The exogenous agent can be administered before, during, or after the EBT protocol (such as IRE) to provide an effective concentration of agent in the blood stream surrounding the volume of brain tissue during the period in which the BBB is disrupted. The exogenous agent may be a bioactive (e.g. therapeutic) agent or a diagnostic agent. The timing of administration of the exogenous agent can be determined by such factors as the pharmacokinetics of the agent according to the particularly route of administration in which the agent is administered. One of the advantages of the invention is that is not necessary to administer the exogenous agent through a local administration in the vicinity of the tumor to be treated, such as intrathecal; since the methods of the invention provide for disruption of the BBB, the exogenous agent may be administered systemically. For example, for an exogenous agent with a particularly short half-life, it may be desirable to administer the agent shortly before the IRE protocol through a route of administration that achieves rapid equilibration in the blood stream, such as intravenous administration. Typically, the route of administration is chosen based on the properties of the exogenous agent such as physicochemical characteristics, stability, and metabolism (e.g. half-life). Preferred are parenteral routes such as intravenous, intraarterial, intradermal, transdermal, intranasal, intraperitoneal, intramuscular, or buccal routes. Alternatively, administration may be the oral route or by application to mucous membranes. Preferably, the exogenous agent is administered so that it rapidly reaches the systemic circulation and thus the blood stream surrounding the volume of brain tissue to be treated. For an intravenous administration, the exogenous agent may be administered 5 minutes, 15 minutes, 0.5 hr, 1 hr, 2 hr, 4 hr, 8 hr, or 12 hr before the IRE protocol, depending on the type of exogenous agent used. For oral administration, the exogenous agent may be administered 12 hr, 24 hr, 36 hr, or 48 hr before the IRE protocol, depending for example on the rate of absorption of the exogenous agent. Preferably, the timing of administration of the exogenous agent is a such that it achieves $C_{max}$ (maximum (or peak) concentration) in blood after dosing at the time of the IRE protocol or within a short period of time after the IRE protocol, such as within 10, 20, 30, 45, or 60 minutes after the IRE protocol. This is because the duration of BBB disruption, as the Examples show, in embodiments may be on the order of minutes. However, it may be possible to extend this duration of BBB disruption by using higher voltages, or changing other parameters of the treatment. In other embodiments, when the exogenous agent is a bioactive (therapeutic) agent, it may be desired to administer multiple doses of the bioactive agent to build up a therapeutic concentration of the bioactive agent in blood. Additionally or alternatively, it may be desired to perform several doses of the EBT and/or administering of the exogenous agent to ensure an appropriate level of treatment is achieved. As approved bioactive agents such as cancer therapeutic agents undergo rigorous pharmacokinetic testing prior to approval, the skilled artisan may rely on such data to determine an appropriate dosage, route of administration, and timing of administration of the bioactive agent to provide a therapeutic concentration of the agent in blood during the duration of blood-brain-barrier disruption.

Additionally or alternatively there could be instances in which some of the potential adverse effects (e.g. edema) of BBB disruption may be treated with corticosteroids, mannitol, vascular endothelial growth factors (VEGF), chemical surfactants (e.g. neutral dextran), calcium channel blockers (e.g. nifedipine or verapamil), and/or amphiphilic tri-block copolymers (e.g. Poloxamer 188 (P188)).

The exogenous agent may be a small molecule, a radioisotope, a natural protein, a synthetic protein, a natural peptide, synthetic peptide, a peptidomimetic, an antibody, an antibody fragment, an antibody conjugate, a nucleic acid such as small interfering RNA (siRNA), antisense RNA, an aptamer, a ribozyme, or oligonucleotide, a viral vector comprising a nucleic acid sequence encoding a natural or synthetic bioactive protein peptide or serving as a vaccine to stimulate the immune system, or an engineered cell comprising such a viral vector. Preferably, the exogenous agent is a bioactive (e.g. therapeutic) agent comprising any of the above. As used herein, "bioactive agent" may also include a combination therapy employing two or more of any of the above, such as two or more small molecule therapies, a small molecule in combination with an antibody, a small molecule in combination with a viral vector, or any other combination.

In another aspect, the bioactive agent is a cancer therapeutic agent. In one embodiment, the bioactive agent is at least one cancer therapeutic agent selected from the group consisting of a chemotherapy agent, a targeted cancer therapy agent, a differentiating therapy agent, a hormone therapy agent, and an immunotherapy agent. Chemotherapy agents include alkylating agents, antimetabolites, anti-tumor antibiotics, topoisomerase inhibitors, mitotic inhibitors, corticosteroids, and the like. Targeted cancer therapy agents include signal transduction inhibitors (e.g. tyrosine kinase and growth factor receptor inhibitors), histone deacetylase (HDAC) inhibitors, retinoic receptor agonists, proteosome inhibitors, angiogenesis inhibitors, and monoclonal antibody conjugates. Differentiating therapy agents include retinoids, such as tretinoin and bexarotene. Hormone therapy agents include anti-estrogens, aromatase inhibitors, progestins, estrogens, anti-androgens, and GnRH agonists or analogs. Immunotherapy agents include monoclonal antibody therapies such as rituximab (RITUXAN) and alemtuzumab (CAMPATH), non-specific immunotherapies and adjuvants, such as BCG, interleukin-2 (IL-2), and interferon-alfa, immunomodulating drugs, for instance, thalidomide and lenalidomide (REVLIMID), and cancer vaccines such as PROVENGE. It is within the capabilities of a skilled artisan to chose an appropriate cancer therapeutic agent in the methods of the invention based on characteristics such as the type of tumor (e.g. primary brain tumor or metastatic), stage of the tumor, previous exposure to cancer therapeutic agents, and molecular characteristics. However, there should be a basis to believe that its efficacy for treating tumor cells will be enhanced by disruption of the BBB. For example, the skilled artisan would have a basis to choose an antibody therapeutic or chemotherapy agent with a large molecular weight such as TAXOL based on exclusion of such macromolecules by the BBB when it is normally intact. Similarly, other cancer therapeutic agents could be chosen based on a water or lipid solubility incompatible with BBB permeability.

In another embodiment, the bioactive agent is at least one cancer therapeutic agent selected from the group consisting of Abiraterone Acetate, ABITREXATE (Methotrexate), ABRAXANE (Paclitaxel Albumin-stabilized Nanoparticle Formulation), ADCETRIS (Brentuximab Vedotin), Ado-Trastuzumab Emtansine, ADRIAMYCIN (Doxorubicin Hydrochloride), ADRUCIL (Fluorouracil), Afatinib Dimaleate, AFINITOR (Everolimus), ALDARA (Imiquimod), Aldesleukin, Alemtuzumab, ALIMTA (Pemetrexed Disodium), ALOXI (Palonosetron Hydrochloride), AMBOCHLORIN (Chlorambucil), AMBOCLORIN (Chlorambucil), Aminolevulinic Acid, Anastrozole, Aprepitant, AREDIA (Pamidronate Disodium), ARIMIDEX (Anastrozole), AROMASIN (Exemestane), ARRANON (Nelarabine), Arsenic Trioxide, ARZERRA (Ofatumumab), Asparaginase *Erwinia chrysanthemi*, AVASTIN (Bevacizumab), Axitinib, Azacitidine, Bendamustine Hydrochloride, Bevacizumab, Bexarotene, BEXXAR (Tositumomab and I 131 Iodine Tositumomab), Bleomycin, Bortezomib, BOSULIF (Bosutinib), Cabazitaxel, Cabozantinib-S-Malate, CAMPATH (Alemtuzumab), CAMPTOSAR (Irinotecan Hydrochloride), Capecitabine, Carboplatin, Carfilzomib, CEENU (Lomustine), CERUBIDINE (Daunorubicin Hydrochloride), Cetuximab, Chlorambucil, Cisplatin, CLAFEN (Cyclophosphamide), Clofarabine, COMETRIQ (Cabozantinib-S-Malate), COSMEGEN (Dactinomycin), Crizotinib, Cyclophosphamide, CYFOS (Ifosfamide), Cytarabine, Dabrafenib, Dacarbazine, DACOGEN (Decitabine), Dactinomycin, Dasatinib, Daunorubicin Hydrochloride, Decitabine, Degarelix, Denileukin Diftitox, Denosumab, Dexrazoxane Hydrochloride, Docetaxel, Doxorubicin Hydrochloride, EFUDEX (Fluorouracil), ELITEK (Rasburicase), ELLENCE (Epirubicin Hydrochloride), ELOXATIN (Oxaliplatin), Eltrombopag Olamine, EMEND (Aprepitant), Enzalutamide, Epirubicin Hydrochloride, ERBITUX (Cetuximab), Eribulin Mesylate, ERIVEDGE (Vismodegib), Erlotinib Hydrochloride, ERWINAZE (Asparaginase *Erwinia chrysanthemi*), Etoposide, Everolimus, EVISTA (Raloxifene Hydrochloride), Exemestane, FARESTON (Toremifene), FASLODEX (Fulvestrant), FEMARA (Letrozole), Filgrastim, FLUDARA (Fludarabine Phosphate), Fludarabine Phosphate, FLUOROPLEX (Fluorouracil), Fluorouracil, FOLOTYN (Pralatrexate), Fulvestrant, Gefitinib, Gemcitabine Hydrochloride, Gemtuzumab Ozogamicin, GEMZAR (Gemcitabine Hydrochloride), GILOTRIF (Afatinib Dimaleate), GLEEVEC (Imatinib Mesylate), HALAVEN (Eribulin Mesylate), HERCEPTIN (Trastuzumab), HYCAMTIN (Topotecan Hydrochloride), Ibritumomab Tiuxetan, ICLUSIG (Ponatinib Hydrochloride), Ifosfamide, Imatinib Mesylate, Imiquimod, INLYTA (Axitinib), INTRON A (Recombinant Interferon Alfa-2b), Iodine 131 Tositumomab and Tositumomab, Ipilimumab, IRESSA (Gefitinib), Irinotecan Hydrochloride, ISTODAX (Romidepsin), Ixabepilone, JAKAFI (Ruxolitinib Phosphate), JEVTANA (Cabazitaxel), Kadcyla (Ado-Trastuzumab Emtansine), KEOXIFENE (Raloxifene Hydrochloride), KEPIVANCE (Palifermin), KYPROLIS (Carfilzomib), Lapatinib Ditosylate, Lenalidomide, Letrozole, Leucovorin Calcium, Leuprolide Acetate, Lomustine, LUPRON (Leuprolide Acetate, MARQIBO (Vincristine Sulfate Liposome), MATULANE (Procarbazine Hydrochloride), Mechlorethamine Hydrochloride, MEGACE (Megestrol Acetate), Megestrol Acetate, MEKINIST (Trametinib), Mercaptopurine, Mesna, METHAZOLASTONE (Temozolomide), Methotrexate, Mitomycin, MOZOBIL (Plerixafor), MUSTARGEN (Mechlorethamine Hydrochloride), MUTAMYCIN (Mitomycin C), MYLOSAR (Azacitidine), MYLOTARG (Gemtuzumab Ozogamicin), Nanoparticle Paclitaxel (Paclitaxel Albumin-stabilized Nanoparticle Formulation), NAVELBINE (Vinorelbine Tartrate), Nelarabine, NEOSAR (Cyclophosphamide), NEUPOGEN (Filgrastim), NEXAVAR (Sorafenib Tosylate), Nilotinib, NOLVADEX (Tamoxifen Citrate), NPLATE (Romiplostim), Ofatumumab, Omacetaxine Mepesuccinate, ONCASPAR (Pegaspargase), ONTAK (Denileukin Diftitox), Oxaliplatin, Paclitaxel, Paclitaxel Albumin-stabilized Nanoparticle Formulation, Palifermin, Palonosetron Hydrochloride, Pamidronate Disodium, Panitumumab, Pazopanib Hydrochloride, Pegaspargase, Peginterferon Alfa-2b, PEG-INTRON (Peginterferon Alfa-2b), Pemetrexed Disodium, Pertuzumab, PLATINOL (Cisplatin), PLATINOL-AQ (Cisplatin), Plerixafor, Pomalidomide, POMALYST (Pomalidomide), Ponatinib Hydrochloride, Pralatrexate, Prednisone, Procarbazine Hydrochloride, PROLEUKIN (Aldesleukin), PROLIA (Denosumab), PROMACTA (Eltrombopag Olamine), PROVENGE (Sipuleucel-T), PURINETHOL (Mercaptopurine), Radium 223 Dichloride, Raloxifene Hydrochloride, Rasburicas, Recombinant Interferon Alfa-2b, Regorafenib, REVLIMID (Lenalidomide), RHEUMATREX (Methotrexate), Rituximab, Romidepsin, Romiplostim, RUBIDOMYCIN (Daunorubicin Hydrochloride), Ruxolitinib Phosphat, Sipuleucel-T, Sorafenib Tosylate, SPRYCEL (Dasatinib), STIVARGA (Regorafenib), Sunitinib Malate, SUTENT (Sunitinib Malate), SYLATRON (Peginterferon Alfa-2b), SYNOVIR (Thalidomide), SYNRIBO (Omacetaxine Mepesuccinate), TAFINLAR (Dabrafenib), Tamoxifen Citrate, TARABINE PFS (Cytarabine), TARCEVA (Erlotinib Hydrochloride), TARGRETIN (Bexarotene), TASIGNA (Nilotinib), TAXOL (Paclitaxel), TAXOTERE (Docetaxel), TEMODAR (Temozolomide), Temozolomide, Temsirolimus, Thalidomide, TOPOSAR (Etoposide), Topotecan Hydrochloride, Toremifene, TORISEL (Temsirolimus), Tositumomab and I 131 Iodine Tositumomab, TOTECT (Dexrazoxane Hydrochloride), Trametinib, Trastuzumab, TREANDA (Bendamustine Hydrochloride), TRISENOX (Arsenic Trioxide), TYKERB (Lapatinib Ditosylate), Vandetanib, VECTIBIX (Panitumumab), VeIP, VELBAN (Vinblastine Sulfate), VELCADE (Bortezomib), VELSAR (Vinblastine Sulfate), Vemurafenib, VEPESID (Etoposide), VIADUR (Leuprolide Acetate), VIDAZA (Azacitidine), Vinblastine Sulfate, Vincristine Sulfate, Vinorelbine Tartrate, Vismodegib, VORAXAZE (Glucarpidase), Vorinostat, VOTRIENT (Pazopanib Hydrochloride), WELLCOVORIN (Leucovorin Calcium), XALKORI (Crizotinib), XELODA (Capecitabine), XGEVA (Denosumab), XOFIGO (Radium 223 Dichloride), XTANDI (Enzalutamide), YERVOY (Ipilimumab), ZALTRAP (Ziv-Aflibercept), ZELBORAF (Vemurafenib), ZEVALIN (Ibritumomab Tiuxetan), ZINECARD (Dexrazoxane Hydrochloride), Ziv-Aflibercept, Zoledronic Acid, ZOLINZA (Vorinostat), ZOMETA (Zoledronic Acid), and ZYTIGA (Abiraterone Acetate), including any formulation (e.g. liposomal, pegylated) or any brand name of any generic agent included herein.

In another embodiment, the bioactive agent is a combination of cancer therapeutic agents. Combinations of cancer therapeutic agents that are efficacious when combined are known. The following is a non-limiting list of combinations of cancer therapeutic agents that may be included as the bioactive agent (capital letters representing initialisms and acronyms refer to combinations rather than brand names): ABVD, ABVE, ABVE-PC, AC, AC-T, ADE, BEACOPP, BEP, CAF, CAPDX, CARBOPLATIN-TAXOL, CHLORAMBUCIL-PREDNISONE, CHOP, CMF, COPP, COPP-ABV, CVP, EPOCH, FEC, FOLFIRI, FOLFIRI-BEVACIZUMAB, FOLFIRI-CETUXIMAB, FOLFIRINOX, FOLFOX, FU-LV, GEMCITABINE-CISPLATIN, ICE, MOPP, R-CHOP, R-CVP, STANFORD V, VAMP, VeIP, and XELOX. These initialisms and acronyms representing combination cancer therapies are well known in the art and need not be defined here.

The bioactive agent or agents may be administered alone or with suitable pharmaceutical carriers. Preparations for parenteral, as well as local administration, include sterile aqueous or non-aqueous solutions, suspensions and emulsions, which may contain auxiliary agents or excipients which are known in the art and which may facilitate processing of the bioactive agents into preparations which can be used pharmaceutically. Pharmaceutical compositions, such as tablets and capsules can also be prepared according to routine methods.

Suitable formulations for administration include aqueous solutions of the bioactive agents in water-soluble form, for example, water-soluble salts. In addition, suspension of the bioactive agents as appropriate oily injection suspensions may be administered. Suitable lipophilic solvents or vehicles include fatty oils, for example, sesame oil, or synthetic fatty esters, for example, ethyl oleate or triglycerides. Aqueous injection suspensions that may contain substances which increase the viscosity of the suspension include, for example, sodium carboxymethyl cellulose, sorbitol and/or dextran. Optionally, the suspension may also contain stabilizers.

The bioactive agent also may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, the bioactive agents may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage is obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

In another aspect, the exogenous agent is a diagnostic agent. The diagnostic agent may be a contrast agent, such as a radioactive or colored marker, or any other means or substance capable of revealing a metabolism or pathology of the central nervous system through imaging or biopsy. Preferably, the diagnostic agent is one that indicates abnormal cell proliferation indicative of cancer. The diagnostic agent may be used in the invention as a market to indicate the efficacy of therapeutic treatments. For example, a signal indicating proliferation in the area surrounding a zone of ablation may indicate the need for additional rounds of treatment with cancer therapeutic agents. If the tumor itself is completed destroyed through IRE, additional rounds of treatment can employ reversible electroporation or blood-brain-barrier disruption surrounding the zone of ablation to spare healthy tissue in the vicinity of the tumor, and provide for disruption of the blood-barrier in the vicinity of the tumor (e.g., surrounding the zone of ablation) to allow for uptake of cancer therapeutic agents to treat infiltrating tumor cells.

In clinical settings, methods according to the invention can have ameliorative effects or curative effects. That is, a method can provide a reduction in cell growth of a tumor, a reduction in tumor size, or total ablation of the tumor. Further, the methods can provide for partial or complete elimination of tumor cells surrounding a zone of ablation. Total ablation of a tumor and complete elimination of infiltrating tumor cells in tissue surrounding the treated tumor may result in a curative effect.

Exemplary methods of the invention can include a single round of treatment or two or more rounds of treatment. That is, the methods of cell ablation, either intentionally or as a result of tumor size or shape, can result in less than complete destruction of a tumor. In such a situation, the methods can be repeated one or more times to effect the desired level of tumor reduction or killing of tumor cells surrounding the destructed tumor. As methods of the invention are relatively minimally invasive, multiple rounds of treatment are not as harmful to the patient as multiple rounds of traditional surgical intervention. Multiple rounds of administering EBT may be useful in prolonging the amount of time the blood-brain-barrier is disrupted to allow for the desired amount of exogenous agent to cross the barrier.

Methods of the invention can be part of a multi-modal treatment. The methods thus may comprise other cell-killing techniques known in the art. For example, the methods may further comprise exposing the tumor, or area surrounding the tumor, to radiation. It likewise may be performed after or between surgical intervention to remove all or part of a tumor.

According to embodiments, methods of the invention can be implemented in part using electroporation devices and systems. The electroporation devices according to the invention are suitable for minimally invasive temporary implantation into a patient, emission of a tissue-ablating level of an electrical field in combination with administration of an exogenous agent, and removal from the patient. The electroporation device according to the invention thus may be used in the treatment of tumors and infiltrating tumor cells and the treatment of patients suffering from tumors. The electroporation devices can take multiple forms, based on the desired three-dimensional shape of the electrical field for cell killing. However, in general, the electroporation devices include two or more electrically conducting regions.

Further, in general, the electroporation device takes a rod-like shape, with one dimension (i.e., length) being substantially longer than the other (i.e., width or diameter). While exemplary embodiments are configured in a generally cylindrical shape, it is to be understood that the cross-sectional shape of the electrode can take any suitable geometric shape. It thus may be circular, square, rectangular, oval, elliptical, triangular, pentagonal, hexagonal, octagonal, or any other shape.

The electroporation devices of the invention comprise one or more electrodes, which are electrically conductive portions of the device, or one or more ground electrode. The electroporation devices thus comprise electrically conductive elements suitable for temporary implantation into living tissue that are capable of delivering an electrical pulse to the living tissue. The electroporation device of the invention has a proximal end and a distal end. The proximal end is defined as the end at which the electroporation device is attached to one or more other elements, for control of the function of the device. The distal end is defined by the end that contacts target tissue and delivers electrical pulses to the tissue. The distal end thus comprises an exposed or exposable electrically conductive material for implantation into a target tissue. Typically, the distal end is described as including a "tip" to denote the region of the distal end from which an electrical pulse is delivered to a tissue. The device further comprises at least one surface defining the length and circumference of the device.

In exemplary embodiments, the electroporation device comprises a laminate structure, with alternating conductive and non-conductive or insulative layers expanding outward from the proximal-distal center axis to the surface of the device. In typical embodiments, the center most layer, which shows the smallest diameter or width, is electrically conductive and comprises a part of the electrode tip. However, in alternative embodiments, the center-most layer is an open channel through which a fluid may be passed or through which additional physical elements may be placed. Yet again, the center-most layer may comprise an insulative material. In embodiments comprising a laminate structure, the structure can provide a more customizable electric field distribution by varying the separation distances between electrically conductive regions. Alternatively, in embodiments, certain electrically conductive regions can be exposed or concealed by movement of an outer, non-conductive sheath. In embodiments that do not comprise a laminate structure, the separation lengths can be achieved by disposing on the surface non-conductive materials at various regions.

Hollow Core Device

Many IRE treatments may involve coupled procedures, incorporating several discrete aspects during the same treatment. One embodiment of the invention provides a device with a needle-like tip 910 with an incorporated hollow needle 990 with either an end outlet 991 (shown in Panel A) or mixed dispersion regions 961 (shown in Panel B). Such a configuration allows for highly accurate distribution of injectable solutions, including those comprising bioactive agents. Use of such a device limits the dose of treatment required as well as ensures the correct placement of the materials prior to, during, and/or after the treatment. Some of the possible treatment enhancers that would benefit from this technology are: single or multi-walled carbon nanotubes (CNTs); chemotherapeutic agents; conductive gels to homogenize the electric field; antibiotics; anti-inflammatories; anaesthetics; muscle relaxers; nerve relaxers; or any other substance of interest.

The schematics in FIG. 1 show two basic hollow needle designs that may be implemented to enhance solution delivery prior to, during, or after IRE treatment. They both have multiple conducting surfaces 920 that may act as charged electrodes, grounded electrodes, or electric resistors, depending on the treatment protocol. Panel A shows a hollow tip 910 for injection of agents at its end while Panel B has distributed pores 961 throughout for a more generalized agent distribution. As shown in Panel B, the pores are disposed in the non-conducting regions 930 of the device.

Device with Movable Outer Sheath

Figure 2:
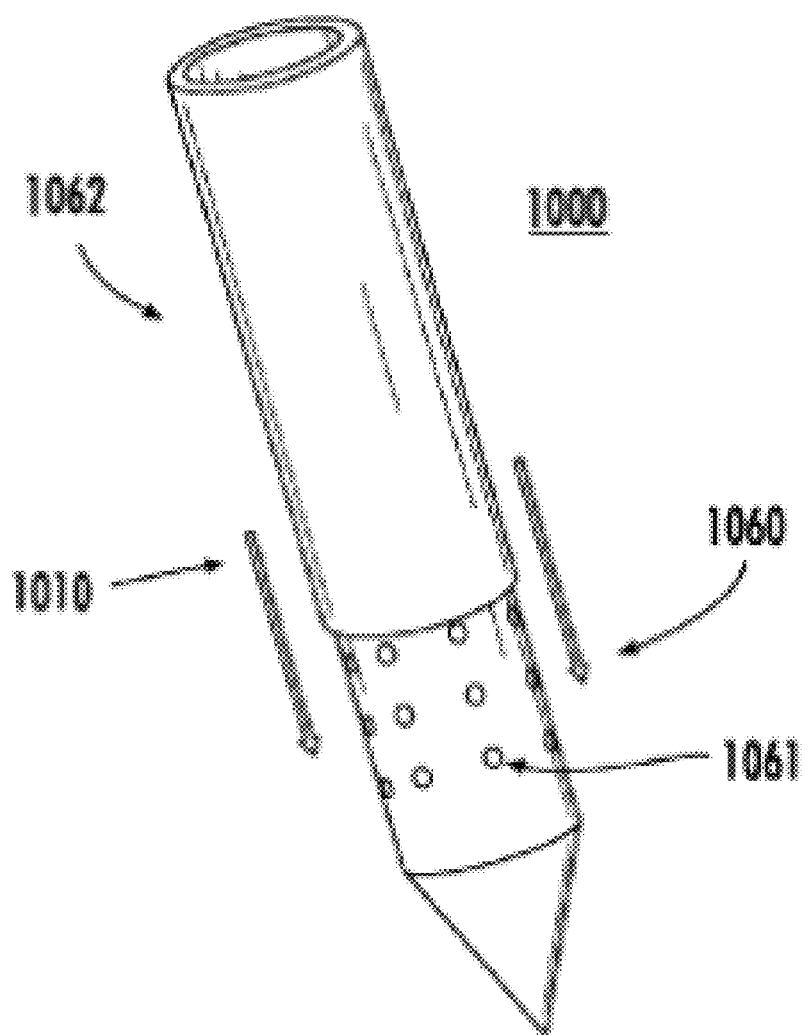
FIG. 2 is a schematic diagram of a device with moveable sheath according to embodiments of the invention.

In embodiments, the device comprises an outer protector that is designed to be movable up and down along the length of the device. FIG. 2 depicts such a movable outer protector. More specifically, FIG. 2 depicts a device 1000 comprising tip 1010 that includes outer protector 1062 that can be moved up and down along the length of device 1000. In practice, outer protector 1062 is disposed fully or partially encasing outer sheath 1060. After or during insertion into tissue to be treated, outer protector 1062 is retracted partially to expose outer sheath 1060, which in the embodiment depicted comprises mixed dispersion outlets 1061. As such, the number of dispersion outlets 1061 exposed to the tissue during treatment can be adjusted to deliver varying amounts of bioactive agent to different portions of the tissue being treated. Any mechanism for movement of the outer sheath along the device may be used. In embodiments, screw threads are disposed on the upper portion of the device, allowing for easy adjustment by simple twisting of the outer sheath. Alternatively, set screws may be disposed in the outer sheath, allowing for locking of the sheath in place after adjustment.

In some embodiments, one or more substantially open channels are disposed along the center axis or in place of one of the conductive or insulative layers. The channel(s) may be used as heat sinks for heat produced by the device during use. In embodiments, water or another fluid is held or entrained in the channel to absorb and/or remove heat.

The electroporation device of the invention comprises an electrode tip at the distal end. The electrode tip functions to deliver electrical pulses to target tissue. The tip may be represented by a single conductive layer of the device or may be represented by two or more conductive layers that are exposed to the tissue to be treated. Furthermore, the tip may be designed to have any number of geometrical shapes. Exemplary embodiments include tips having a needle-like shape (i.e., electrical pulses emanate from a small cone-like structure at the distal end of the device) or having a circular shape (i.e., electrical pulses emanate from the cylindrical outer surface of the device, which is a section of the device where the outer insulative layer has been removed to expose the next layer, which is conductive). For use in treatment of brain tumors, the tip advantageously comprises a blunt or rounded end to minimize laceration of brain tissue. In embodiments, the rounded or blunt end comprises a hole that allows for a sharp or needle-like structure to be deployed into tumor tissue.

The electroporation device comprises a proximal end, which generally functions for attachment of the device to a power source/controller and a handle. The proximal end thus may comprise connections for electrical wires that run from the power source/controller to the electrically conductive layers of the device. Standard electrical connections may be used to connect the conductive elements to the wires. In embodiments, the device is attached to a handle for ease of use by a human. While not limited in the means for attaching the device to the handle, in embodiments, the connection is made by way of a friction fit between the outer surface of the device and the handle, for example by way of an insulative O-ring (e.g., a Norprene O-ring) on the handle. In other embodiments, the device comprises, on its outer surface, ridges or other surface features that mate with surface features present on the handle. In yet other embodiments, the proximal end comprises one or more structures that allow for controlled movement of the outer surface along the length of the device. In such embodiments, the outer surface will comprise an outer sheath that is electrically non-conductive, and which surrounds an electrically conductive layer. Using the structures at the proximal end, the outer sheath may be moved, relative to the rest of the device, to expose or conceal varying portions of the electrically conductive material beneath it. In this way, the amount of surface area of the conductive material at the tip can be adjusted to provide a desired height of exposure of tissue to the electrode tip. Of course, other structures for securely fastening the device to a holder may be used, such as clips, set screws, pins, and the like. The device is not limited by the type of structure used to connect the device to the holder.

The electroporation device (such as the probes or electrodes) of the invention can be designed to have any desired size. Typically, it is designed to be minimally invasive yet at the same time suitable for delivery of an effective electrical field for IRE. The diameter or width of the probes or electrodes is thus on the order of 0.5 mm to 1 cm. Preferably, the diameter or width is about 0.5 mm to about 5 mm, such as about 1 mm, 2 mm, 3 mm, or 4 mm. The length of the device is not particularly limited, but is generally set such that a surgeon can use the device comfortably to treat tumors at any position in the body. Thus, for human use, the electroporation device is typically on the order of 40 cm or less in length, such as about 30 cm, 25 cm, or 15 cm, whereas for veterinary use, the length can be much larger, depending on the size of animal to be treated. For treatment of human brain tumors, the length can be on the order of 40 cm.

In some embodiments, the device, or a portion of it, is flexible. A flexible device is advantageous for use in accessing tumors non-invasively or minimally invasively through natural body cavities. In embodiments where the device or a portion of it is flexible, the shape of the device can change based on contact with body tissues, can be pre-set, or can be altered in real-time through use of wires or other control elements, as known in the art, for example in use with laparoscopic instruments.

The electroporation device of the invention can be part of a system. In addition to the device, the system can comprise a handle into or onto which the device is disposed. The handle can take any of a number of shapes, but is generally designed to allow a surgeon to use the device of the invention to treat a patient in need. It thus typically has a connector for connecting the device to the holder, and a structure for the surgeon to grasp and maneuver the device. The handle further can comprise a trigger or other mechanism that allows the surgeon to control delivery of electrical pulses to the device, and thus to the tissue to be treated. The trigger can be a simple on/off switch or can comprise a variable control that allows for control of the amount of power to be delivered to the device. Additionally, the handle may be created in such a manner that it may be attached to additional pieces of equipment, such as ones that allow precise placement of the electrode relative to an inertial or the patient's frame of reference, allowing steady and accurate electrode positioning throughout an entire procedure, which may entail the application of electric pulses in addition to radiotherapy, imaging, and injections (systemically and locally) of bioactive agents. Furthermore, the handle may be attached to machines that are operated remotely by practitioners (e.g., the Da Vinci machine).

The system can further comprise a power source and/or a power control unit. In embodiments, the power source and control unit are the same object. The power source provides electrical power to the device, typically by way of an electrical connection through the handle. The power source can be any suitable source that can deliver the proper amount of electrical power to the device of the invention. Suitable power sources are commercially available, and the invention is not limited by the type or manufacturer. The power control unit provides the user with the ability to set the power output and pulse time for electrical pulses to be delivered to the device, and thus to the tissue to be treated. Suitable control units are commercially available, and the invention is not limited by the type or manufacturer. For example, an appropriate power source/controller is available from Angiodynamics (Queensbury, N.Y.).

The electroporation device of the invention can be disposable or reusable. Where the device is designed to be reusable, it is preferably fabricated from materials that can be sterilized multiple times without destruction of the device. For example, the electroporation device can be fabricated from rust-resistant metals or alloys, such as stainless steel, and plastic or other synthetic polymeric materials that can withstand cleaning and sterilization. Exemplary materials are those that can be subjected to detergents, steam heat (e.g., autoclaving), and/or irradiation for at least one cycle of sterilization. Those of skill in the art can select the appropriate materials without undue experimentation, based on materials used in other medical devices designed to withstand common sterilization techniques.

Figure 3:
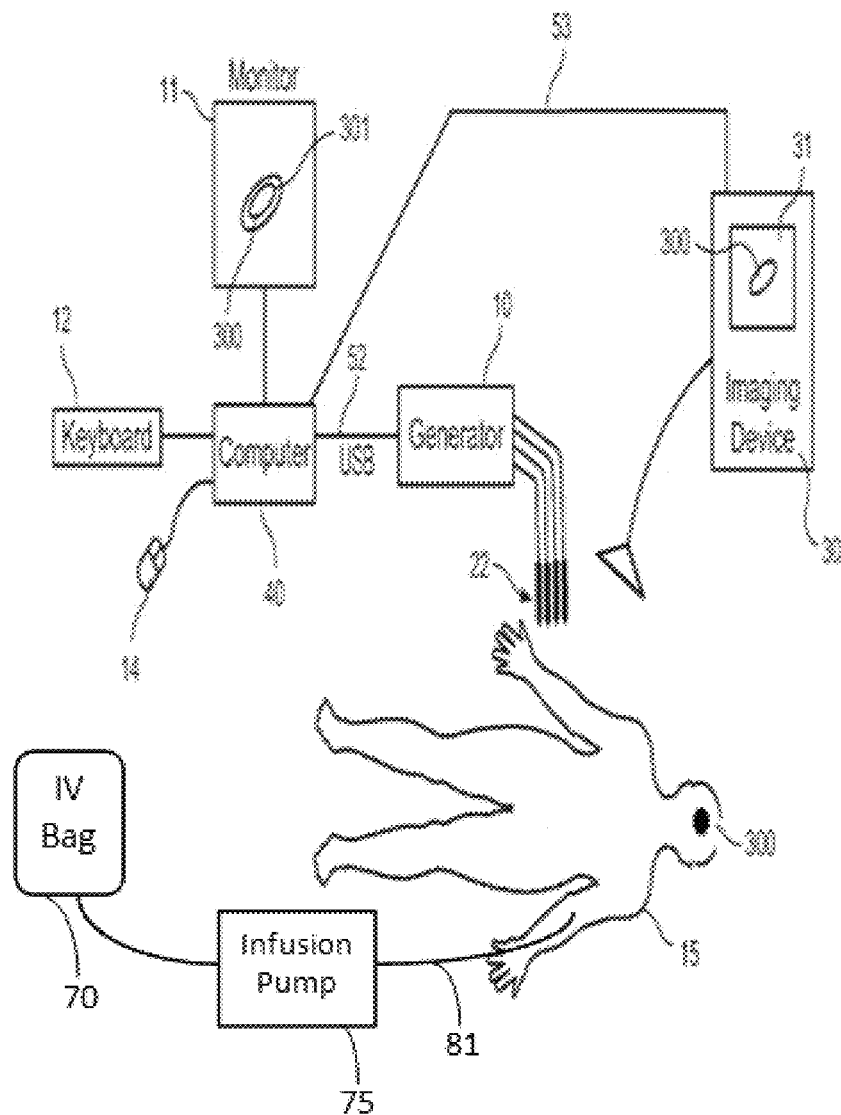
FIG. 3 is a schematic diagram of a representative system of the invention.
Figure 4:
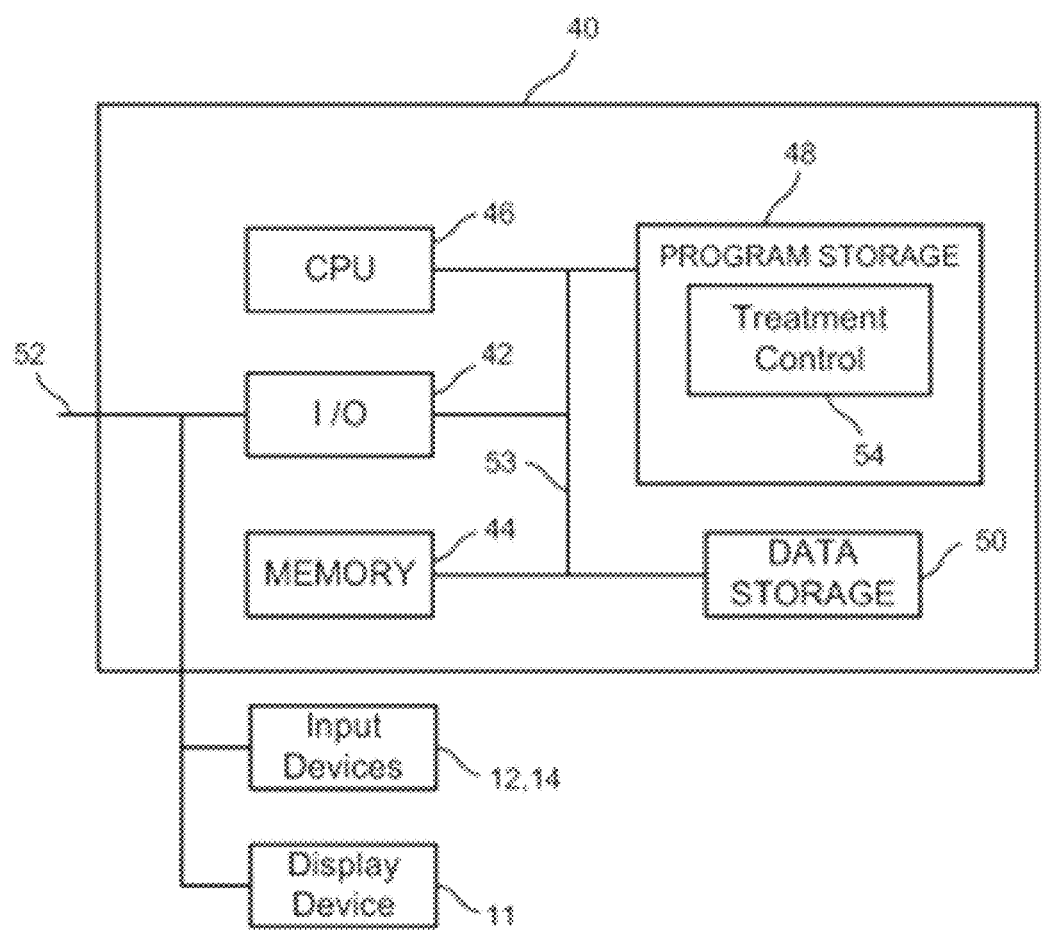
FIG. 4 is a schematic diagram of a representative treatment control computer of the invention.
Figure 5:
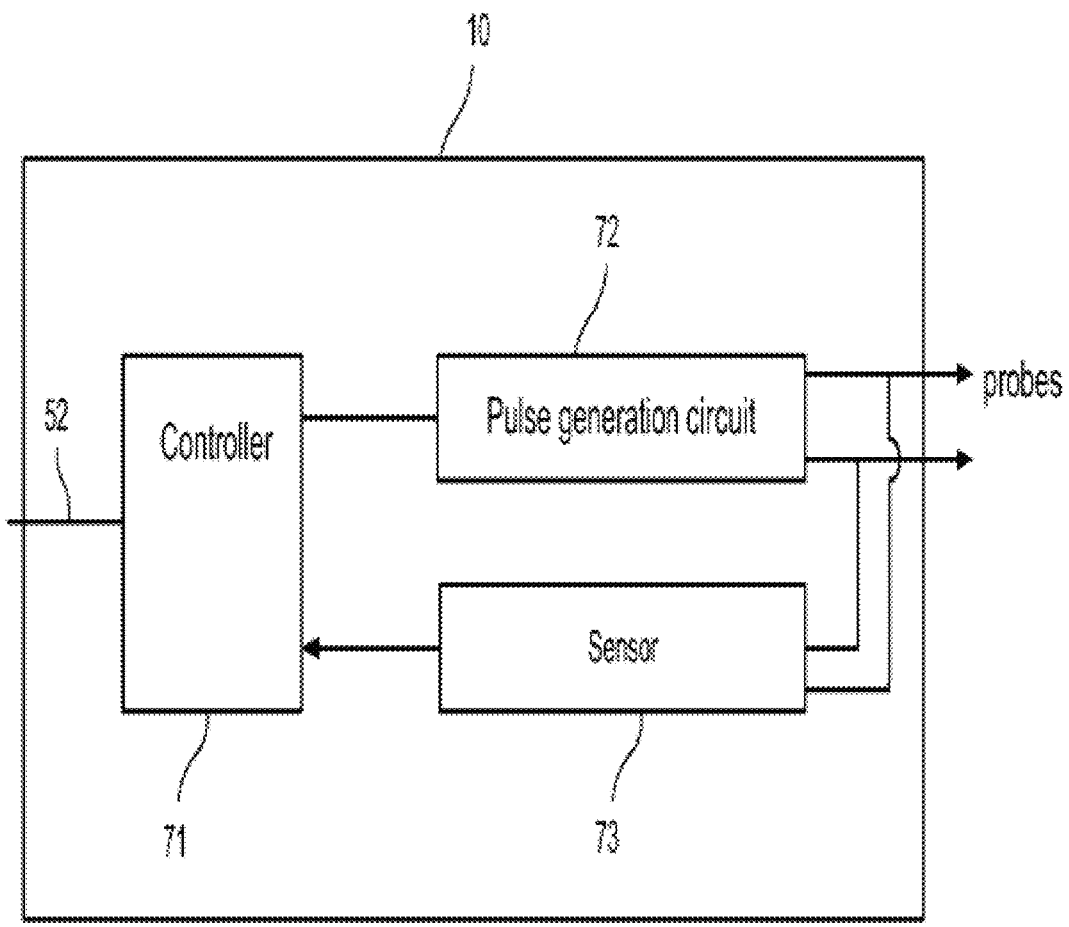
FIG. 5 is schematic diagram illustrating details of the generator shown in the system of FIG. 3, including elements for detecting an over-current condition.

One embodiment of a system for use in the methods of the present invention is illustrated in FIGS. 3 and 4. The components used with the present invention are illustrated in FIG. 3. One or more probes 22 deliver therapeutic energy and are powered by a voltage pulse generator 10 that generates high voltage pulses as therapeutic energy such as pulses capable of irreversibly electroporating the tissue cells. In the embodiment shown, the voltage pulse generator 10 includes six separate receptacles for receiving up to six individual probes 22 which are adapted to be plugged into the respective receptacle. The receptacles are each labeled with a number in consecutive order. In other embodiments, the voltage pulse generator can have any number of receptacles for receiving more or less than six probes.

In the embodiment shown, each probe 22 includes either a monopolar electrode or bipolar electrodes having two electrodes separated by an insulating sleeve. In one embodiment, if the probe includes a monopolar electrode, the amount of exposure of the active portion of the electrode can be adjusted by retracting or advancing an insulating sleeve relative to the electrode. See, for example, U.S. Pat. No. 7,344,533, which is incorporated by reference herein. The generator 10 is connected to a treatment control computer 40 having input devices such as keyboard 12 and a pointing device 14, and an output device such as a display device 11 for viewing an image of a target treatment area such as a brain tumor 300 surrounded by a tumor margin 301. The therapeutic energy delivery device 22 is used to treat a brain tumor 300 inside a patient 15. An imaging device 30 includes a monitor 31 for viewing the brain tumor 300 inside the patient 15 in real time. Examples of imaging devices 30 include ultrasonic, CT, MRI and fluoroscopic devices as are known in the art.

The system optionally includes medical equipment for administering a cancer therapeutic agent to the patient 15. In one embodiment, the equipment includes an IV bag 70 filled with a solution of the cancer therapeutic agent, a programmable infusion pump 75, and an IV line 81 for delivering the cancer therapeutic agent to the patient 15 into a vein of the patient 15, such as through a catheter, a central venous catheter, or a port. However, such embodiment is illustrative only, as the cancer therapeutic agent need not be administered intravenously. The cancer therapeutic agent can be administered to the patient 15 to treat tumor cells at the tumor margin 301.

The system of the present invention includes computer software (treatment planning module 54) which assists a user to plan for, execute, and review the results of a medical treatment procedure, as will be discussed in more detail below. For example, the treatment planning module 54 assists a user to plan for a medical treatment procedure by enabling a user to more accurately position each of the probes 22 of the therapeutic energy delivery device 20 in relation to the brain tumor 300 in a way that will generate the most effective treatment zone. The area affected can be predicted using numerical modeling, which can be used to ensure the ECM, blood vessels, and nerves are not thermally damaged. Even further, IRE treated areas can be predicted using mathematical models, such that the electric field needed for a particular situation may be predicted through numerical modeling thus allowing for reliable treatment planning. For example, to determine the efficacy of the electrode and understand the effects of the pulses on tissue, a numerical model has been developed capable of simulating treatments using a finite element software package, COMSOL Multiphysics. The treatment planning module 54 can display the anticipated treatment zone based on the position of the probes and the treatment parameters. The treatment planning module 54 can display the progress of the treatment in real time and can display the results of the treatment procedure after it is completed. This information can be used to determine whether the treatment was successful and whether it is desired to re-treat or further treat the patient.

For purposes of this application, the terms "code", "software", "program", "application", "software code", "computer readable code", "software module", "module" and "software program" are used interchangeably to mean software instructions that are executable by a processor. The "user" can be a physician or other medical professional. The treatment planning module 54 executed by a processor outputs various data including text and graphical data to the monitor 11 associated with the generator 10.

Referring now to FIG. 4, the treatment control computer 40 of the present invention manages planning of treatment for a patient. The computer 40 is connected to the communication link 52 through an I/O interface 42 such as a USB (universal serial bus) interface, which receives information from and sends information over the communication link 52 to the voltage generator 10. The computer 40 includes memory storage 44 such as RAM, processor (CPU) 46, program storage 48 such as ROM or EEPROM, and data storage 50 such as a hard disk, all commonly connected to each other through a bus 53. The program storage 48 stores, among others, a treatment planning module 54 which includes a user interface module that interacts with the user in planning for, executing and reviewing the result of a treatment. Any of the software program modules in the program storage 48 and data from the data storage 50 can be transferred to the memory 44 as needed and is executed by the CPU 46.

In one embodiment, the computer 40 is built into the voltage generator 10. In another embodiment, the computer 40 is a separate unit which is connected to the voltage generator through the communications link 52. In a preferred embodiment, the communication link 52 is a USB link. In one embodiment, the imaging device 30 is a stand-alone device which is not connected to the computer 40. In the embodiment as shown in FIG. 3, the computer 40 is connected to the imaging device 30 through a communications link 53. As shown, the communication link 53 is a USB link. In this embodiment, the computer can determine the size and orientation of the brain tumor 300 by analyzing the data such as the image data received from the imaging device 30, and the computer 40 can display this information on the monitor 11. In this embodiment, the lesion image generated by the imaging device 30 can be directly displayed on the grid (not shown) of the display device (monitor) 11 of the computer running the treatment planning module 54. This embodiment would provide an accurate representation of the lesion image on the grid, and may eliminate the step of manually inputting the dimensions of the lesion in order to create the lesion image on the grid. This embodiment would also be useful to provide an accurate representation of the lesion image if the lesion has an irregular shape.

It should be noted that the software can be used independently of the generator 10. For example, the user can plan the treatment in a different computer as will be explained below and then save the treatment parameters to an external memory device, such as a USB flash drive (not shown). The data from the memory device relating to the treatment parameters can then be downloaded into the computer 40 to be used with the generator 10 for treatment.

The present invention may be further illustrated by the foregoing Examples, which are intended to demonstrate certain principles and features of the invention rather than limit the scope of any claim.

EXAMPLES

Materials and Methods
In Vivo Irreversible Electroporation Protocol
The following example was performed with approval from the Institutional Animal Care and Use Committee (IACUC) at the Wake Forest University School of Medicine. Twenty-one male Fischer rats, weighing 190-220 g, were anesthetized by intraperitoneal injection of 10 mg/kg xylazine and 60 mg/kg ketamine. The head was clipped and prepared for aseptic surgery. Rats were immobilized in a small animal stereotactic headframe (Model 1350M, David Kopf Instruments, Tungisten, Calif., USA). A lateral rostrotentorial surgical approach was made and an 8 mm×3 mm rectangular, parieto-occipital craniectomy defect was created in the right aspect of the skull using a high-speed Dremel drill. Custom, blunt-tipped IRE caliper electrodes were advanced into the cerebral cortex using stereotactic coordinates referenced to the location of the rostral electrode (bregma 4 mm posterior, 3.5 mm lateral, 1.5 mm dorsoventral). The caliper electrodes used were 0.45 mm in diameter, had 1 mm exposure, and were 4 mm in edge-to-edge separation distance.

The two-electrode configuration used generates a non-uniform electric field distribution that depends on the applied voltage and dielectric properties of the tissue. Accordingly, voltage-to-distance ratios are referred to in order to enable other researchers with the IRE pulse parameters used. Animals underwent IRE treatment according to parameters in Table 1.

TABLE 1

IRE Pulse parameters and Evan's Blue/Gd administration schedule used.

| Time (min) | 0 V/cm | 200 V/cm | 400 V/cm | 600 V/cm | 800 V/cm | 1000 V/cm |
|---|---|---|---|---|---|---|
| −5 | † * |  | † * | † * | † * | † * |
| +5 | * |  | * | * | * | * |
| +15 |  | * |  | * |  | * |
| +30 |  |  | * | * | * |  |

† = Evan's Blue (n = 5);
* = Gadolinium (n = 16) (Magnevist ®). A separate animal was used to assess each time point and electric field (n = 21).

To assess permeability of the BBB, Gd was administered to animals (n=16) in each electric field group at varying times before or after delivering ninety 50-µs IRE pulses at a rate of one pulse per second (Table 1). If desired, the material to be delivered can alternatively or in addition be administered during the electrical energy based procedure. Each animal received only a single contrast agent injection, with a separate animal being used to assess each time point and applied electric field. The control (sham) animals had the electrodes inserted into the brain but no pulses were delivered. One animal (n=5) in each electric field group received Evan's Blue (50 mg/kg, IP) 5 minutes prior to IRE and was euthanized 30 minutes after pulse delivery without being subjected to magnetic resonance imaging (MRI) examination. Disruption of BBB, visible on histological sections in the animals was compared to the contrast-enhanced regions observed using MRI.

Magnetic Resonance Imaging

A 7.0-T small animal MRI scanner (Bruker Biospec 70/30, Ettlingen, Germany) was used. Body temperature was maintained during scanning with thermostatically-controlled warm air. The heart rate, respiratory rate, and temperature were telemetrically monitored during scanning. A 38 mm inner diameter quadrature volume coil was used for RF signal transmission and reception (Litzcage, Doty Scientific, Columbia, S.C.). Sequence acquisition parameters were: T1-weighted (T1W) images were acquired using Rapid Acquisition with Relaxation Enhancement (RARE) pulse sequence with 8 echoes (TR=1440 ms, TE=7.5 ms, FOV=4 cm, matrix=256×256, slice thickness=0.5 mm, NEX=8), followed by the T2-weighted (T2W) images which were acquired using a RARE pulse sequence with 8 echoes (TR=6575 ms, TE=60 ms, FOV=4 cm, matrix=256×256, slice thickness=0.5 mm, NEX=8). T1W images were obtained following intraperitoneal administration of 0.1 mmol/kg of gadopentetate dimeglumine (Magnevist®: Bayer HealthCare Pharmaceuticals, Wayne N.J.), but administration of the same or similar amount of gadobenate dimeglumine (Multihance: Bracco Diagnostics, Princeton, N.J.) can also be used. The contrast was injected in reference to the delivery of the electric pulses according to the schedule in Table 1.

MR images were obtained 5-15 minutes after contrast injection which is consistent with where most of the enhancement from an IP injection of gadopentetate dimeglumine occurs as shown by Howles et al. (Howles G P, Bing K F, Qi Y, Rosenzweig S J, Nightingale K R, et al. (2010) Contrast-enhanced in vivo magnetic resonance microscopy of the mouse brain enabled by noninvasive opening of the BBB with ultrasound. Magn Reson Med 64: 995-1004). Cross-sectional areas of contrast were contoured independently in a semi-automated manner on each slice of the T1W+Gd sequence, with volumes of contrast-enhancing tissue being calculated automatically with Mimics software 14.1 (Materialise, Leuven, B G). Because Gd is too large to cross the intact BBB in the cerebrum, any increase in contrast enhancement evident on T1W+Gd images, compared with levels of enhancement seen in the control animals, was taken as direct evidence of BBB disruption induced by IRE (Liu et al., 2010; Frigeni et al., 2001; Noce et al., 1999). T2W images were used to evaluate any edema surrounding the IRE ablated regions.

Contrast enhancement intensity was quantified using four reference tubes filled with known Gd concentrations (0, 0.09, 0.19, and 0.24 mg/ml) in saline and scanned with each rodent. A calibration curve was determined to allow for calculation of a normalized mean value of Gd concentration within the IRE-induced volume of BBB disruption (Hirschberg H, Zhang M J, Gach H M, Uzal F A, Peng Q, et al. (2009) Targeted delivery of bleomycin to the brain using photo-chemical internalization of Clostridium perfringens epsilon prototoxin. J Neurooncol 95: 317-329). Three mean intensity measurements within a 3.2 mm$^2$ circle were averaged along the reference tubes in order to minimize the intensity variations within each scan. These independent measurements were performed on MRI slices that corresponded with the rostral and caudal electrode insertions and one slice in-between the electrodes. The mean intensity of each 3D reconstructed lesion was divided by the mean intensity of the 0.09 mg/ml reference tube in order to normalize the Gd concentration across the different treatments. The normalized intensities were then converted to Gd concentrations and are provided in the results section.

Histopathology

An adult rat brain matrix slicer (Zivic Instruments, Pittsburgh, Pa.) was used to obtain contiguous 3.0 mm coronal brain sections of formalin fixed brains. Brain sections were paraffin embedded, sectioned at 5 µm, and stained with hematoxylin-eosin (H&E). Each microscopic brain section was photographed at 150× magnification using a digital camera (Nikon DS-Fi1, Nikon, Japan). For each treatment and time, 3 separate independent hand drawn regions of interest (ROI) were traced around the boundaries of the IRE zone of ablation present in the brain, and the area of each ROI determined using the area function of image analysis software (NIS-Elements AR, Nikon, Japan).

The ROI limits from which IRE zones of ablation were traced used the following anatomic boundaries: dorsal—dura mater, ventrolateral—inner limit of external capsule, ventromedial—inner limit of corpus callosum. Any intervening cerebrocortical tissue that was lesioned within these limits was included in the ROI. For sections in which IRE treatment resulted in a full thickness cerebrocortical defect or cavitation of tissue architecture, the lesion area was determined by subtracting the area of the cerebral hemisphere remaining intact on the IRE treated side of the brain (FIG. 6D-Y, dashed line) from the area of the contralateral (untreated; FIG. 6D-X, solid line) cerebral hemisphere. Cerebral hemispheric areas were determined from three separate hand-drawn ROI, using photomicrographs obtained at 50× magnification, as described above.

Statistical Analysis

Statistical analysis on the effect of applied electric field and timing of Gd administration was conducted using JMP 9.0 (SAS, South Cary, N.C.) via Fit of Least Squares with $\alpha=0.05$. Linear regression analysis of the relationship between electric field and volume of ablation was also performed as it was found appropriate using previously published data (Garcia P A, Rossmeisl J H, Jr., Neal R E, 2nd, Ellis T L, Davalos R V (2011) A Parametric Study Delineating Irreversible Electroporation from Thermal Damage Based on a Minimally Invasive Intracranial Procedure. Biomed Eng Online 10: 34).

Results

Figure 6A:
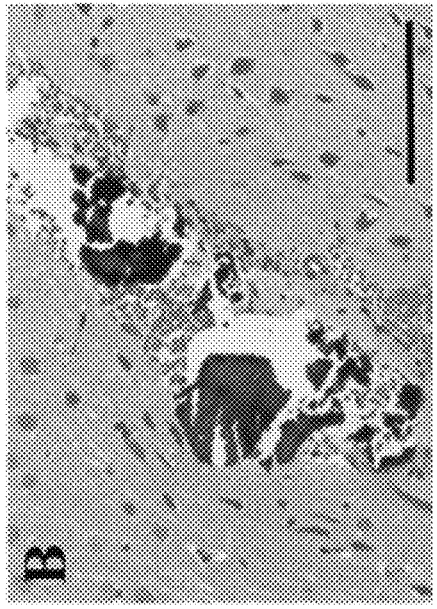
FIGS. 6A-6D are images showing histopathologic evaluations of IRE-induced effects determined with Hematoxylin and Eosin stain.
Figure 6B:
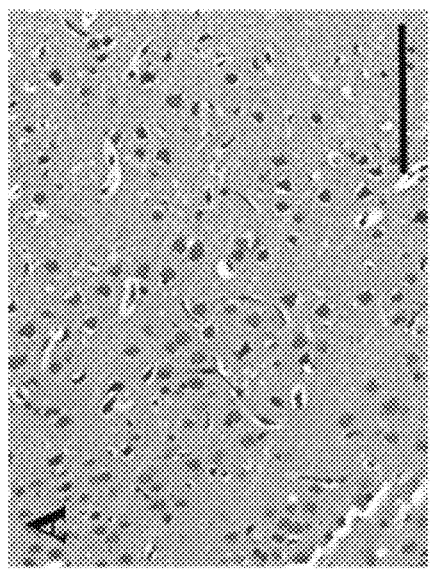
Figure 6C:
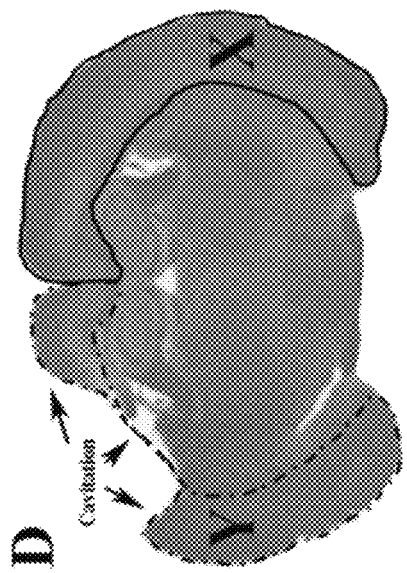
Figure 6D:

FIGS. 6A-6D are images showing histopathologic evaluations of IRE-induced effects determined with Hematoxylin and Eosin stain. Histopathologic sections of cerebral cortex from untreated control rat (FIG. 6A), sham treated rat with physical displacement of the neuropil in the trajectory of the electrode (FIG. 6B), and cortical ablation zone resulting from 800 V/cm IRE treatment (FIG. 6C). Histopathologic lesion area determination in presence of IRE induced cavitary cerebral defect (FIG. 6D). The IRE lesion area ($mm^2$) =untreated cerebral area (X)–IRE lesioned cerebral area (Y). Bar=500 µm in FIGS. 6A-6C.

On gross examination of the brain (FIG. 6A), sham treatment resulted in two punctate, 1 mm cortical depressions corresponding to the points of electrode insertions. In histopathological sections, sham zones of ablation were characterized by physical displacement of the brain tissue along the electrode tracks and associated with microhemorrhage into the electrode tracks. Zones of ablation in sham-treated rats were limited to the immediate proximity of the electrode insertions, with the adjacent neuropil retaining normal cortical architecture and morphology (FIG. 6A). At voltage-to-distance ratios of 200 V/cm and 400 V/cm (FIG. 6B), observed gross and histopathological zones of ablation were morphologically indistinguishable from those of sham-treated rats. At voltage-to-distance ratios greater than 600 V/cm, IRE treatment resulted in distinct areas of parenchymal ablation (FIG. 6C). Grossly, ablated regions were malacic. Microscopically, IRE zones of ablation were characterized by an eosinophilic, vacuolated amorphous debris and multifocal areas of intraparenchymal hemorrhage, consistent with coagulative necrosis. Variably-sized regions of intraparenchymal hemorrhage were noted; these were most pronounced immediately adjacent to and within electrode insertion tracks similar to previous results in canine brain (Ellis et al, 2011). Remnant neurons within ablated regions were shrunken, had hypereosinophilic cytoplasm and showed nuclear pyknosis and/or karyolysis. Free glial nuclei in various states of degeneration were scattered throughout ablation zones.

Figure 7:
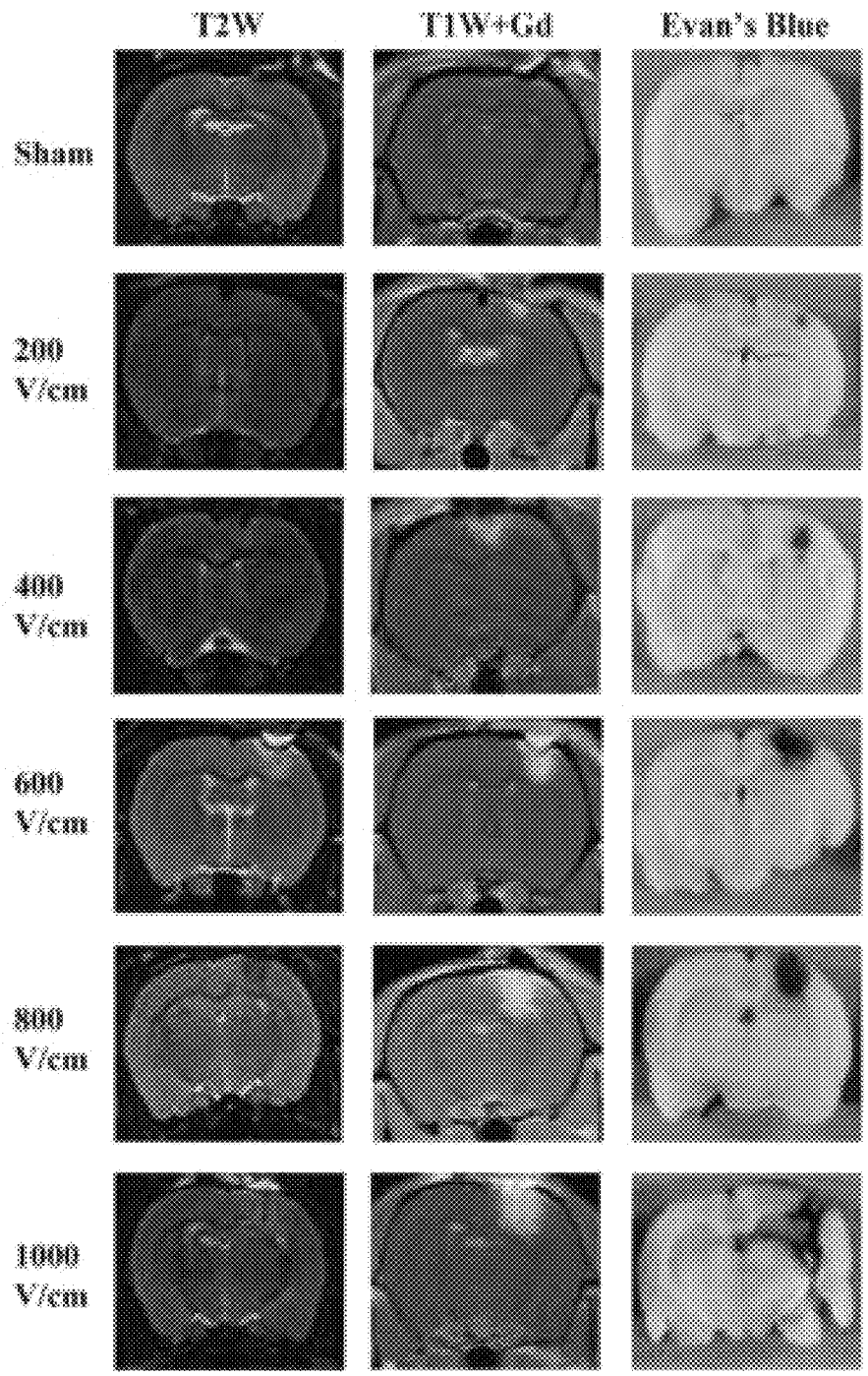
FIG. 7 is a series of magnetic resonance images and images of Evan's Blue brain sections showing morphologic characteristics of IRE-induced BBB disruption comparing where no pulses are applied and treatments involving 50-μs pulses applied at 200, 400, 600, 800, and 1000 V/cm using 1-mm electrodes (0.45 mm diameter).

All treatments resulted in zones of ablation visible on MRI (FIG. 7). The zones of ablation were achieved with ninety 50-µs pulses at a rate of one pulse per second. The Gadolinium (Gd) and Evan's Blue dyes were administered IP 5 minutes before the delivery of the pulses. In sham-treated rats in which the electrodes were inserted into the brain but no pulses applied, zones of ablation were limited to physical displacement of the brain parenchyma, which appeared as hypointense electrode tracks on T1W+Gd and T2W sequences (FIG. 7). No contrast enhancement or intraparenchymal uptake of Evan's blue in the adjacent brain was observed in sham-operated rats (FIG. 7). At all voltage-to-distance ratios examined, IRE treatment induced heterogeneous T2W zones of ablation characterized by a hypointense central lesion with perilesional T2W hyperintensity (FIG. 7) and markedly and uniformly contrast-enhancing zones of ablation that were sharply delineated from the adjacent brain tissue (FIG. 7). The positive correlation between the applied voltage-to-distance ratios and the extent of BBB disruption induced by IRE is indicated by the uniformly contrast-enhancing zones of ablation on the T1W+Gd MR images and corresponding Evan's Blue brain slices. IRE-induced zones of ablation are sharply demarcated from the surrounding brain parenchyma. Linear hypointensities in the center of the zones of ablation, corresponding to the electrode insertions, are evident in the MR images from the 600, 800, and 1000 V/cm treatments.

FIGS. 8A-8H are magnetic resonance images of brain sections showing qualitative representations of IRE-induced BBB disruption and in particular, 2D IRE lesion tracing on the coronal (FIG. 8A, FIG. 8B), dorsal (FIG. 8C, FIG. 8D), and sagittal (FIG. 8E, FIG. 8F) planes with the corresponding non-contiguous (FIG. 8G) and contiguous (FIG. 8H) 3D reconstruction zones of ablation representative of 400 V/cm and 1000 V/cm IRE treatments, respectively. These reconstructions illustrate the shapes of the IRE zones of ablation, which are consistent with the electric field distributions that would be generated with the electrode configuration and pulse parameters used here. By optimizing treatment protocols and electrode configurations, it is possible to disrupt the BBB to target different size and shapes of tissue.

Figure 8E:
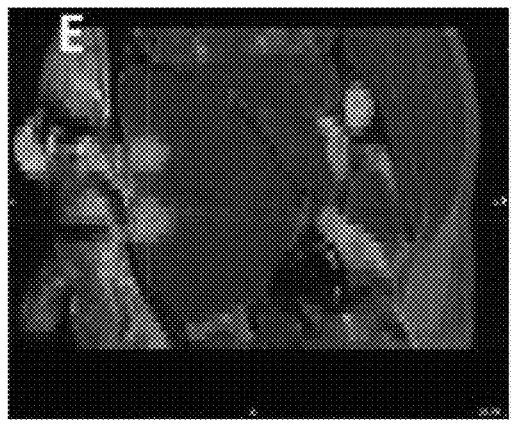
Figure 8F:
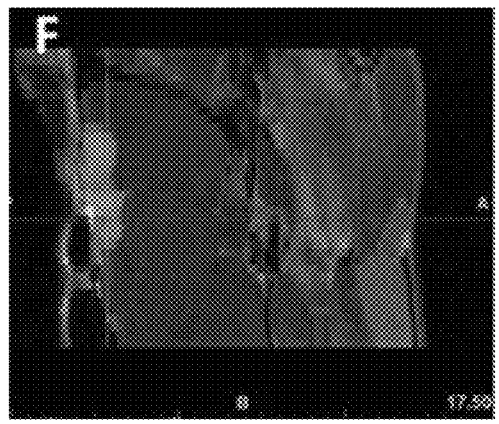
Figure 8G:
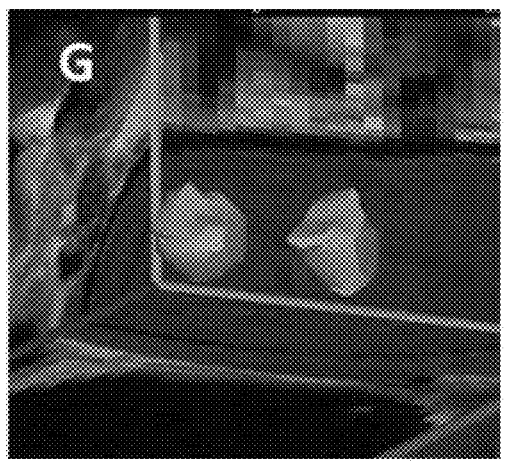
Figure 8H:
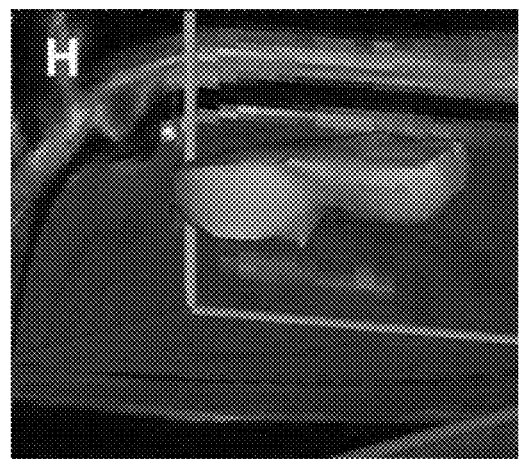

On MRI scans (FIGS. 8A-8H), treatment at 200 V/cm and 400 V/cm induced two non-contiguous ovoid to spherical IRE zones of ablation centered around the electrodes tips (FIGS. 8A, 8C, 8E), with the largest cross-sectional area in the coronal plane along the electrode tract. 3D reconstructions demonstrated two separated spherical regions surrounding the 1-mm electrodes (FIG. 8F). IRE treatment at 600 V/cm, 800 V/cm, and 1000 V/cm resulted in a "peanut shape" lesion that was contiguous between the two electrodes (FIGS. 8B, 8D, 8F), with similar characteristics to the 3D reconstruction in FIG. 8H. The different reconstructed geometries for each applied voltage confirm the electric-field dependent effect of IRE. In addition, these results suggest that the threshold for IRE-induced BBB disruption is between 400 V/cm and 600 V/cm which is consistent with previous studies in brain (Garcia et al., 2010).

Figure 9A:
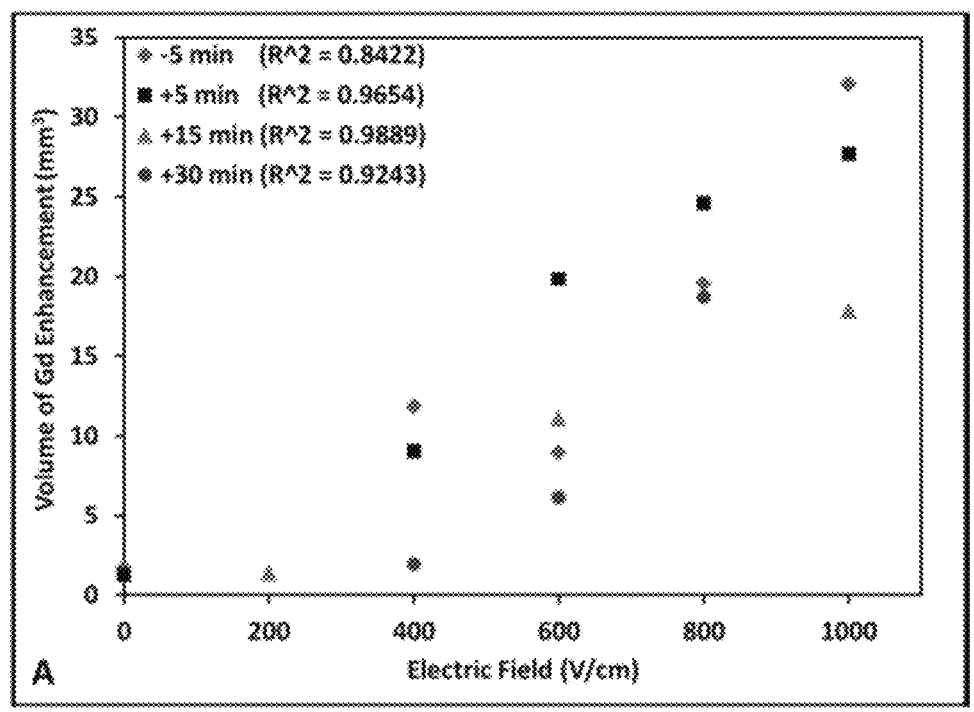
FIGS. 9A and 9B are graphs showing quantification of IRE-induced BBB disruption from the 3D MRI reconstructions, where volumes (FIG. 9A) and mean concentrations (FIG. 9B) of Gd enhancement are provided as a function of the applied voltage-to-distance ratio and timing of Gd administration.
Figure 9B:
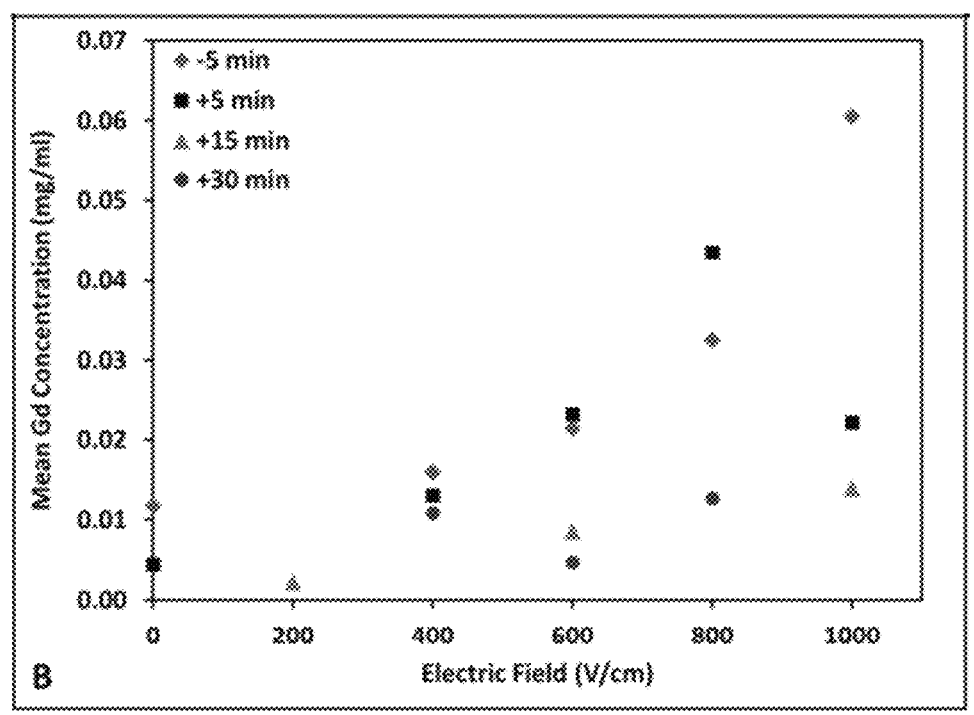

With histopathologic (FIGS. 6A-C), Evan's Blue (FIG. 7), and MRI (FIGS. 8A-8H) examinations, the extent of BBB disruption was positively correlated with the applied voltage-to-distance ratio. Objective measurements confirming this are provided in FIGS. 9A and 9B, in which the volumes (FIG. 9A) of gadolinium (Gd) enhancement and mean concentrations (FIG. 9B) are plotted as a function of the applied voltage-to-distance ratio and timing of Gd administration. Within each time points in which Gd was administered, linear correlations were determined between electric fields and volumes of ablation (−5 min: $R^2$=0.8422, +5 min: $R^2$=0.9654, +15 min: $R^2$=0.9889, +30 min: $R^2$=0.9243). There was a significant positive correlation of Gd volume (p<0.0001) and mean concentration (p=0.0077) with applied electric field. The negative correlation of Gd volume (p=0.0151) and concentration (p=0.0056) with time was also statistically significant, confirming the transient permeabilization surrounding the regions of ablation. Exposing the brain tissue to increasing applied electric fields resulted in larger volumes of Gd enhancement. Although the number of replicates is low, the finding of increasing volume of affected tissue with increasing voltage applied (for the electrode configuration and pulse parameters used) suggests that volume is directly related to voltage. Similarly, the finding of a trend toward decreased volumes with increasing delays after Gd administration suggests a possible transient quality to the permeabilization surrounding the regions of ablation. The linear fit used to correlate the electric field and zone of ablation was found appropriate using previously published data (Garcia P A, Rossmeisl J H, Jr., Neal R E, 2nd, Ellis T L, Davalos R V (2011) A Parametric Study Delineating Irreversible Electroporation from Thermal Damage Based on a Minimally Invasive Intracranial Procedure. Biomed Eng Online 10: 34). The mean concentrations of Gd within the reconstructed IRE-induced regions of BBB disruption are also positively correlated with the applied electric field. This provides evidence that with increasing electric field strengths even more electroporation is achieved and transport of Gd or other exogenous agents is enhanced.

Cross sectional areas of Gd enhancement around the rostral electrode were also calculated, to compare the results from the T1W+Gd MRI with the corresponding cross-sectional areas seen in the histopathology and gross pathology specimens along the coronal plane. Table 2 shows cross-sectional areas of Gd enhancement from the MRI, cross-sectional areas of IRE cell death derived from H&E images, and cross-sectional areas of permeabilization from the Evan's Blue. The cross-sectional areas of Gd enhancement (p<0.0001) and cell death (p<0.0001) surrounding the rostral electrode were evaluated via Standard Least Square Fit and showed a significant positive correlation with the applied electric field. No significant correlation was found between the cross-sectional areas of MRI enhancement and timing of Gd administration. The results indicate that the cross-sectional areas of Gd enhancement and Evan's Blue are predominantly greater than the cell death cross-sectional areas from the H&E stained sections, confirming the existence of the penumbra of transient BBB disruption.

TABLE 2

Resulting IRE-induced BBB disruption mean concentrations, volumes, and cross-sectional areas calculated using the Gd enhancement in MRI, H&E, and Evan's Blue.

| Time (min) | E-Field (V/cm) | Mean Gd Conc. (mg/ml) | Gd (MRI) ($mm^3$) | Gd (MRI) ($mm^2$) | H&E ($mm^2$) | Evan's Blue ($mm^2$) |
|---|---|---|---|---|---|---|
| −5 | 0 | 0.012 | 1.62 | 0.00 | 1.31 | |
| −5 | 400 | 0.016 | 11.82 | 1.56 | 1.52 | 3.22 |
| −5 | 600 | 0.021 | 8.97 | 4.22 | 3.14 | 3.98 |
| −5 | 800 | 0.033 | 19.55 | 5.15 | 4.83 | 4.29 |
| −5 | 1000 | 0.060 | 32.00 | 6.67 | 4.51 | 4.97 |
| +5 | 0 | 0.004 | 1.26 | 0.46 | 1.14 | |
| +5 | 400 | 0.013 | 9.07 | 3.66 | 2.08 | |
| +5 | 600 | 0.023 | 19.83 | 4.05 | 3.82 | |
| +5 | 800 | 0.043 | 24.61 | 5.25 | 3.04 | |
| +5 | 1000 | 0.022 | 27.69 | 4.91 | 5.84 | |
| +15 | 200 | 0.002 | 1.39 | 1.22 | 1.39 | |
| +15 | 600 | 0.009 | 11.13 | 4.79 | 3.39 | |
| +15 | 1000 | 0.014 | 17.85 | 4.79 | 5.46 | |
| +30 | 400 | 0.011 | 1.93 | 1.17 | 1.09 | |
| +30 | 600 | 0.005 | 6.16 | 2.25 | 1.68 | |
| +30 | 800 | 0.013 | 18.71 | 6.25 | 4.63 | |

Note:
The cross-sectional areas were determined from the regions intersecting the rostral electrode tip.

Figure 10A:
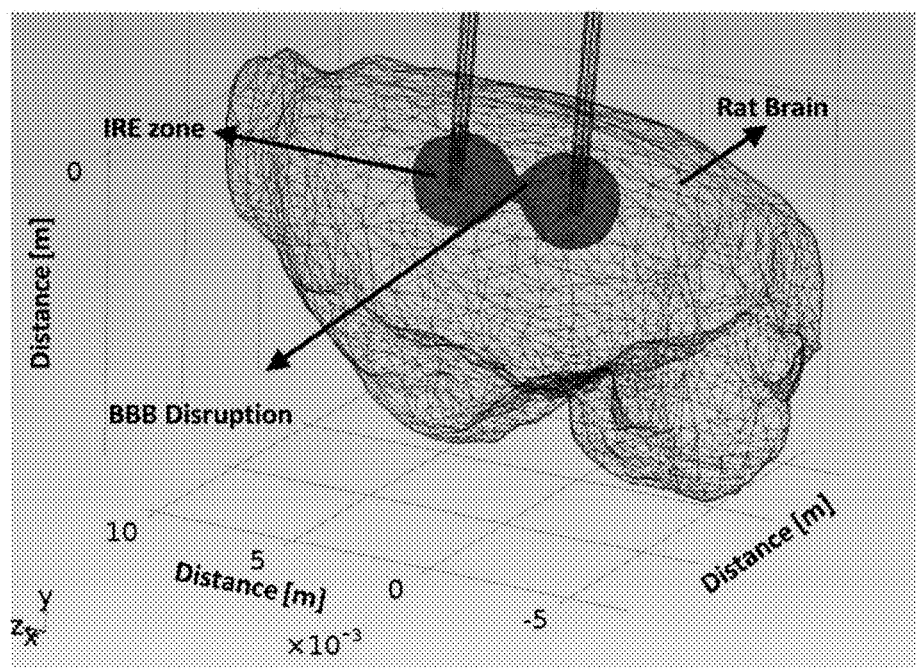
FIGS. 10A-10C are electric field and temperature distributions depicting the zones of IRE ablation and BBB disruption using ninety 50-ρs pulses at 1000 V/cm and Gd administered 5 min prior to pulse delivery using the cross-sectional MRI/H&E data from Table 2. Specifically, FIG. 10A compares the IRE volume of ablation with the volume of BBB disruption.
Figure 10B:
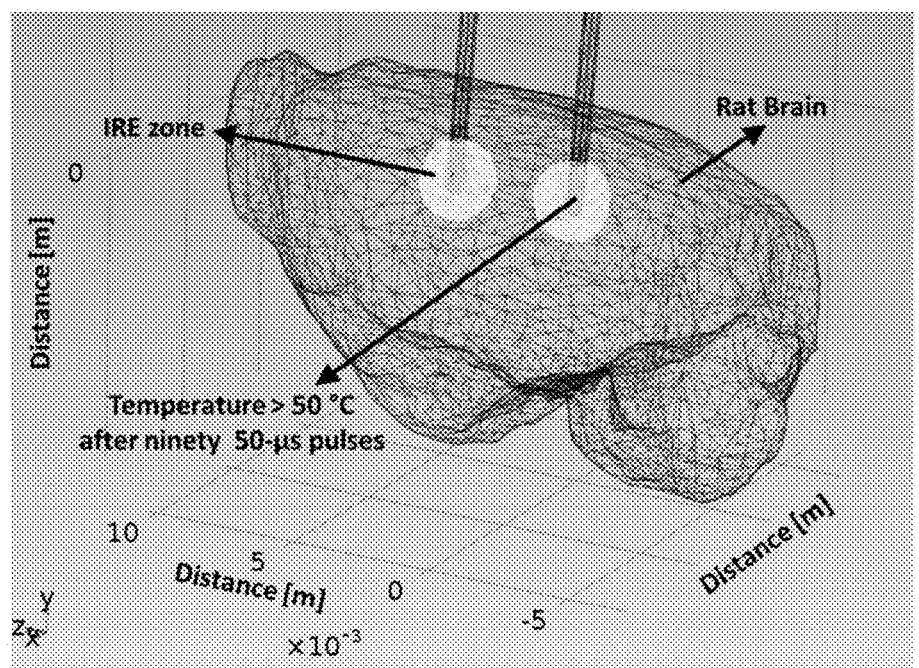
Figure 10C:
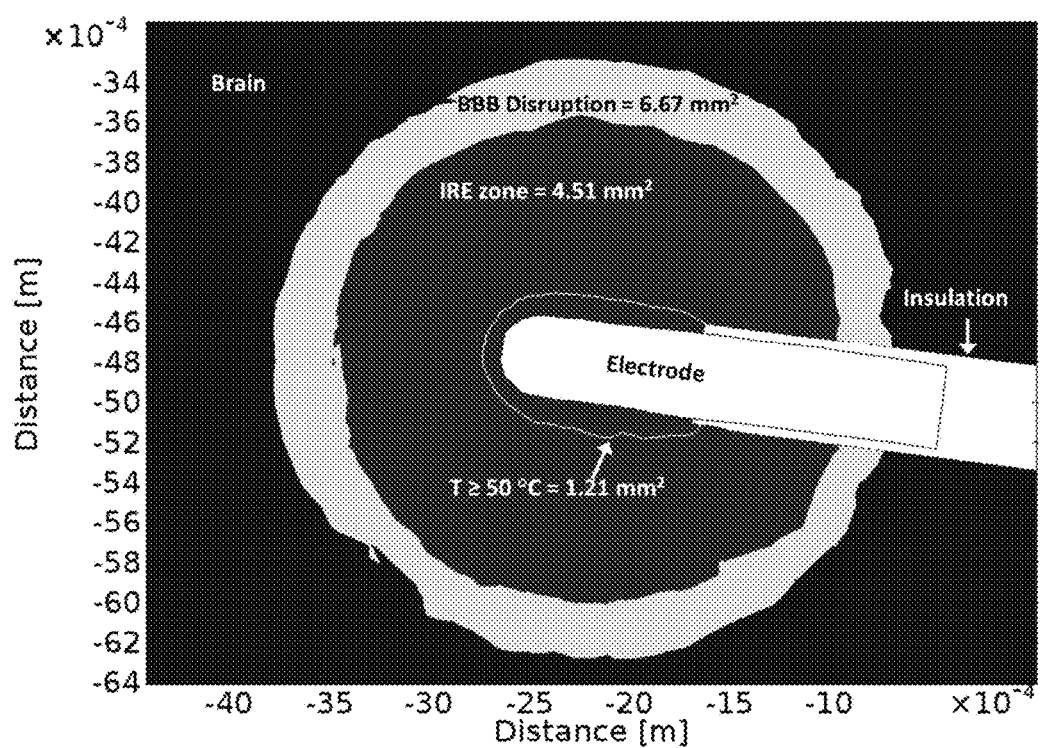

3D MRI reconstructions of the rat brain were developed in order to simulate the experimental results found in the study in which ninety 50-μs pulses were delivered at 1000 V/cm voltage-to-distance ratio with 1-mm electrodes (0.45 mm diameter) using COMSOL Multiphysics version 4.3a (Burlington, Mass.) and the cross-sectional data from Table 2. Specifically, electric field and the resulting temperature distributions were simulated in order to illustrate the potential region of IRE ablation, BBB disruption, and elevated temperatures. FIG. 10A compares the volume of IRE ablation with the volume of BBB disruption. FIG. 10B compares the volume of IRE ablation with the volume of tissue with elevated temperatures (T≥50° C.) at the completion of the ninety pulse IRE treatment. This result demonstrates that there might be some transient increase in the Temperature in the vicinity of the electrode-tissue interface but the majority of the tissue will be affected by the non-thermal mode of cell death. Ultimately, FIG. 10C displays the areas of IRE ablation, BBB disruption, and elevated temperatures (T≥50° C.) surrounding the rostral electrode. It is important to know that the pulse parameters can be optimized to target a particular volume of ablation and surrounding region of BBB disruption for infiltrative cancer cell attack.

The same 3D MRI reconstruction was used to analyze the volumetric results of Gd enhancement from the experiments in Table 2. In this example we integrated the volume of brain tissue being exposed to identical pulse parameters performed experimentally and described in Table 1. In particular, FIG. 11A shows the 3D MRI reconstruction and the electrodes inserted into the brain tissue. FIG. 11B-11F replicated each of the treatments investigated and provides the electric field threshold that was required to match the volume of BBB disruption to the volume of Gd enhancement. Specifically, FIG. 11B (200 V/cm) did not have any detectable Gd enhancement during the analysis with Mimics software 14.1 (Materialise, Leuven, B G). However, the 400 V/cm (9.07 $mm^3$=298 V/cm), 600 V/cm (19.83 $mm^3$=328 V/cm), 800 V/cm (24.61 $mm^3$=406 V/cm), and 1000 V/cm (27.69 $mm^3$=476 V/cm) IRE treatments resulted in BBB disruption electric field thresholds between 298-476 V/cm as demonstrated in FIG. 11C-11F. It is important to note that these results were achieved with ninety 50-μs pulses delivered at 1 pulse per second with Gd administered 5 min post-IRE but could be optimized to achieve other therapeutic outcomes as well. Using rodents as predictive models, data herein is presented on the duration and extent of acute BBB disruption surrounding an IRE-induced zone of ablation. Not wishing to be bound by any one particular theory, it is believed that there is a minimal electric field at which BBB disruption occurs surrounding an IRE-induced zone of ablation and that this transient response can be measured using Gd uptake as a surrogate marker for BBB disruption. IRE was performed at different electric fields and varied the timing of Gd administration to estimate the duration of any reversible effects on BBB disruption. The results show representative minimal pulse parameters capable of effective BBB disruption and provide an estimate of the duration and extent of reversible effects on BBB disruption, showing the creation of a non-destructive penumbra of BBB disruption adjacent to regions of IRE-induced cell death occurs.

IRE-induced BBB disruption over the entire range of electric field strengths evaluated was observed. These results provide preliminary guidelines for electric field thresholds for IRE in the normal rodent brain. Histopathological examinations were consistent with previous pathological descriptions of IRE-induced cerebrocortical ablations (Ellis et al., 2011; Garcia et al., 2010) at applied voltage-to-distance ratios greater than 600 V/cm, while the morphology of brain tissue treated at voltage-to-distance ratios smaller than 400 V/cm was identical to sham-treated rodents. This indicates electroporation is predominantly or exclusively reversible at voltage-to-distance ratio strengths <400 V/cm in normal brain, using the pulse parameters applied herein. The extent of reversible BBB disruption induced by IRE is underestimated using methods based on H&E stained sections, when compared to paramagnetic contrast agents or vital dye surrogates of BBB disruption. Co-labeling methods, that simultaneously utilize both imaging contrast agents and vital dyes, would be recommended in future studies to define the reversible electroporation domain in brain tissue (Chopra A (2004-2010) Evans Blue-diethylenetriamine-N,N,N",N"-pentaacetic acid-gadolinium. Molecular Imaging and Contrast Agent Database (MICAD). Oct. 25, 2007 ed: Bethesda (Md.): National Center for Biotechnology Information (US)).

In BBB permeability modeling, the parenchymal uptake of low molecular weight, paramagnetic positive contrast imaging agents, such as Gd, is representative of solute and ion uptake during BBB disruption, while uptake of higher molecular weight, protein-bound vital dyes, such as Evan's Blue, indicate increased BBB permeability to protein. The observation of brain uptake of both Evan's Blue and Gd in all treatment groups indicates that IRE results in BBB permeability to solutes, ions, and protein, but the discrepancies observed in the lesion sizes as determined with Gd and Evan's Blue qualitatively suggest that BBB permeability induced by IRE is non-uniform. BBB permeability is likely a transient and dynamic process given the electroporation of tissue and disruption of microvascular blood flow that have been shown to occur during delivery of electric pulses (Ellis et al., 2011; Garcia et al., 2010; Garcia P A, Rossmeisl J H, Jr., Neal R E, 2nd, Ellis T L, Davalos R V (2011) A Parametric Study Delineating Irreversible Electroporation from Thermal Damage Based on a Minimally Invasive Intracranial Procedure. Biomed Eng Online 10: 34; Cemazar M, Parkins C S, Holder A L, Chaplin D J, Tozer G M, et al. (2001) Electroporation of human microvascular endothelial cells: evidence for an anti-vascular mechanism of electrochemotherapy. Br J Cancer 84: 565-570).

The results demonstrate significant correlations between the applied electric field and the timing and extent of Gd enhancement. The results also suggest there is a persistent effect on BBB disruption at +15 and +30 minutes post-treatment. This time frame may prove to be advantageous in that it may be feasible to use more advanced, perfusion-based MRI techniques in future studies with IRE in the brain (Mahmood F, Hansen R H, Agerholm-Larsen B, Jensen K S, Iversen H K, et al. (2011) Diffusion-Weighted MRI for Verification of Electroporation-Based Treatments. Journal of Membrane Biology 240: 131-138).

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. Other embodiments of the invention will be apparent to those skilled in the art from consideration of the specification and practice of the invention. For example, the methods of the invention may be modified to treat a variety of CNS-related diseases and conditions (which encompass psychiatric/behavioral diseases or disorders), including, without limitation, acquired epileptiform aphasia, acute disseminated encephalomyelitis, adrenoleukodystrophy, agenesis of the corpus callosum, agnosia, aicardi syndrome, Alexander disease, Alpers' disease, alternating hemiplegia, Alzheimer's disease, amyotrophic lateral sclerosis, anencephaly, Angelman syndrome, angiomatosis, anoxia, aphasia, apraxia, arachnoid cysts, arachnoiditis, Arnold-chiari malformation, arteriovenous malformation, Asperger's syndrome, ataxia telangiectasia, attention deficit hyperactivity disorder, autism, auditory processing disorder, autonomic dysfunction, back pain, Batten disease, Behcet's disease, Bell's palsy, benign essential blepharospasm, benign focal amyotrophy, benign intracranial hypertension, bilateral frontoparietal polymicrogyria, binswanger's disease, blepharospasm, Bloch-sulzberger syndrome, brachial plexus injury, brain abscess, brain damage, brain injury, brain tumor, spinal tumor, Brown-sequard syndrome, canavan disease, carpal tunnel syndrome (cts), causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, charcot-marie-tooth disease, chiari malformation, chorea, chronic inflammatory demyelinating polyneuropathy ("CIDP"), chronic pain, chronic regional pain syndrome, Coffin lowry syndrome, coma (including persistent vegetative state), congenital facial diplegia, corticobasal degeneration, cranial arteritis, craniosynostosis, Creutzfeldt-jakob disease, cumulative trauma disorders, Cushing's syndrome, cytomegalic inclusion body disease ("CIBD"), cytomegalovirus infection, dandy-walker syndrome, Dawson disease, de morsier's syndrome, Dejerine-klumpke palsy, Dejerine-sottas disease, delayed sleep phase syndrome, dementia, dermatomyositis, developmental dyspraxia, diabetic neuropathy, diffuse sclerosis, dysautonomia, dyscalculia, dysgraphia, dyslexia, dystonia, early infantile epileptic encephalopathy, empty sella syndrome, encephalitis, encephalocele, encephalotrigeminal angiomatosis, encopresis, epilepsy, Erb's palsy, erythromelalgia, essential tremor, Fabry's disease, Fahr's syndrome, fainting, familial spastic paralysis, febrile seizures, fisher syndrome, Friedreich's ataxia, Gaucher's disease, Gerstmann's syndrome, giant cell arteritis, giant cell inclusion disease, globoid cell leukodystrophy, gray matter heterotopia, Guillain-barré syndrome, htlv-1 associated myelopathy, Hallervorden-spatz disease, head injury, headache, hemifacial spasm, hereditary spastic paraplegia, heredopathia atactica polyneuritiformis, herpes zoster oticus, herpes zoster, hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile refsum disease, infantile spasms, inflammatory myopathy, intracranial cyst, intracranial hypertension, Joubert syndrome, Kearns-sayre syndrome, Kennedy disease, kinsbourne syndrome, Klippel feil syndrome, Krabbe disease, Kugelberg-welander disease, kuru, lafora disease, Lambert-eaton myasthenic syndrome, Landau-kleffner syndrome, lateral medullary (Wallenberg) syndrome, learning disabilities, leigh's disease, Lennox-gastaut syndrome, Lesch-nyhan syndrome, leukodystrophy, lewy body dementia, lissencephaly, locked-in syndrome, Lou Gehrig's disease, lumbar disc disease, lyme disease-neurological sequelae, machado-joseph disease (spinocerebellar ataxia type 3), macrencephaly, megalencephaly, Melkersson-rosenthal syndrome, Ménière's disease, meningitis, Menkes disease, metachromatic leukodystrophy, microcephaly, migraine, Miller Fisher syndrome, mini-strokes, mitochondrial myopathies, mobius syndrome, monomelic amyotrophy, motor neurone disease, motor skills disorder, moyamoya disease, mucopolysaccharidoses, multi-infarct dementia, multifocal motor neuropathy, multiple sclerosis, multiple system atrophy with postural hypotension, muscular dystrophy, myalgic encephalomyelitis, myasthenia gravis, myelinoclastic diffuse sclerosis, myoclonic encephalopathy of infants, myoclonus, myopathy, myotubular myopathy, myotonia congenita, narcolepsy, neurofibromatosis, neuroleptic malignant syndrome, neurological manifestations of aids, neurological sequelae of lupus, neuromyotonia, neuronal ceroid lipofuscinosis, neuronal migration disorders, niemann-pick disease, non 24-hour sleep-wake syndrome, nonverbal learning disorder, O'sullivan-mcleod syndrome, occipital neuralgia, occult spinal dysraphism sequence, ohtahara syndrome, olivopontocerebellar atrophy, opsoclonus myoclonus syndrome, optic neuritis, orthostatic hypotension, overuse syndrome, palinopsia, paresthesia, Parkinson's disease, paramyotonia congenita, paraneoplastic diseases, paroxysmal attacks, parry-romberg syndrome (also known as rombergs syndrome), pelizaeus-merzbacher disease, periodic paralyses, peripheral neuropathy, persistent vegetative state, pervasive developmental disorders, photic sneeze reflex, phytanic acid storage disease, pick's disease, pinched nerve, pituitary tumors, pmg, polio, polymicrogyria, polymyositis, porencephaly, post-polio syndrome, postherpetic neuralgia ("PHN"), postinfectious encephalomyelitis, postural hypotension, Prader-willi syndrome, primary lateral sclerosis, prion diseases, progressive hemifacial atrophy (also known as Romberg's syndrome), progressive multifocal leukoencephalopathy, progressive sclerosing poliodystrophy, progressive supranuclear palsy, pseudotumor cerebri, ramsay-hunt syndrome (type I and type II), Rasmussen's encephalitis, reflex sympathetic dystrophy syndrome, refsum disease, repetitive motion disorders, repetitive stress injury, restless legs syndrome, retrovirus-associated myelopathy, rett syndrome, Reye's syndrome, Romberg's syndrome, rabies, Saint Vitus' dance, Sandhoff disease, schizophrenia, Schilder's disease, schizencephaly, sensory integration dysfunction, septo-optic dysplasia, shaken baby syndrome, shingles, Shy-drager syndrome, Sjögren's syndrome, sleep apnea, sleeping sickness, snatiation, Sotos syndrome, spasticity, spina bifida, spinal cord injury, spinal cord tumors, spinal muscular atrophy, spinal stenosis, Steele-richardson-olszewski syndrome, see progressive supranuclear palsy, spinocerebellar ataxia, stiff-person syndrome, stroke, Sturge-weber syndrome, subacute sclerosing panencephalitis, subcortical arteriosclerotic encephalopathy, superficial siderosis, sydenham's chorea, syncope, synesthesia, syringomyelia, tardive dyskinesia, Tay-sachs disease, temporal arteritis, tetanus, tethered spinal cord syndrome, Thomsen disease, thoracic outlet syndrome, tic douloureux, Todd's paralysis, Tourette syndrome, transient ischemic attack, transmissible spongiform encephalopathies, transverse myelitis, traumatic brain injury, tremor, trigeminal neuralgia, tropical spastic paraparesis, trypanosomiasis, tuberous sclerosis, vasculitis including temporal arteritis, Von Hippel-lindau disease ("VHL"), Viliuisk encephalomyelitis ("VE"), Wallenberg's syndrome, Werdnig-hoffman disease, west syndrome, whiplash, Williams syndrome, Wilson's disease, and Zellweger syndrome. It is thus appreciated that all CNS-related states and disorders could be treated through the methods of the invention by appropriate modifications, such as the location of placement of the electrode and choice of the exogenous agent administered, which may also include but is not limited to a neurotrophic factor, an enzyme, a neurotransmitter, a neuromodulator, an antibiotic, and an antiviral agent.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. An ablation system comprising:
 a first and second electrode;
 a voltage generator programmed to generate a plurality of electrical pulses between the first and second electrodes placed at a selected separation distance therebetween according to one or more pulse parameters which comprise a voltage-to-distance ratio which is predetermined to:
  cause irreversible electroporation (IRE) of tissue of the mammal within a target ablation zone but insufficient to cause irreversible electroporation in a non-target zone adjacent the target ablation zone; and
  increase susceptibility of the non-target zone to exogenous agents;
 wherein the voltage-to-distance ratio is predetermined to cause temporary disruption of a blood brain barrier (BBB) within the non-target zone;
 wherein the system is adapted to provide for a display of an anticipated ablation zone and an anticipated zone of BBB disruption based on an electric field distribution expected by the plurality of electrical pulses.

2. The system of claim 1, further comprising a detector that detects the occurrence of IRE in the target ablation zone.

3. The system of claim 1, wherein the voltage generator is programmed to generate each electrical pulse as a direct current pulse having a pulse duration of at least 5 microseconds and provide for a voltage-to-distance ratio of from about 10 V/cm to about 10,000 V/cm.

4. The system of claim 1, wherein the voltage generator is programmed to generate each electrical pulse as a direct current pulse having a pulse duration of between 5 and 100 microseconds and provide for a voltage-to-distance ratio of from about 10 V/cm to about 10,000 V/cm.

5. An ablation system comprising:
 a first and second electrode;
 a memory;
 a processor coupled to the memory; and
 a voltage generator programmed to generate a plurality of electrical pulses between the first and second electrodes placed at a selected separation distance therebetween and according to one or more pulse parameters which comprise a voltage-to-distance ratio which is predetermined to be:
  sufficiently strong to cause non-thermal irreversible electroporation (NTIRE) of tissue of the mammal within a target ablation zone but insufficient to cause irreversible electroporation in a non-target zone adjacent the target ablation zone; and
  increase susceptibility of the non-target zone to exogenous agents;
  wherein the voltage-to-distance ratio is predetermined to cause temporary disruption of a blood brain barrier (BBB) within the non-target zone;
  wherein the system is adapted to provide for a display of an anticipated ablation zone and an anticipated zone of BBB disruption based on an electric field distribution expected by the plurality of electrical pulses.

6. The system of claim 5, further comprising a detector that detects the occurrence of IRE in the target ablation zone.

7. The system of claim 5, wherein the voltage generator is programmed to generate each electrical pulse as a direct current pulse having a pulse duration of at least 5 microseconds and provide for a voltage-to-distance ratio of from about 10 V/cm to about 10,000 V/cm.

8. The system of claim 5, wherein the voltage generator is programmed to generate each electrical pulse as a direct current pulse having a pulse duration of between 5 and 100 microseconds and provide for a voltage-to-distance ratio of from about 10 V/cm to about 10,000 V/m.

9. An ablation system comprising:
  a first and second electrode;
  a voltage generator programmed to:
    generate a plurality of electrical pulses between the first and second electrodes placed at a selected separation distance therebetween and according to one or more pulse parameters which comprise a voltage-to-distance ratio predetermined to:
      cause electroporation of brain tissue within a target ablation zone;
      cause temporary disruption of a blood brain barrier (BBB) within a non-target zone adjacent the target ablation zone; and
      increase susceptibility of the non-target zone to exogenous agents; and
    wherein the system is adapted to provide for a display of an anticipated ablation zone and an anticipated zone of BBB disruption based on an electric field distribution expected by e plurality of electrical pulses.

10. The system of claim 9, wherein the display of the anticipated treatment zone is based on a mathematical model.

11. The system of claim 9, wherein the display of the anticipated treatment zone is based on a numerical model.

12. The system of claim 9, wherein the display of the anticipated treatment zone is based on finite element software.

13. The system of claim 9, further comprising a detector that detects electroporation in the target ablation zone and temporary BBB disruption in the non-target zone.

14. The system of claim 9, wherein the voltage generator is programmed to generate direct current pulses.

15. The system of claim 9, wherein the voltage generator is programmed to generate pulses with a duration of at least 5 microseconds.

16. The system of claim 9, wherein the voltage generator is programmed to generate pulses with a voltage-to-distance ratio of from about 10 V/cm to about 10,000 V/cm.

17. The system of claim 9, wherein the voltage generator is programmed to generate pulses with a duration of between 5 and 100 microseconds.

18. The system of claim 17, wherein the voltage generator is programmed to generate pulses with a voltage-to-distance ratio of from about 10 V/cm to about 10,000 V/cm.

* * * * *